United States Patent
Leuthardt et al.

(10) Patent No.: US 11,704,790 B2
(45) Date of Patent: Jul. 18, 2023

(54) SUPERVISED CLASSIFIER FOR OPTIMIZING TARGET FOR NEUROMODULATION, IMPLANT LOCALIZATION, AND ABLATION

(71) Applicants: Eric Leuthardt, St. Louis, MO (US);
Carl Hacker, St. Louis, MO (US);
Shan Siddiqi, St. Louis, MO (US);
Tim Laumann, St. Louis, MO (US);
Andy Daniel, St. Louis, MO (US)

(72) Inventors: Eric Leuthardt, St. Louis, MO (US);
Carl Hacker, St. Louis, MO (US);
Shan Siddiqi, St. Louis, MO (US);
Tim Laumann, St. Louis, MO (US);
Andy Daniel, St. Louis, MO (US)

(73) Assignee: Washington University, St. Louis, MO (US)

(*) Notice: Subject to any disclaimer, the term of this patent is extended or adjusted under 35 U.S.C. 154(b) by 646 days.

(21) Appl. No.: 16/141,605

(22) Filed: Sep. 25, 2018

(65) Prior Publication Data
US 2019/0090749 A1    Mar. 28, 2019

Related U.S. Application Data

(60) Provisional application No. 62/563,471, filed on Sep. 26, 2017.

(51) Int. Cl.
*A61B 5/00* (2006.01)
*G06T 7/00* (2017.01)
(Continued)

(52) U.S. Cl.
CPC .......... *G06T 7/0012* (2013.01); *A61B 5/0042* (2013.01); *A61B 5/055* (2013.01);
(Continued)

(58) Field of Classification Search
CPC ..... A61B 5/0042; A61B 5/4064; A61B 34/10; A61B 5/055; A61B 5/4848; A61B 5/7267;
(Continued)

(56) References Cited

U.S. PATENT DOCUMENTS 9,460,400 B2    10/2016    De Bruin et al.
9,480,402 B2    11/2016    Leuthardt et al.
(Continued)

OTHER PUBLICATIONS

Seeck, Margitta, et al. "Non-invasive epileptic focus localization using EEG-triggered functional MRI and electromagnetic tomography." Electroencephalography and clinical Neurophysiology 106.6 (1998): 508-512. (Year: 1998).*
(Continued)

*Primary Examiner* — Keith M Raymond
*Assistant Examiner* — Fikirte (Fiki) T Ashine
(74) *Attorney, Agent, or Firm* — Armstrong Teasdale LLP

(57) ABSTRACT

A target location for a therapeutic intervention is determined in a subject with a neurological disorder. The target location is selected within at least one resting state network (RSN) map according to a predetermined criterion for the neurological disorder. The at least one RSN map includes a plurality of functional voxels within a brain of the subject, and each functional voxel of the plurality of functional voxels is associated with a probability of membership in an RSN. Instructions are transmitted to a treatment system that cause operation to be performed on the selected target location.

20 Claims, 56 Drawing Sheets
(46 of 56 Drawing Sheet(s) Filed in Color)

(51) Int. Cl.

| | |
|---|---|
| *A61B 34/10* | (2016.01) |
| *A61B 5/055* | (2006.01) |
| *G16H 30/40* | (2018.01) |
| *G06N 3/00* | (2023.01) |
| *G16H 50/20* | (2018.01) |
| *G06F 18/213* | (2023.01) |
| *G06F 18/21* | (2023.01) |
| *G06F 18/2415* | (2023.01) |
| *G06F 18/2413* | (2023.01) |
| *G06V 10/764* | (2022.01) |
| *G01R 33/48* | (2006.01) |
| *G16H 20/40* | (2018.01) |

(52) U.S. Cl.
CPC ............ *A61B 5/4064* (2013.01); *A61B 34/10* (2016.02); *G06F 18/213* (2023.01); *G06F 18/2178* (2023.01); *G06F 18/2415* (2023.01); *G06F 18/24133* (2023.01); *G06N 3/00* (2013.01); *G06V 10/764* (2022.01); *G16H 30/40* (2018.01); *G16H 50/20* (2018.01); *A61B 5/4848* (2013.01); *A61B 5/7267* (2013.01); *A61B 2034/107* (2016.02); *A61B 2576/026* (2013.01); *G01R 33/4806* (2013.01); *G06T 2207/20081* (2013.01); *G06T 2207/20084* (2013.01); *G06T 2207/30016* (2013.01); *G06V 2201/031* (2022.01); *G16H 20/40* (2018.01)

(58) Field of Classification Search
CPC ........ A61B 2034/107; A61B 2576/026; A61B 2034/2055; G06K 9/6271; G06K 9/6232; G06K 9/6277; G06K 9/6263; G06K 2209/051; G16H 30/40; G16H 50/20; G16H 20/40; G06N 3/00; G06N 3/08; G06T 7/0012; G06T 2207/20084; G06T 2207/20081; G06T 2207/30016; G01R 33/4806

See application file for complete search history.

(56) References Cited

U.S. PATENT DOCUMENTS

| | | |
|---|---|---|
| 2014/0073905 A1 | 3/2014 | Jordan et al. |
| 2015/0119689 A1 | 4/2015 | Pascual-Leone et al. |
| 2016/0210552 A1 | 7/2016 | Kasabov et al. |
| 2016/0345911 A1 | 12/2016 | Leuthardt et al. |

OTHER PUBLICATIONS

Bénar, Christian-G., et al. "The BOLD response to interictal epileptiform discharges." Neuroimage 17.3 (2002): 1182-1192. (Year: 2002).*
Zijlmans, Maeike, et al. "EEG-fMRI in the preoperative work-up for epilepsy surgery." Brain 130.9 (2007): 2343-2353. (Year: 2007).*
An, Dongmei, et al. "Electroencephalography/functional magnetic resonance imaging responses help predict surgical outcome in focal epilepsy." Epilepsia 54.12 (2013): 2184-2194. (Year: 2013).*
Siddiqi, Shan H., et al. "Individualized connectome-targeted transcranial magnetic stimulation for neuropsychiatric sequelae of repetitive traumatic brain injury in a retired NFL player." The Journal of neuropsychiatry and clinical neurosciences 31.3 (2019): 254-263. (Year: 2019).*
Mitchell et al., (hereafter Mitchell), A Novel Data-Driven Approach to Preoperative Mapping of Functional Cortex Using Resting-State Functional Magnetic Resonance Imaging, published Dec. 2013 (Year: 2013).*
Mitchell et al. , "A Novel Data-Driven Approach to Preoperative Mapping of Functional Cortex Using Resting-State Functional Magnetic Resonance Imaging" (Year: 2013).*
Beckmann, C.F. et al., "Investigations into resting-state connectivity using independent component analysis," Philosophical Transactions of the Royal Society B, 360(1457): 1001-1013 (2005).
Biswal, B. et al., "Functional connectivity in the motor cortex of resting human brain using echo-planar MRI," Magnetic Resonance in Medicine, 34(4): 537-541 (1995).
Brier, M.R. et al., "Loss of intranetwork and internetwork resting state functional connections with Alzheimer's disease progression," Journal of Neuroscience, 32(26): 8890-8899 (2012).
Fox, M.D. et al., "Identification of reproducible individualized targets for treatment of depression with TMS based on intrinsic connectivity," NeuroImage, 66: 151-160 (2013).
Glasser, M.F. et al., "A multi-modal parcellation of human cerebral cortex," Nature, 536(7615): 171-178 (2016).
Hacker, C.D. et al., "Resting state network estimation in individual subjects," NeuroImage, 82: 616-633 (2013). Accessed at: http://www.ncbi.nlm.nih.gov/pubmed/23735260.
Hacker, C.D. et al., "Resting state functional connectivity of the striatum in Parkinson's disease," Brain, 135(12): 3699-3711 (2012).
Laumann, T.O. et al., "Functional System and Areal Organization of a Highly Sampled Individual Human Brain," Neuron, 87(3): 657-670 (2015).
Marcus D.S. et al., "The Extensible Neuroimaging Archive Toolkit: an Informatics platform for managing, exploring, and sharing neuroimaging data," Neuroinformatics, 5(1): 11-33 (2007).
Martino, J. et al., "Resting functional connectivity in patients with brain tumors in eloquent areas," Annals of Neurology, 69(3): 521-532 (2011). Accessed at: https://www ncbi.nlm nih.gov/pmc/articles/PMC4090361/.
Mitchell, T.J. et al., "A Novel Data-Driven Approach to Preoperative Mapping of Functional Cortex Using Resting-State Functional Magnetic Resonance Imaging," Neurosurgery, 73(6): 969-983 (2013).
Otten, M.L. et al., "Motor deficits correlate with resting state motor network connectivity in patients with brain tumors," Brain, 135(4): 1017-1026 (2012).
Shannon, B.J. et al., "Morning-evening variation in human brain metabolism and memory circuits," Journal of Neurophysiology, 109(5): 1444-1456 (2013).
Smyser, C.D. et al., "Effects of white matter injury on resting state fMRI measures in prematurely born infants," PloS ONE, 8(7): e68098, 12 pages (2013).
Thomas, J.B. et al., "Pathways to neurodegeneration: effects of HIV and aging on resting-state functional connectivity," Neurology, 80(13): 1186-1193 (2013).
Vincent, J.L. et al., "Intrinsic functional architecture in the anaesthetized monkey brain," Nature, 447(7140): 83-86 (2007).
Wang, D. et al. "Parcellating cortical functional networks in individuals," Nature Neuroscience, 18(12): 1853-1860 (2015). Accessed at: https://www.ncbi.nlm.nih.gov/pmc/articles/PMC4661084/.

* cited by examiner

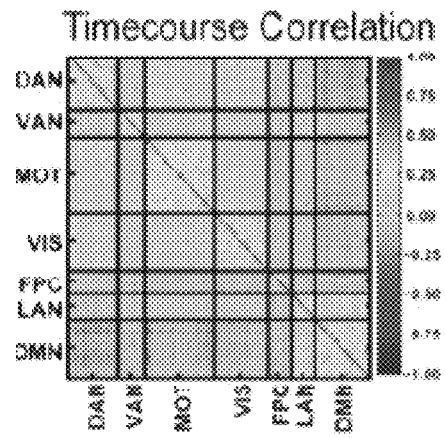
FIG. 8A
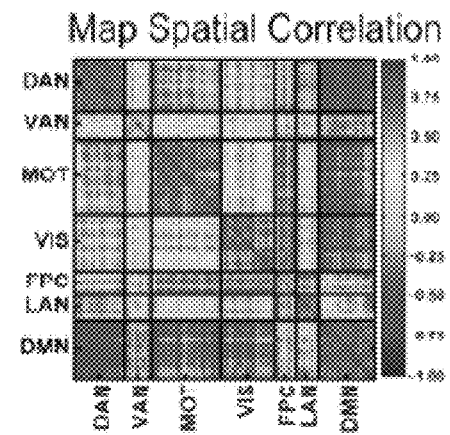
FIG. 8B
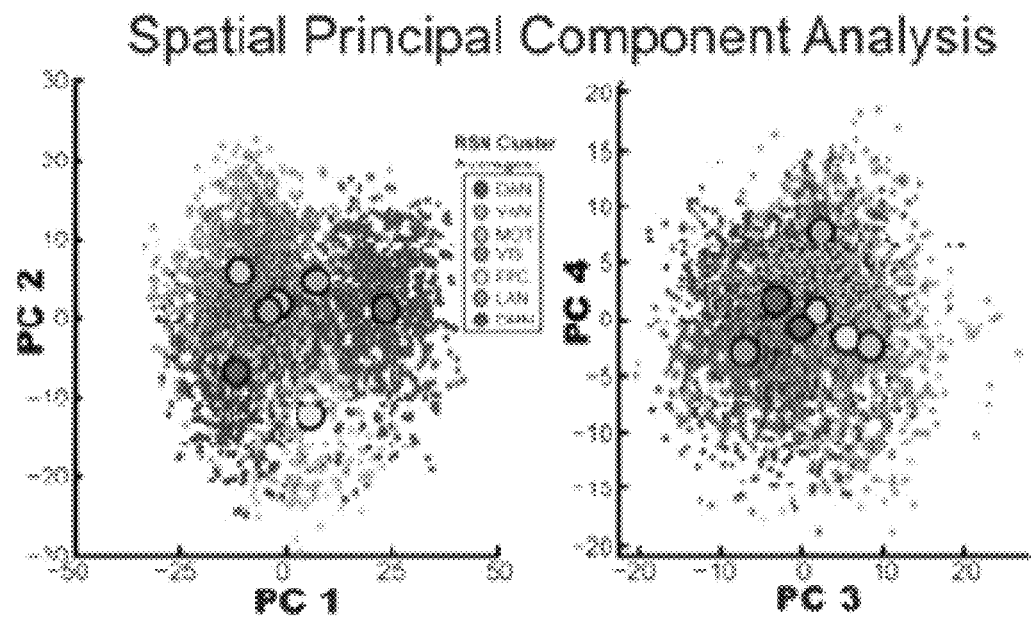
FIG. 8C  FIG. 8D

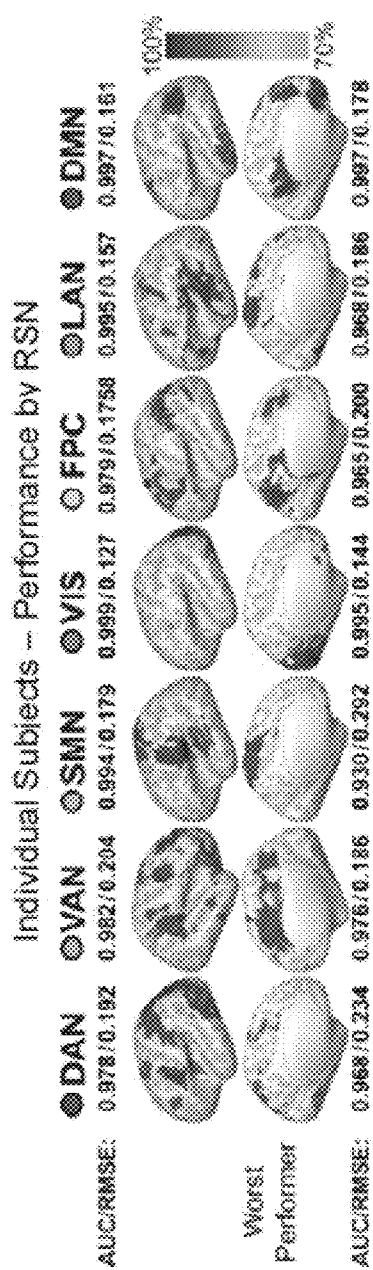
FIG. 11C
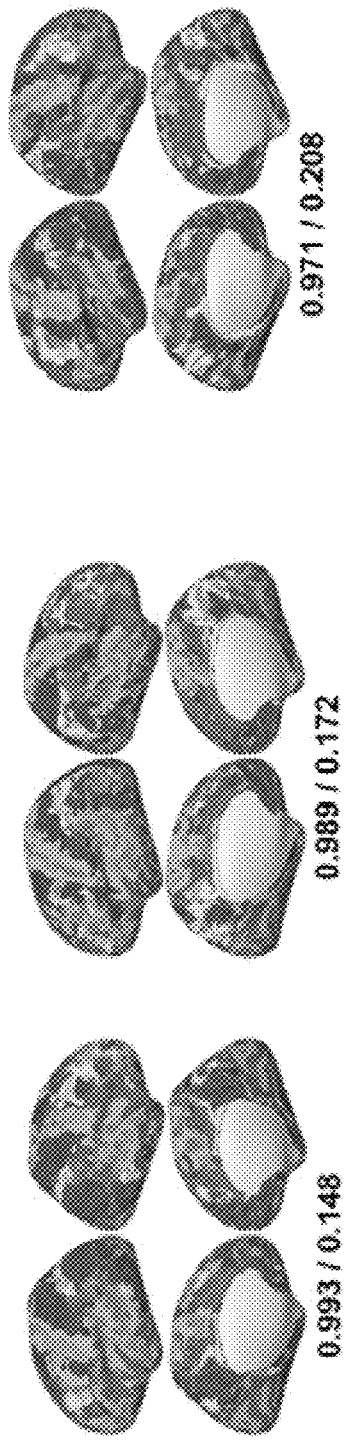
FIG. 11F
FIG. 11E
FIG. 11D

GROUP AVERAGE

STANDARD DEVIATION

WINNER-TAKE-ALL

◆ TBI  ▲ HC  ■ Subject (pre-treatment)  ■ Subject (post-treatment)

♦ TBI   ▲ HC   ■ Subject (pre-treatment)   ■ Subject (post-treatment)

◆ TBI   ▲ HC   ■ Subject (pre-treatment)   ■ Subject (post-treatment)

◆ TBI   ▲ HC   ■ Subject (pre-treatment)   ■ Subject (post-treatment)

◆ TBI ▲ HC ■ Subject (pre-treatment) ■ Subject (post-treatment)

Pre-treament
Post-treament
Differential

1. Localization

2. Co-registration

3. Implantation

4. Integration

SUPERVISED CLASSIFIER FOR OPTIMIZING TARGET FOR NEUROMODULATION, IMPLANT LOCALIZATION, AND ABLATION

CROSS REFERENCE TO RELATED APPLICATIONS

This application claims priority to U.S. Provisional Application Ser. No. 62/563,471, filed Sep. 26, 2017, the contents of which are incorporated herein in its entirety.

STATEMENT REGARDING FEDERALLY SPONSORED RESEARCH & DEVELOPMENT

This invention was made with government support under grant 5R21CA159470-02 awarded by the National Institutes of Health. The government has certain rights in the invention.

BACKGROUND

Functional MRI imaging of the brain has enabled detailed functional mapping that reflects the functional organization of the brain. Task-based fMRI has been employed as one means of localizing function. However, task-based fMRI depends on the patient's ability to comply with the task paradigm, which may be lacking for various reasons. Resting state functional magnetic resonance imaging (rs-fMRI) has also been used to localize function without need for prescribed activity on the part of the patient. Moreover, rs-fMRI is highly efficient, as multiple resting state networks (RSNs) associated with multiple cognitive domains can be mapped at the same time.

An ongoing challenge preventing widespread use of rs-fMRI by neurosurgical practitioners is the high degree of advanced imaging expertise currently necessary to create and interpret the images. Existing seed-based methods make use of judiciously selected regions of the brain to produce functional maps using rs-fMRI data, but these seed-based methods rely upon population-based analysis of rs-fMRI data and may be less adaptable for obtaining functional maps of individual patients. Further, the reliance of seed-based functional mapping methods on expert user inputs make these methods less approachable to potential clinical practitioners that may lack the training and expertise needed to obtain meaningful results.

rs-fMRI methodology currently is dominated by two complementary strategies: spatial Independent Components Analysis (sICA), and seed-based correlation analysis (SCA). Both strategies assign RSN identities to brain voxels by exploiting the observation that spontaneous neural activity is correlated (coherent) within widely distributed regions of the brain. Both strategies yield highly reproducible results at the group level in normal subjects. The sICA method decomposes resting state fMRI data into a sum of components, each component corresponding to a spatial topography and a time course. Since the sICA method makes no a priori assumptions regarding the topography of RSNs, this method exemplifies an unsupervised classification method. The principal advantage of the sICA method is that it provides a direct means of separating artifact from blood oxygen level dependent (BOLD) signals of neural origin, although this separation typically requires observer expertise. Further, the results obtained by the sICA method may vary substantially depending on processing parameters (e.g., the number of requested components). Thus, the sICA method can be difficult to use in the investigation of targeted RSNs, especially in single subjects. In practice, the user typically selects the component of interest from the many returned by sICA based on the user's expertise. In contrast, seed-based correlation analysis (SCA) methods compute RSNs by voxel-wise evaluation of the Pearson correlation between the time courses and an a priori targeted region of interest (ROI) and all other voxels in the brain. The principal difficulty in using seed-based correlation mapping is exclusion of non-neural artifacts, which typically is accomplished using regression techniques. However, SCA may not be reliable when brain anatomy has been distorted by mass effects or RSNs have been rearranged to compensate for focal loss of function.

Supervised classification methods, including a supervised classification using a multilayer perceptron (MLP), have been developed to identify canonical brain networks from rs-fMRI data in an automated system. The supervised classification systems using a multilayer perceptron (MLP) enable a relatively untrained practitioner to obtain functional maps of individual patients for use in a variety of clinical and surgical applications. The more widespread use of functional mapping by clinical and surgical practitioners made possible by supervised classification systems using the multilayer perceptron (MLP) enables the use of functional mapping for localization of therapeutic interventions such as neuromodulation, surgical ablation, or implants, for guidance of neurosurgical or radiotherapeutic interventions to avoid avoidance of critical structures, for diagnosis of neurological disorders, and for assessment of treatment efficacy for neurological disorders. In addition, functional mapping results obtained by supervised classification systems using a multilayer perceptron (MLP) may be provided as regions of interest for seed-based functional connectivity analysis to improve individualization of these methods. The use of functional mapping information obtained using supervised classification systems using the multilayer perceptron (MLP) to analyze rs-fMRI data to guide neurosurgical interventions may potentially improve survival and quality of life after surgical resection of brain tumors by improving the identification and preservation of eloquent cortex.

Non-invasive treatments, such as repetitive transcranial magnetic stimulation (rTMS), are increasingly used for the treatment of a variety of neurological and other brain disorders including major depressive disorder (MDD), in stroke rehabilitation, and more recently for the treatment of depression associated with traumatic brain injury (TBI). rTMS is thought to exert a therapeutic effect via selective modulation of cortical excitability. The effectiveness of various non-invasive treatments, such as rTMS, is enhanced by accurate targeting of the non-invasive treatment to the brain region associated with the appropriate neural function.

By way of non-limiting example, neuromodulation via rTMS for the treatment of depression associated with TBI faces challenges due to potentially exaggerated inter-individual network variability, which is substantial even in healthy individuals. TBI is associated with connectivity changes in regions and networks involved in emotion regulation, including anterior cingulate cortex (ACC), dorsolateral prefrontal cortex (DLPFC), dorsal attention network (DAN), and default mode network (DMN). Existing approaches for the targeting of treatment relied on connectivity with seeds derived from group averages. However, the use of individualized rs-fMRI maps created using the supervised classification methods using a multilayer perceptron (MLP) described above may enhance the efficacy of rTMS treatment of TBI-associated depression and other neurological disorders.

BRIEF DESCRIPTION

In one aspect, a method for determining a target location for a therapeutic intervention in a subject with a neurological disorder includes selecting the target location within at least one resting state network (RSN) map according to a predetermined criterion for the neurological disorder. Each of the at least one RSN maps includes a plurality of functional voxels within a brain of the subject, and each functional voxel of the plurality of functional voxels is associated with a probability of membership in an RSN.

In another aspect, a method for monitoring an efficacy of a therapeutic intervention in a subject with a neurological disorder includes providing at least one pre-treatment RSN map of the subject prior to the therapeutic intervention. Each of the at least one pre-treatment RSN maps includes a plurality of pre-treatment functional voxels within a brain of the subject, and each pre-treatment functional voxel of the plurality of pre-treatment functional voxels is associated with a probability of membership in an RSN. The method also includes providing at least one post-treatment RSN map of the subject after the therapeutic intervention. Each of the at least one post-treatment RSN maps includes a plurality of post-treatment functional voxels within the brain of the subject and each post-treatment functional voxel of the plurality of post-treatment functional voxels is associated with a probability of membership in an RSN. The method additionally includes providing at least one control RSN map representative of a healthy subject. Each of the at least one control RSN maps includes a plurality of control functional voxels within the brain of the healthy subject and each control functional voxel of the plurality of control functional voxels is associated with a probability of membership in an RSN. The method further includes comparing at least a portion of each of the at least one pre-treatment RSN maps, the at least one post-treatment RSN maps, and the at least one control RSN map to determine changes in the at least one post-treatment RSN map, and determining the efficacy of the therapeutic intervention based on the identified changes according to an efficacy criterion.

In an additional aspect, a method for selecting a seed region for use in a seed-based cortical functional mapping method includes providing at least one RSN map of at least one subject. Each of the at least one RSN maps includes a plurality of functional voxels within a brain of the subject, and each functional voxel of the plurality of functional voxels is associated with a probability of membership in an RSN. The method further includes selecting a subset of the functional voxels characterizing a contiguous region as the seed region. Each functional voxel of the seed region has a probability of membership in the RSN above a threshold value.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 8A-8D are graphs depicting correlation maps;

FIGS. 11A-11F are schematics of topographies in individual subjects;

DETAILED DESCRIPTION

Figure 1:
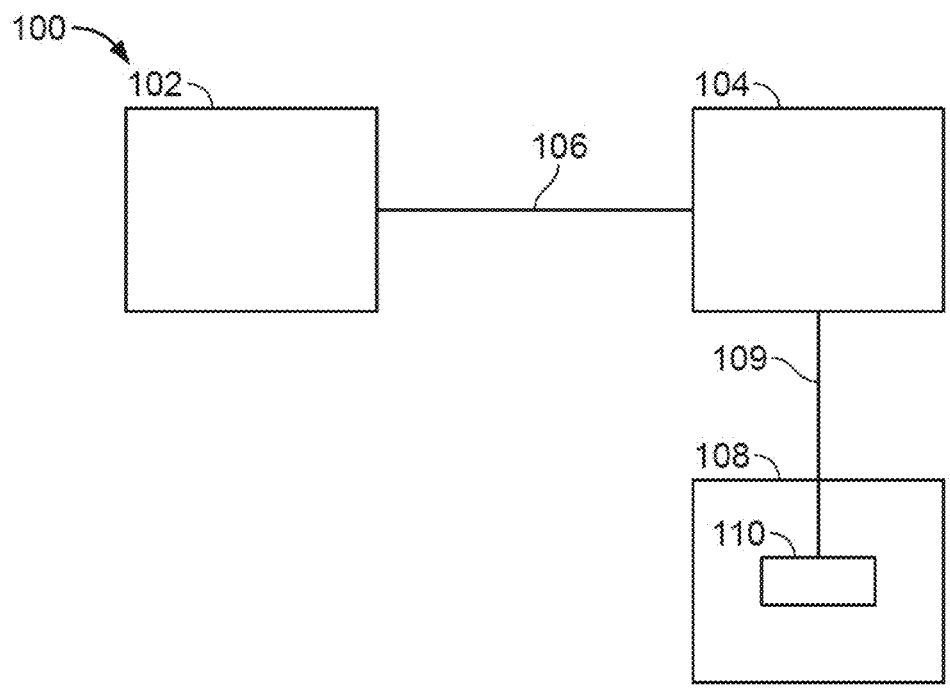
FIG. 1 is a block diagram of an exemplary system for task-less mapping of brain activity.

In various aspects, systems and methods are disclosed that make use of supervised classification methods, including but not limited to a supervised classification method using a multilayer perceptron (MLP) to produce individualized cortical functional maps for use in a variety of applications as described below. This structured classification methodology is robust and amenable to implementation in automated systems suitable for use by clinical practitioners to analyze a resting state functional MRI (rs-fMRI) data set obtained from a subject and to identify and map canonical brain networks, also referred to herein as resting state networks (RSNs), for a variety of clinical applications. In one aspect, the canonical brain networks may be used for the purpose of brain mapping and surgical navigation. In another aspect, the canonical brain networks may be used to diagnose one or more neurological disorders, guide an administration of a treatment of the one or more neurological disorders, and/or monitor an efficacy of a treatment of the one or more neurological disorders.

Non-limiting examples of neurological disorders suitable for diagnosis and monitoring using the systems and methods described below include psychiatric disorders including mood disorders such as depression, anxiety disorders, obsessive-compulsive and related disorders, trauma and stressor-related disorders, impulse control disorders, psychotic disorders, autism spectrum and other neurodevelopmental disorders, eating disorders, substance-related/addictive disorders, somatoform disorders, personality disorders, and attentional disorders, as well as disorders secondary to general medical/neurologic illnesses, movement/tic disorders, seizure disorders, headaches, tinnitus, neuroinflammatory disorders, focal brain lesions, pain syndromes, brain injury, stroke, brain tumor, coma, neurocognitive disorders, neurodegenerative disorders, and any combination thereof.

In various other aspects, the same canonical brain networks are used to identify an optimal location for the administration of one or more therapeutic interventions. In some aspects, the canonical brain networks identified using the disclosed systems and methods are used to identify optimal locations for the administration of a treatment of one or more neurological disorders. Non-limiting examples of neurological disorders include a psychiatric disorder, a seizure disorder, a brain tumor, and a stroke. Non-limiting examples of treatments for the one or more neurological disorders include cortical stimulation, subcortical stimulation, cerebellar stimulation, cortical inhibition, subcortical inhibition, cerebellar inhibition, cortical neuromodulation, subcortical neuromodulation, cerebellar neuromodulation, and any combination thereof. Non-limiting examples of suitable devices for the treatment of one or more neurological disorders include transcranial magnetic stimulation (TMS) devices, deep brain stimulation (DBS) devices, ultrasound (US) devices, optical stimulator devices, cortical stimulator devices, subcortical stimulator devices, and cerebellar stimulator devices. Additional non-limiting examples of suitable devices for the treatment of one or more neurological disorders include implantable drug release devices and electroconvulsive therapy devices.

By way of non-limiting example, the disclosed systems and methods may be used to determine an optimal implantation location for a brain computer interface or a brain stimulator for a treatment of a stroke or a motor disability based on correlations of the implantation location with a somatomotor network. By way of another non-limiting example, the disclosed systems and methods may be used to determine an optimal implantation location for a brain computer interface for a treatment of a communication disorders based on correlations of the implantation location with a language network. By way of an additional non-limiting example, the disclosed systems and methods may be used to determine an optimal implantation location for a brain stimulator for a neural augmentation treatment based on correlations of the implantation location with dorsal language network.

In other aspects, the canonical brain networks identified using the disclosed systems and methods are used to identify optimal locations for the administration of a treatment to enable neural augmentation. Non-limiting examples of suitable devices for the administration of a treatment to enable neural augmentation include transcranial magnetic stimulation (TMS) devices, deep brain stimulation (DBS) devices, ultrasound (US) devices, optical stimulator devices, cortical stimulator devices, subcortical stimulator devices, and cerebellar stimulator devices. Non-limiting examples of neural augmentation enabled by the treatment include enhanced attention, enhanced memory, enhanced fluid cognition, enhanced social cognition, and various combinations thereof.

In additional aspects, the canonical brain networks identified using the disclosed systems and methods are used to identify optimal locations for the ablation of neural tissue to optimize treatment of a cancer, epilepsy, and functional disorders. Non-limiting examples of suitable methods of ablation include surgical ablation, radiation therapy, laser interstitial thermal therapy, and any combination thereof. In other additional aspects, the canonical brain networks identified using the disclosed systems and methods are used to target avoidance of critical structures in surgery, laser interstitial thermal therapy (LITT), radiation therapy and any combination thereof.

In other additional aspects, the canonical brain networks identified using the disclosed systems and methods are used as regions of interest for existing seed-based functional connectivity analysis in order to improve individualization of these methods. These existing methods rely on seeds that are based on large-group studies of healthy individuals, which are likely not applicable to individual patients with neurological disorders.

Figure 41:
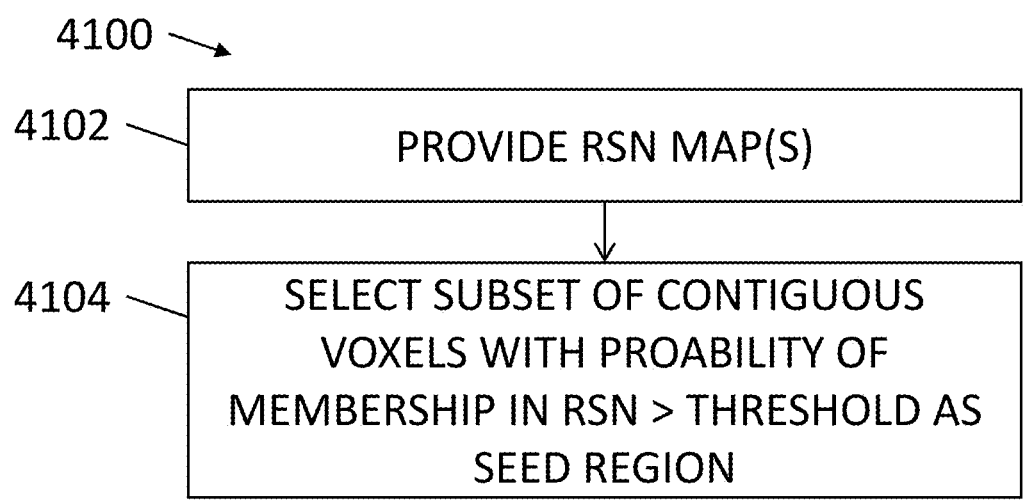
FIG. 41 is a flow chart summarizing the steps of a method for identifying seed regions according to one aspect of the disclosure.

FIG. 41 illustrates a method 4100 is a flowchart summarizing a method 4100 of determining a seed location for use in a seed-based cortical functional mapping method in one aspect. As illustrated in FIG. 41, the method 4100 includes providing at least one RSN map of at least one subject at 4102. Each of the at least one RSN maps includes a plurality of functional voxels within a brain of the subject. Each functional voxel of the plurality of functional voxels is associated with a probability of membership in an RSN. The method 4100 also includes selecting a subset of the functional voxels characterizing a contiguous region as the seed region at 4104. Each functional voxel selected for the seed region at 4104 has a probability of membership in the RSN above a threshold value. In one aspect, the subset of the functional voxels selected for the seed region include probabilities of membership in the RSN within the highest 10% of all probabilities of membership of all functional voxels of the at least one RSN map. In one aspect, the subset of the functional voxels selected for the seed region include probabilities of membership in the RSN within the highest 5% of all probabilities of membership of all functional voxels of the at least one RSN map. In one aspect, the subset of the functional voxels selected for the seed region include probabilities of membership in the RSN within the highest 3% of all probabilities of membership of all functional voxels of the at least one RSN map.

In addition, the canonical brain networks identified using the disclosed systems and methods is useful for developing diagnostic tools based on disease-specific individualized functional connectivity results, and/or for monitoring the efficacy of a treatment monitoring by measuring changes in individualized network connectivity, which can help to predict whether a patient is likely to respond to a particular therapy. Suitable treatments that may be monitored for efficacy using the disclosed systems and methods include, but are not limited to implantable brain stimulators, non-invasive transcranial magnetic stimulation, non-invasive direct transcranial electric stimulation, implantable drug release devices, other pharmacologic interventions, electroconvulsive therapy, cognitive and behavioral therapy, and psychotherapy.

In one aspect, the disclosed systems and methods enable the generation and analysis of disease-specific individualized functional connectivity results that may be used to diagnose a neurological disorder in a subject based on the individual subject's canonical brain networks. In another aspect, individualized functional connectivity results obtained using the disclosed systems and methods enable a differential diagnosis of a neurological disorder in a subject from a group of candidate neurological disorders that are otherwise relatively indistinguishable due to similar symptoms and/or diagnostic parameter values. By way of non-limiting example, described in detail in Ex. 4 below, individualized functional connectivity results were capable of distinguishing a patient with chronic traumatic encephalopathy from both healthy control subjects and subjects with regular traumatic brain injury-associated symptoms.

In an additional aspect, measured changes in individualized functional connectivity results obtained using the disclosed systems and methods may help to predict whether a patient is likely to respond to a particular therapy. By way of non-limiting example, described in detail in Ex. 9 below, baseline connectivity analysis using Perceptron-generated ROIs appeared to predict TMS-induced connectivity changes more effectively than established network ROIs.

In various aspects, systems and methods are disclosed for determining correlations between one or more portions of a resting-state functional MRI (rs-fMRI) data set obtained from an individual subject characterizing one or more resting state networks and one or more additional portions of the rs-fMRI data set characterizing one or more regions of interest within a brain of the subject. The one or more portions of the resting-state functional MRI (rs-fMRI) data set characterizing the one or more resting state networks are obtained using a multi-layer perceptron (MLP) algorithm that assigns a probability of RSN membership to each locus within the brain using supervised classification of the rs-fMRI data.

In various aspects, the correlations obtained using the disclosed methods may be used for a variety of purposes including, but not limited to, diagnosing a neurological disorder in the subject, determining a therapeutic efficacy of a treatment for a neurological disorder in the subject, guiding a brain surgery on a predetermined region of interest (ROI) of a subject, and selecting a target region for administering a therapeutic intervention for a neurological disorder to a subject. In some aspects, the correlations may be used to identify seed regions for use in existing seed-based methods of cortical functional mapping to enhance the accuracy of these existing methods. In various aspect, the information associated with the method for guiding a brain surgery on a predetermined region of interest (ROI) of a subject, or the method for selecting a region for administering a treatment for a neurological disorder to a subject may be integrated into the operational systems of existing neuronavigation devices and/or therapeutic devices such as repetitive transcranial magnetic stimulation (rTMS) devices.

In one aspect, a probability of RSN membership is assigned to each locus within the brain of a subject using any suitable functional mapping method without limitation. In another aspect, the functional mapping method used in the methods disclosed below are any supervised classifier method without limitation including, but not limited to, the supervised classifier methods as described in U.S. Pat. No. 9,480,402, which is incorporated herein in its entirety.

In one aspect, the supervised classifier method is a multi-layer perceptron (MLP) algorithm that assigns RSN membership to each locus within the brain using supervised classification of rs-fMRI data. Current data, presented in the examples below, demonstrate that MLP-based RSN mapping is more reliable than conventional task-based fMRI and is extremely sensitive to sites identified by cortical stimulation, which currently represent the gold standard in pre-surgical planning and intraoperative mapping.

The disclosed strategy for resting state network (RSN) mapping using a multi-layer perceptron (MLP) exemplifies supervised classification; therefore, unlike previous methods for mapping RSNs, which are unsupervised, MLP-based RSN mapping can be performed quickly, automatically, and reliably in individuals.

In various aspects, a multi-layer perceptron (MLP)-based analysis tool, described herein, assigns RSN membership (e.g., somatomotor, language) to each locus within the brain. MLP-based RSN mapping is a powerful tool for automating the identification of resting state networks in individuals. MLP-based RSN mapping has been shown to be effective in presurgical planning. Additionally, MLP-based RSN mapping has been shown to correspond to results obtained by cortical stimulation, currently the neurosurgical gold standard for localization function. Preliminary data presented below demonstrate that MLP-based RSN mapping offers more reliable functional localization than existing MRI-based cortical functional mapping methods, including task-based fMRI.

Task-based fMRI depends on the patient's ability to comply with the task paradigm, which frequently is lacking; consequently, this procedure often does not provide useful information. Moreover, task-based fMRI typically is restricted to mapping the representation of motor and speech function, which omits other important functions, such as executive function. Recently, it has been shown that the representation of multiple motor, sensory, and cognitive functions can be mapped by analysis of intrinsic brain activity, acquisition of which requires only that the patient hold still during fMRI. Even the waking state during fMRI is not required as essentially the same functional maps are obtained even if the patient is asleep or sedated. This "resting state" fMRI (rs-fMRI) provides a much more complete functional map of the brain than does task-based fMRI. Moreover, rs-fMRI is more reliable and much more time-efficient. The use of rs-fMRI in combination with the MLP-based RSN mapping methods disclosed herein enable the seamless and automatic analysis of resting state fMRI data and the generation of maps of multiple canonical brain networks (i.e., somatomotor, language, ventral attention, dorsal attention, default mode, visual, and frontoparietal control The RSN mapping method may be implemented such that all algorithms/calculations can be performed rapidly on a single computer and interface with clinical Picture Archiving and Communication System (PACS) systems and existing neuronavigation systems including, but not limited to, the Medtronic Stealth Station Navigation System.

The exemplary systems, apparatus, and methods described herein overcome at least some known disadvantages associated with at least some known brain mapping techniques, such as task-based and/or task-less systems. More specifically, the embodiments described herein include a computing device for use in a system for mapping brain activity of a subject that generally comprises a processor. The processor is programmed to select a plurality of measurements of brain activity that is representative of at least one parameter of a brain of the subject during a resting state. Moreover, the processor is programmed to compare at least one data point from each of the measurements with a corresponding data point from a previously acquired data set from at least one other subject. The processor is also programmed to produce at least one map for each of the measurements based on the comparison of the resting state data point and the corresponding previously acquired data point. The processor may also be programmed to categorize the brain activity in a plurality of networks in the brain based on the map. By using previously acquired data points to categorize the brain activity in a plurality of networks in the brain of the subject, task-based techniques can be avoided. Moreover, by having the processor select the plurality of measurements, a user may no longer need to spend a considerable amount of time determining which measurements, such as voxels, to select.

FIG. 1 illustrates an exemplary system 100 for mapping brain activity of a subject (not shown). It should be noted that the term "brain activity" as used herein includes the various activities within a brain of the subject that correspond to various tasks performed by the subject. For example, the brain transmits and receives signals in the form of hormones, nerve impulses, and chemical messengers that enable the subject to move, eat, sleep, and think. In the exemplary embodiment, system 100 is used to identify locations within a plurality of networks within the brain that are responsible for such brain activities.

As seen in FIG. 1, system 100 includes a sensing system 102 that is configured to detect a plurality of measurements of brain activity that is representative of at least one parameter of the brain of the subject during a resting state. In one suitable embodiment, sensing system 102 is a magnetic resonance imaging device (MRI) that is configured to generate at least one spectroscopic signal representative of a plurality of measurements of brain activity that is representative of at least one parameter of the brain of the subject during a resting state. More specifically, sensing system 102 may generate an altered magnetic field within the brain to measure various parameters of the brain. In another suitable embodiment, sensing system 102 may be a specialized MRI, such as a functional magnetic resonance imaging (fMRI) device that is used to measure a variation in blood flow (hemodynamic response) related to neural activity in the brain or spinal cord (not shown) of the subject. In yet another suitable embodiment, sensing system 102 may be an electrocorticography device having at least one electrode (not shown) to measure at least one voltage fluctuation within the brain. It should be noted that the present disclosure is not limited to any one particular type of imaging and electrical technique or device, and one of ordinary skill in the art will appreciate that the current disclosure may be used in connection with any type of technique or device that enables system 100 to function as described herein.

In the exemplary embodiment, system 100 also includes a computing device 104 coupled to sensing system 102 via a data conduit 106. It should be noted that, as used herein, the term "couple" is not limited to a direct mechanical, electrical, and/or communication connection between components, but may also include an indirect mechanical, electrical, and/or communication connection between multiple components. Sensing system 102 may communicate with computing device 104 using a wired network connection (e.g., Ethernet or an optical fiber), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, N.Y. WIMAX is a registered trademark of WiMax Forum, of Beaverton, Oreg. BLUETOOTH is a registered trademark of Bluetooth SIG, Inc. of Kirkland, Wash.

In the exemplary embodiment, computing device 104 is configured to receive at least one signal representative of a plurality of measurements of brain activity from sensing system 102. More specifically, computing device 104 is configured to receive at least one signal representative of an altered magnetic field within the brain of the subject from sensing system 102. Alternatively, computing device 104 may be configured to receive at least one signal representative of at least one voltage fluctuation within the brain from at least one electrode.

System 100 also includes a data management system 108 that is coupled to computing device 104 via a network 109. Data management system 108 may be any device capable of accessing network 109 including, without limitation, a desktop computer, a laptop computer, or other web-based connectable equipment. More specifically, in the exemplary embodiment, data management system 108 includes a database 110 that includes previously acquired data of other subjects. In the exemplary embodiment, database 110 can be fully or partially implemented in a cloud computing environment such that data from the database is received from one or more computers (not shown) within system 100 or remote from system 100. In the exemplary embodiment, the previously acquired data of the other subjects may include, for example, a plurality of measurements of brain activity that is representative of at least one parameter of a brain of each of the subjects during a resting state. Database 110 can also include any additional information of each of the subjects that enables system 100 to function as described herein.

Data management system 108 may communicate with computing device 104 using a wired network connection (e.g., Ethernet or an optical fiber), a wireless communication means, such as, but not limited to radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a cellular phone technology (e.g., the Global Standard for Mobile communication (GSM)), a satellite communication link, and/or any other suitable communication means. More specifically, in the exemplary embodiment, data management system 108 transmits the data for the subjects to computing device 104. While the data is shown as being stored in database 110 within data management system 108, it should be noted that the data of the subjects may be stored in another system and/or device. For example, computing device 104 may store the data therein.

During operation, while the subject is in a resting state, sensing system 102 uses a magnetic field to align the magnetization of some atoms in the brain of the subject and radio frequency fields to systematically alter the alignment of this magnetization. As such, rotating magnetic fields are produced and are detectable by a scanner (not shown) within sensing system 102. More specifically, in the exemplary embodiment, sensing system 102 detects a plurality of measurements of brain activity that is representative of at least one parameter of the brain of the subject during the resting state. Sensing system 102 also generates at least one spectroscopic signal representative of the plurality of measurements and transmits the signal(s) to computing device 104 via data conduit 106. Moreover, data of other subjects may be transmitted to computing device 104 from database 110 via network 109. As explained in more detail below, computing device 104 produces at least one map, such as a functional connectivity map, for each of the measurements based on a comparison of at least one resting state data point of the subject and a corresponding data point from the previously acquired data set from at least one other subject. Computing device 104 uses the map to categorize or classify the brain activity in a plurality of networks in the brain.

Figure 2:
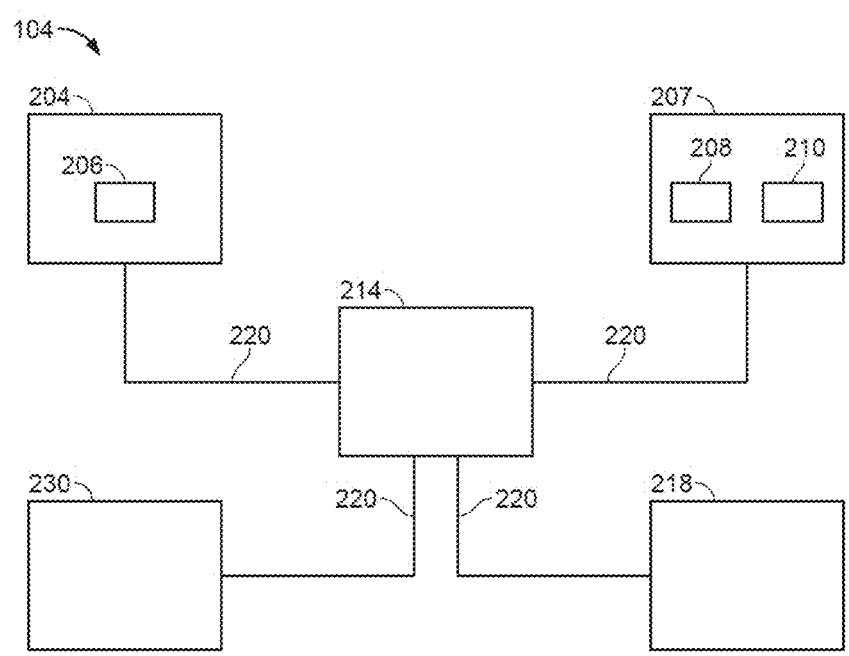
FIG. 2 is a block diagram of an exemplary computing device of the system shown in FIG. 1.

FIG. 2 is a block diagram of computing device 104. In the exemplary embodiment, computing device 104 includes a user interface 204 that receives at least one input from a user, such as an operator of sensing system 102 (shown in FIG. 1). User interface 204 may include a keyboard 206 that enables the user to input pertinent information. User interface 204 may also include, for example, a pointing device, a mouse, a stylus, a touch sensitive panel (e.g., a touch pad, a touch screen), a gyroscope, an accelerometer, a position detector, and/or an audio input interface (e.g., including a microphone).

Moreover, in the exemplary embodiment, computing device 104 includes a presentation interface 207 that presents information, such as input events and/or validation results, to the user. Presentation interface 207 may also include a display adapter 208 that is coupled to at least one display device 210. More specifically, in the exemplary embodiment, display device 210 may be a visual display device, such as a cathode ray tube (CRT), a liquid crystal display (LCD), an organic LED (OLED) display, and/or an "electronic ink" display. Alternatively, presentation interface 207 may include an audio output device (e.g., an audio adapter and/or a speaker) and/or a printer.

Computing device 104 also includes a processor 214 and a memory device 218. Processor 214 is coupled to user interface 204, presentation interface 207, and to memory device 218 via a system bus 220. In the exemplary embodiment, processor 214 communicates with the user, such as by prompting the user via presentation interface 207 and/or by receiving user inputs via user interface 204. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 218 includes one or more devices that enable information, such as executable instructions and/or other data, to be stored and retrieved. Moreover, memory device 218 includes one or more computer readable media, such as, without limitation, dynamic random access memory (DRAM), static random access memory (SRAM), a solid state disk, and/or a hard disk. In the exemplary embodiment, memory device 218 stores, without limitation, application source code, application object code, configuration data, additional input events, application states, assertion statements, validation results, and/or any other type of data. Computing device 104, in the exemplary embodiment, may also include a communication interface 230 that is coupled to processor 214 via system bus 220. Moreover, communication interface 230 is communicatively coupled to sensing system 102 and to data management system 108 (shown in FIG. 1).

In the exemplary embodiment, processor 214 may be programmed by encoding an operation using one or more executable instructions and providing the executable instructions in memory device 218. In the exemplary embodiment, processor 214 is programmed to select a plurality of measurements that are received from sensing system 102 of brain activity that is representative of at least one parameter of the brain of the subject during a resting state. The plurality of measurements may include, for example, a plurality of voxels of at least one image of the subject's brain, wherein the image may be generated by processor 214 within computing device 104. The image may also be generated by an imaging device (not shown) that may be coupled to computing device 104 and sensing system 102, wherein the imaging device may generate the image based on the data received from sensing system 102 and then the imaging device may transmit the image to computing device 104 for storage within memory device 218. Alternatively, the plurality of measurements may include any other type measurement of brain activity that enables system 100 to function as described herein.

Processor 214 may also be programmed to perform a correlation analysis. More specifically, in the exemplary embodiment, processor 214 may be programmed to compare at least one data point from each of the plurality of measurements with a corresponding data point from a previously acquired data set from at least one other subject. For example, processor 214 may be programmed to compare a resting state data point from each selected voxel from an image of the subject with a corresponding data point that is located within the same voxel of the previously acquired data set of the other subject. Processor 214 may also be programmed to produce at least one map (not shown in FIG. 2) of the brain of the subject, such as a functional connectivity map, for each of the plurality measurements. The map is based on the comparison of the resting state data point and the corresponding previously acquired data point. The map, for example, may illustrate the location within the brain of a measured brain activity. Processor 214 may be programmed to produce the map by using the various compared data points in a known algorithm to calculate a plurality of outputs, such as, for example, at least one output vector. One algorithm that may be used is represented in Equation 1 below.

$$input_1 = \tanh^{-1}\left(\left[\frac{\ln(1/output-1)}{-a}\right] \cdot \frac{pinv(Weights_{hidden\text{-}output})}{a}\right) \cdot \frac{pinv(Weights_{input\text{-}hidden})}{b}$$ (Eqn. 1)

In Equation 1, a and b represent activating function parameters. The output represents a seven dimensional output vector and pinv represents a pseudo inverse function.

Processor 214 may also be programmed to categorize or classify the measured brain activity in a plurality of networks in the brain based on the map. For example, processor 214 may be programmed to categorize the measured brain activity to a particular neural network of the brain of the subject based on the location of the measured brain activity on the map of the subject's brain.

During operation, as the subject is in a resting state, sensing system 102 detects a plurality of measurements of brain activity that is representative of at least one parameter of the brain of the subject. Sensing system 102 transmits at least one signal representative of the measurements to computing device 104 via data conduit 106. More specifically, the signals are transmitted to and received by communication interface 230 within computing device 104. Communication interface 230 then transmits the signals to processor 214 for processing and/or to memory device 218, wherein the data may be stored and transmitted to processor 214 at a later time. Processor 214 may generate an image of the plurality of measurements. Alternatively, sensing system 102 may transmit the signals to an imaging device (not shown), wherein an image of the measurements may be generated. The image may then be transmitted to computing device 104, wherein the image is stored within memory device 218 and transmitted to processor 214 for processing.

Moreover, data of other subjects may be transmitted to computing device 104 from database 110 (shown in FIG. 1) via network 109 (shown in FIG. 1). More specifically, the data may be received by communication interface 230 and then transmitted to processor 214 for processing and/or to memory device 218, wherein the data may be stored and transmitted to processor 214 at a later time. Computing device 104 may obtain the data at any time during operation.

In the exemplary embodiment, computing device 104 produces at least one map for each of the plurality of measurements received. More specifically, processor 214 first selects each of the plurality of measurements, received from sensing system 102. For example, in the exemplary embodiment, processor 214 selects each of the voxels from the image. Alternatively, processor 214 may select any other types of measurements for brain activity that enables system 100 to function as described herein. Moreover, a user may see the image on the computing device 104, via presentation interface 207, and select the measurements, such as voxels, via user interface 204.

When each of the measurements has been selected, processor 214 then performs a correlation analysis. More specifically, processor 214 compares at least one data point from each of the selected measurements with a corresponding data point from a previously acquired data set from at least one other subject, wherein computing device 104 obtained the data set from database 110. For example, processor 214 may compare at least one resting state data point from each selected voxel of the image of the subject with a data point that is located within the same voxel of the previously acquired data set of at least one other subject.

When processor 214 has completed the correlation analysis, processor 214 then produces at least one map (not shown in FIG. 2) of the brain of the subject, such as a functional connectivity map, for each of the measurements. More specifically, processor 214 produces a map of the brain of the subject based on each of the comparisons of each of the resting state data points and the corresponding previously acquired data points. The map, for example, may illustrate the location within the brain of a measured brain activity. Processor 214 then categorizes or classifies the measured brain activity in a plurality of networks in the brain based on the map. For example, based on the location of the measured brain activity in the map, processor 214 categorizes the measured brain activity to a particular neural network of the brain of the subject. The map may be presented to the user via presentation interface 207. Moreover, a textual representation and/or a graphical output for the various categorizations may also be presented to the user via presentation interface 207.

Figure 3:
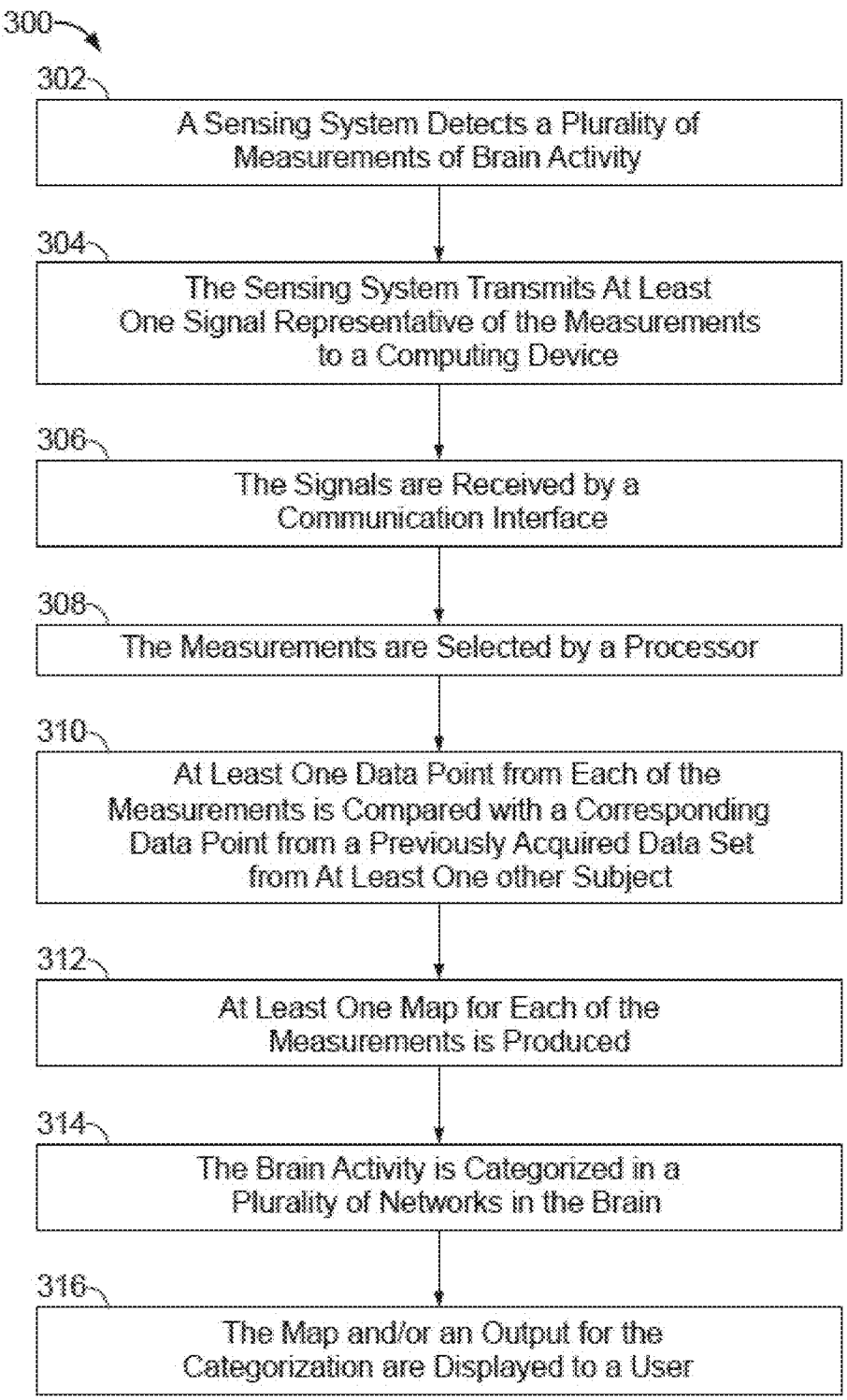
FIG. 3 is flow diagram of an exemplary method for task-less mapping of brain activity using the system shown in FIG. 1.

FIG. 3 is flow diagram of an exemplary method 300 for task-less mapping of brain activity of a brain of a subject using system 100 (shown in FIG. 1). A sensing system 102 (shown in FIG. 1) detects 302 a plurality of measurements of brain activity that is representative of at least one parameter of the brain of the subject during a resting state. Sensing system 102 transmits 304 at least one signal representative of the measurements to a computing device 104 (shown in FIGS. 1 and 2). The signals are received 306 by a communication interface 230 (shown in FIG. 2). The measurements are selected 308 by a processor 214 (shown in FIG. 2). At least one data point from each of the measurements is compared 310 with a corresponding data point from a previously acquired data set from at least one other subject.

At least one map for each of the measurements is produced 312 based on the comparison of the resting state data point and the corresponding previously acquired data point. The brain activity is categorized 314 in a plurality of networks in the brain based on the map. The map and/or an output for the categorization are displayed 316 to a user, via a presentation interface 207 (shown in FIG. 2).

The embodiments of the system and method for task-less mapping of brain activity using resting state data of a brain of a subject, as described herein, were used in the following exemplary experiment.

In the exemplary experiment, perceptron training and testing used previously acquired data sets. All patients were young adults screened to exclude neurological impairment and psychotropic medications. Demographic information and acquisition parameters are given in Table 1 below.

TABLE 1

Characteristics of the training test and validation data sets.

| Dataset | Training | Optimization (Test) | Validation |
| --- | --- | --- | --- |
| Number of Subjects | 21 (7M + 14 F) | 17 (8M + 9F) | 10 (4M + 6F) |
| Age | 27.6 (23-35) years | 23.1 (18-27) years | 23.3 ± 3 years |
| Number of frames | 128 × 6 runs | 194 × 4 runs | 100 × 9 runs |
| TR (s) | 2.16 | 2.16 | 3.03* |

*The TR in the validation data set includes a one second pause between frames to accommodate simultaneous EEG recording.

In the exemplary experiment, all imaging was performed with a 3T Allegra scanner. Functional images were acquired using a BOLD contrast sensitive gradient echo echo-planar sequence [FOV=256 mm, flip angle=90°, 4 mm3 voxels, other parameters listed in Table 1] during which subjects were instructed to fixate on a visual cross-hair, remain still, and not fall asleep. Anatomical imaging included one sagittal T1-weighted magnetization prepared rapid gradient echo (MP-RAGE) scan (T1 W) and one T2-weighted scan (T2 W).

Initial fMRI preprocessing followed conventional practice known in the art. This included compensation for slice-dependent time shifts, elimination of systematic odd-even slice intensity differences due to interleaved acquisition, and rigid body correction for head movement within and across runs. Atlas transformation was achieved by composition of affine transforms connecting the fMRI volumes with the T2 W and T1 W structural images. Head movement correction was included with the atlas transformation in a single resampling that generated volumetric time series in 3 mm3 atlas space. Additional preprocessing in preparation for correlation mapping included spatial smoothing enabled using 6 mm FWHM Gaussian blur in each direction, voxel-wise removal of linear trends over each fMRI run, and temporal low-pass filtering that enabled the retaining of frequencies below 0.1 Hz.

Spurious variance was reduced by regression of nuisance waveforms derived from head motion correction and time series extracted from regions (of "non-interest") in white matter and CSF. Nuisance regressors included also the BOLD time series averaged over the brain, i.e., global signal regression (GSR). Thus, all computed correlations were effectively order 1 partial correlations controlling for variance shared across the brain. GSR has been criticized on the grounds that it artificially generates anticorrelations. However, GSR fits well as a step preceding principal component analysis because it generates approximately zero-centered correlation distributions. As well, GSR enhances the spatial specificity in subcortical seed regions and reduces structured noise. The question of whether the left tail of a zero-centered correlation distribution ("anticorrelations") is "false" or "tenuously interpretable" is irrelevant in the context of RSN classification.

Correlation maps were computed using standard seed-based procedures, i.e., by correlating the time series averaged over all voxels within the seed (generally, 5 mm spheres) against all other voxels, excluding the first 5 (pre-magnetization steady-state) frames of each fMRI run. Frame-censoring was employed with a threshold of 0.5% RMS frame-to-frame intensity change. Frame-censoring excluded 3.8±1.1% of all magnetization steady-state frames from the correlation mapping computations. Correlation maps were Fisher z-transformed prior to further analyses.

In the exemplary embodiment, cortical reconstruction and volume segmentation were performed using FreeSurfer. Adequate segmentation was verified by inspection of the FreeSurfer-generated results in each of the 21 training and 17 test datasets. Cortical and subcortical gray matter regions were selected from these segmentations, thresholded to obtain a conjunction of 30% of subjects, and then masked with an image of the average BOLD signal intensity across all subjects, thresholded at 80% of the mode value. This last step removes from consideration brain areas in which the BOLD signal is unreliable because of susceptibility artifacts. The resulting 30,981 voxels constituted the grey matter mask. This mask was applied to all correlation maps input to the classifier. Individual surfaces were deformed to a common space, producing consistent assignment of surface vertex indices with respect to gyral features across subjects. Final volumetric results for each subject were sampled onto surface vertices by cubic spline interpolation onto mid-thickness cortical surface coordinates.

Seed regions were generated by meta-analyses of task-fMRI studies. Task-response foci were initially assigned to one of 10 functional networks in Table 2 below. Each task fMRI study contributed a variable number of foci (Task ROIs column in Table 2). Task foci were used as seeds to generate correlation maps in all 21 subjects in the training set. These maps then were entered into random effects analyses (against the null hypothesis of no correlation) to produce Gaussianized t-statistic (Z-score) images. Z-score images representing seeds assigned to the same RSN were averaged. Additionally, a conjunction image representing at least 70% of random effects images for a given network (after thresholding at |Z|>3) was produced. Averaged Z-score images were masked to include only voxels contained in the conjunction. Peaks of the conjunction-masked average were selected as center coordinates for 6 mm spherical ROIs. Accordingly, the constraint employed was that all ROIs within a given network must be separated by at least 12 mm. This process resulted in a large set of ROIs that were operationally treated as provisional.

TABLE 2

Studies of functional co-activation used to generate seed ROIs.

| RSN | Task paradigm | fMRI contrast | Task ROIs | Provisional seed ROIs | Final seed ROIs |
|---|---|---|---|---|---|
| DAN | 1. Rapid Serial Visual Presentation (RSVP) 2. Rapid Serial Visual Presentation (RSVP) 3. Posner Cueing Task | 1. Cue Type × event time 2. Cue location × cue type × event time 3. Event time | 10 | 28 | 28 |
| VAN | Posner Cueing Task | Invalid vs. Valid | 2 | 19 | 15 |
| CO* | Mixed design (10 different tasks) | Graph theoretic analysis* | N/A | 7 | |
| SMN | Posner Cueing Task | Target Period | 11 | 37 | 39 |
| AN | Various auditory stimuli | Stimulation vs. control | 2 | 12 | |
| VIS | Visual Localizer | Peripheral Foveal | 8 2 | 19 12 | 30 |
| FPC* | Mixed design (10 different tasks) | Graph theoretic analysis* | N/A | 11 | 12 |
| LAN | Perceptual vs. Episodic Memory Search Paradigm | Sentence Reading | 13 | 17 | 13 |
| DMN | Perceptual vs. Episodic Memory Search Paradigm | Memory Retrieval | 4 | 42 | 32 |

*Regions reported were themselves the result of a meta-analysis followed by refinement. Hence, these seeds were directly used as provisional ROIs.

In the exemplary embodiment, the provisional ROI set was iteratively refined by maximizing the spatial concordance between the correlation map obtained from each seed and the map obtained by pooling all seeds within the RSN to which the seed was assigned. Pooled seed correlation maps were computed by averaging the time series across all seeds assigned to each RSN. The single seed and the pooled seed maps were averaged across subjects. RSN concordance was assessed as the spatial correlation between the (subject-averaged) single seed and the (subject-averaged) pooled seed maps. Seeds were considered outliers if their concordance estimate was less than 1.5 times the inter-quartile range below the median of all other seeds in the RSN. Outlier seeds were reassigned to the RSN of greatest concordance, unless they were maximally concordant with the currently assigned RSN, in which case they were removed entirely. After reassignment and outlier rejection, new individual seed and pooled seed correlation maps were re-computed and the process was iterated. Convergence (no reassignments or outlier rejections) was achieved in 7 iterations. The cingulo-opercular (CO) network did not survive iterative refinement, and most seeds were reassigned to the ventral attention network or removed. Similarly, the auditory network was subsumed into the sensorimotor network and the originally distinct foveal and peripheral visual networks were combined into a single (VIS) network.

Figure 4:
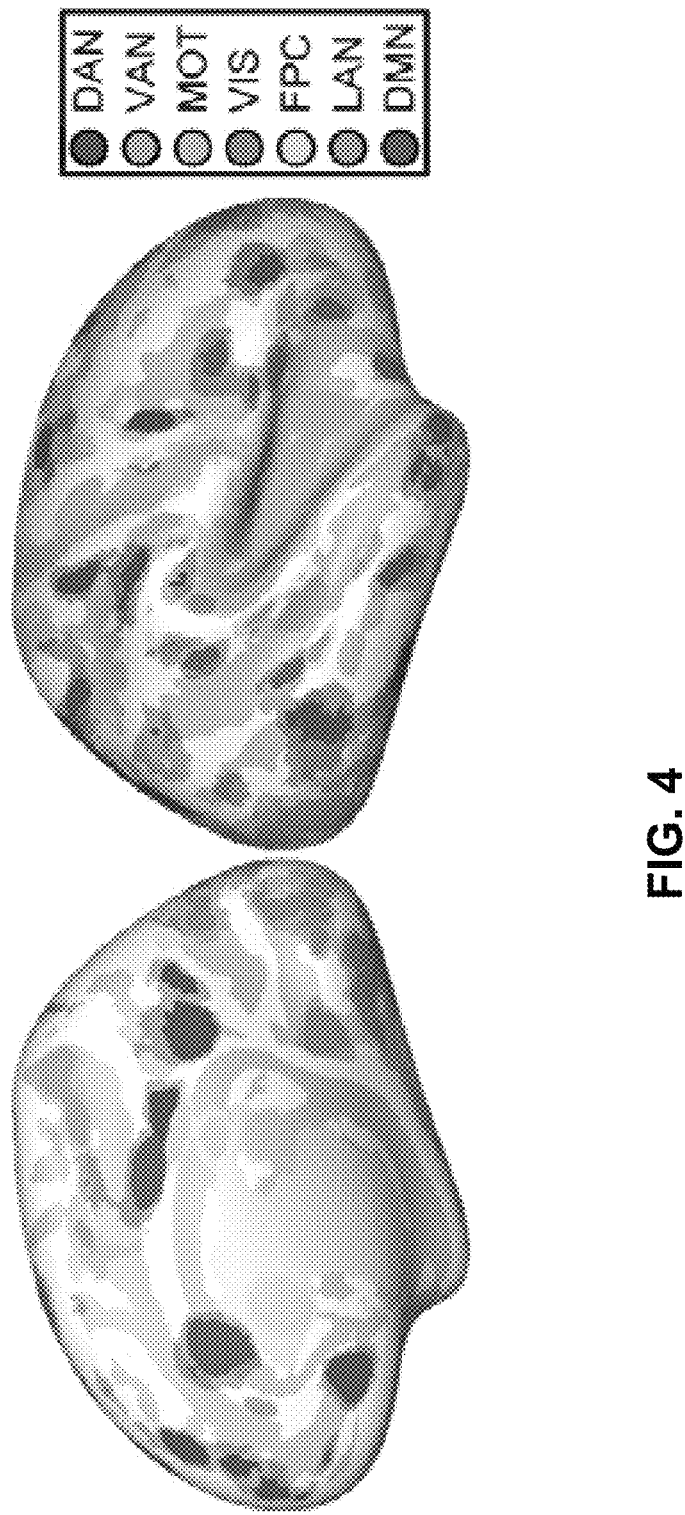
FIG. 4 is an image of seed ROIs for generation of correlation map data.
Figure 15:
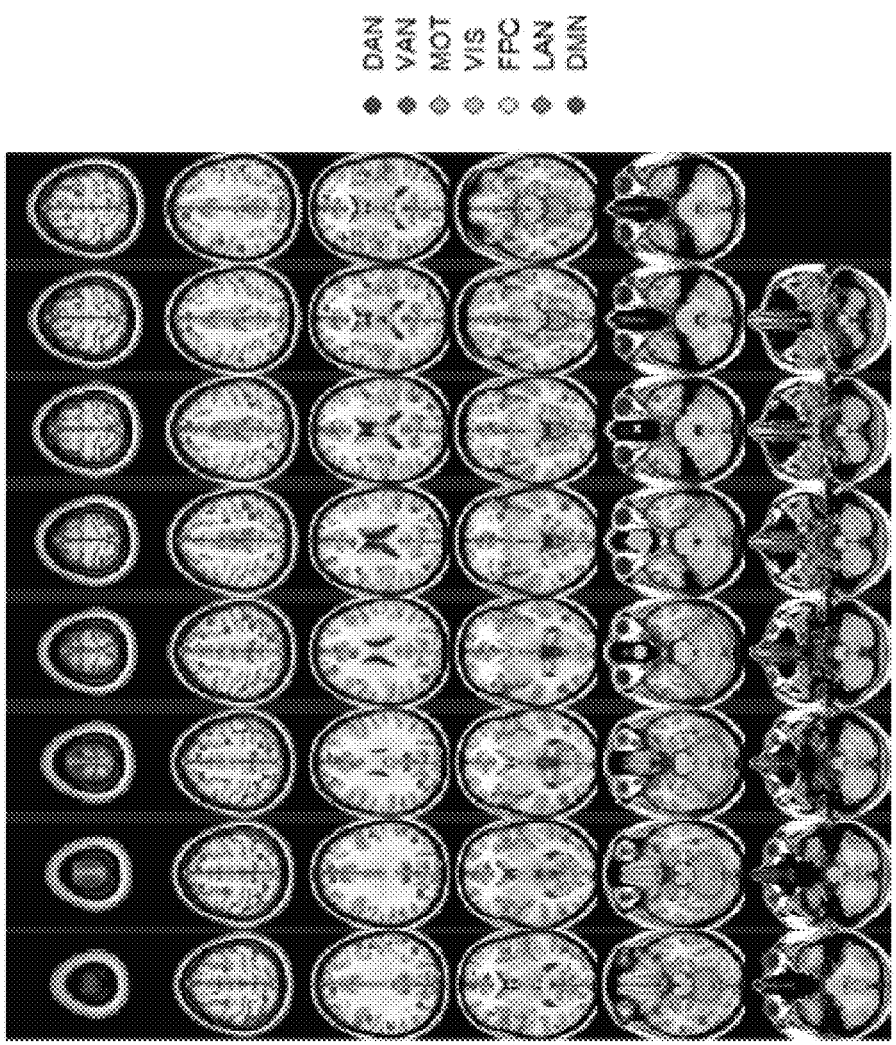
FIG. 15 is a scan of voxels.

Iterative refinement yielded 169 ROIs representing 7 RSNs with high intra- and low inter-network correlation, as shown in FIGS. 4 and 15. To these were added a nuisance category consisting of 6 ROIs in CSF spaces. The latter enabled the classifier to separate correlation patterns representing CSF vs. true RSNs. Computing correlation maps for each of the 175 seed regions in all 21 training subjects produced 3,675 images that were used as training data. Each image in the training set was masked to include only grey matter voxels, producing a 3,675×30,981 matrix. Similarly, 175·17=2,975 images were computed in the test data set. Each image was assigned to one RSN (see the description of iterative seed ROI refinement above and Table 2).

A multilayer perceptron was constructed to classify resting-state fMRI correlation maps into 7 canonical spatial patterns predefined as resting-state networks. The core of the perceptron is an artificial neural network that includes an input, hidden, and output layer, each consisting of some number of nodes fully connecting to the next layer (all-to-all feed-forward). Training samples (correlation maps from a particular seed and subject) are passed into this feed-forward network and the output is compared to the correct RSN label, as specified in the fMRI task meta-analysis. The error in this comparison is used to update the connections, or weights, between layers to increase the performance of the classifier.

As an initial pre-processing step, the dimensionality of the input data was reduced by using principal component analysis (PCA). Representing correlation maps in terms of eigenvectors provides efficient computation, well-conditioned weight matrices, and a free parameter to represent the complexity of the input data (number of PCs). PCA was performed on the matrix of masked correlation images (21 subjects×175 seeds=3,675 images×30,981 voxels for PCA). Each correlation map in the training (3,675 images) and the test (2,975 images) data sets were then represented using a variable number of principal components (PCs).

Figure 5:
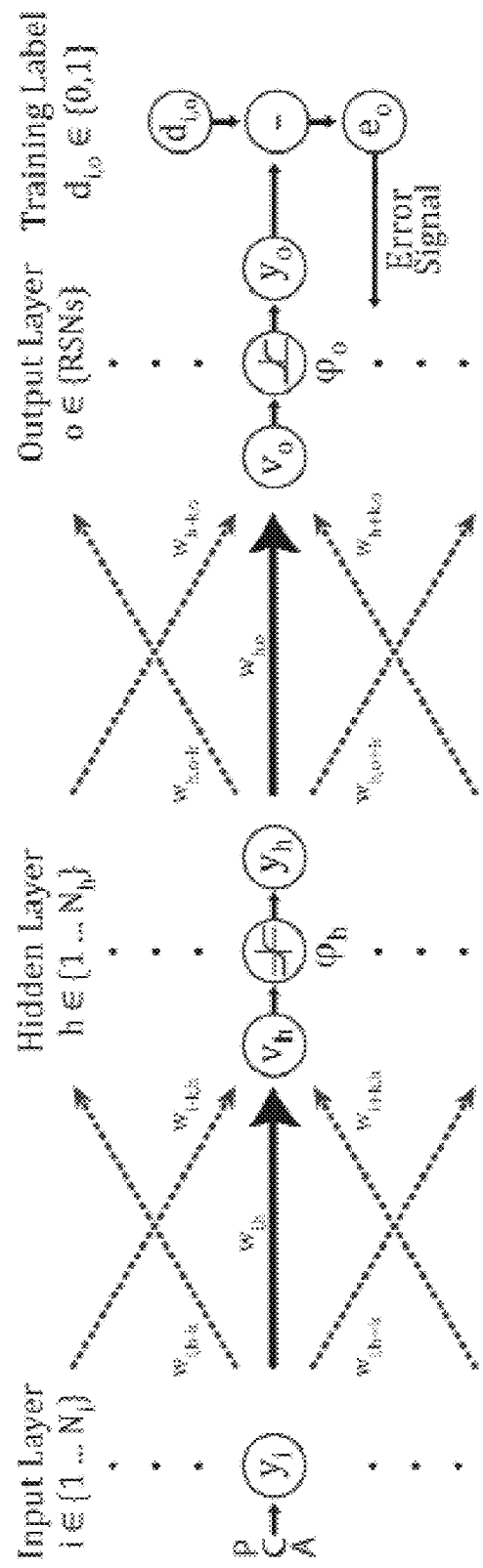
FIG. 5 is a schematic of an exemplary standard multi-layer perceptron architecture and the associated transfer function of the perceptron.

The input layer received the correlation map training data as vectors in PCA space (the value of a given correlation map projected along a particular PC). Thus, the number of input nodes was a free parameter that depended on the number of PCs used to represent the data. Each training example (a correlation map from a particular seed ROI/subject pair) was associated with a desired output value, $d_o$ (Eqn. (7)), corresponding to the a priori RSN labels. The goal of the training process is to compare the output to these desired values, thereby generating an error signal used to update connection weights. The overall transfer function of the perceptron (Eqn. (2)) corresponds to the detailed schematic of the propagation of inputs through the perceptron (FIG. 5, see legend for symbol definitions).

$$y_o = \varphi_o\left(\sum_h w_{ho}(\eta) \cdot \varphi_h\left(\sum_i w_{ih} \cdot y_i\right)\right) \quad (2)$$

The total input to each hidden node, $v_h$, is determined by the sum of all input nodes, weighted by the feed-forward connections (Eqn. (3)). This sum is then transformed by the hidden layer activation function to compute the output value of the hidden layer node, $y_h$ (Eqn. (4)).

$$v_h = \sum_i w_{ih} \cdot y_i \tag{3}$$

$$y_h = \varphi_h(v_h) = a \cdot \tanh(b \cdot v_h) \tag{4}$$

The output layer nodes operate in the same manner as hidden layer nodes (Eqns. (5) and (6)):

$$v_o(n) = \sum_i w_{ho}(n) \cdot y_h(n) \tag{5}$$

$$y_o = \varphi_o(v_o) = \frac{1}{1 + e^{-a \cdot v_o}} \tag{6}$$

After propagation of the input data through the perceptron, the output value for each node, $y_o$, was compared to the desired value, $d_o$, to find the error, $e_o$ (Eqn. (7)).

$$e_o(k) = d(k) - y_o(k) \tag{7}$$

The local gradient of the error at an output node is found by the product of this error and the inverse of the activating function applied to the output value:

$$\delta_o = e_o \cdot \varphi'_o(v_o) \tag{8}$$

where the prime notation indicates the first derivative. After every iteration (n), the weights for the hidden to output layer connections were adjusted in the direction opposite of the gradient of the error:

$$w_{ho}(k+1) = w_{ho}(k) + \eta(k) \cdot \delta_o(k) \cdot y_h(k) \tag{9}$$

where $\eta$ is the learning rate, $y_h$ is the value of hidden layer node h, and $\delta_o$ is local error gradient at output node o. Similarly, the weights to the hidden layer from the input layer, $w_{ih}$, are adjusted according to Eqn. (10).

$$w_{ih}(k+1) = w_{ih}(k) + \eta(k) \cdot \delta_h(k) \cdot y_i(k) \tag{10}$$

The local gradient at a hidden node, $\delta_h$, may be computed by back-propagation from the output layer.

$$\delta_h = -\frac{dE}{d\gamma_h} = \varphi'_h(v_h) \cdot \sum_o \delta_o \cdot w_{ho} \tag{11}$$

Figure 6:
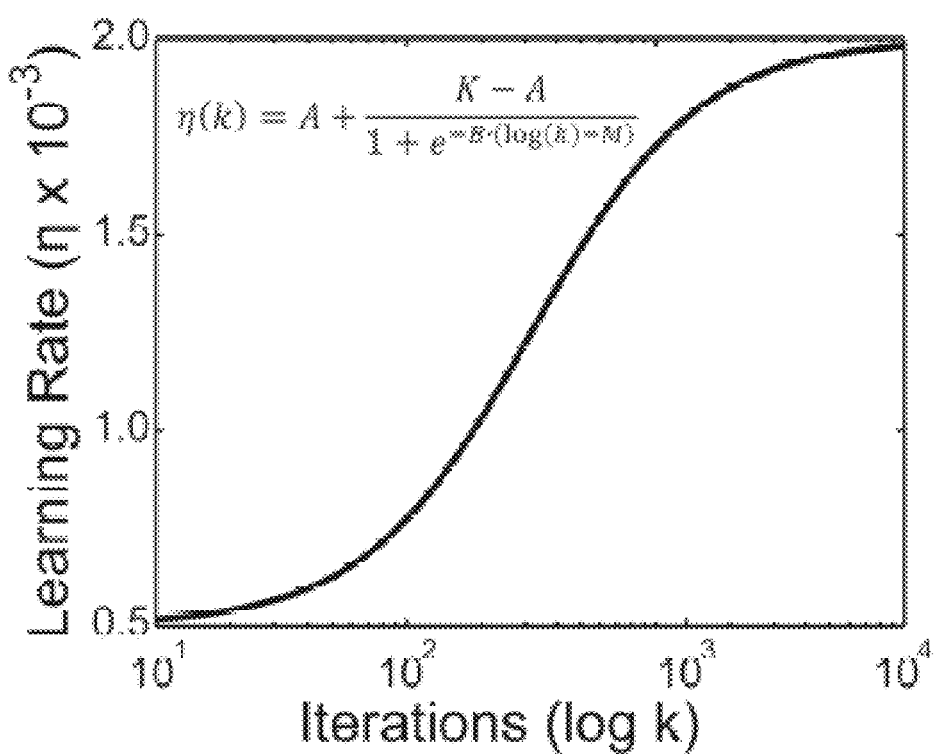
FIG. 6 is a graph of a learning rate.

The learning rate parameter, $\eta$, was set empirically. A range of stable values was determined for a constant $\eta$, where instability was noted as divergence or rapid oscillation of classifier weights. The present results were obtained using an adaptive learning rate that increased as a sigmoid in log iteration index (FIG. 6). The initial learning rate was small ($\eta(0) = A = 5 \cdot 10^{-4}$) to allow the classifier to begin a gentle descent in error gradient towards a stable solution. The learning rate increased exponentially (B=−3, Q=0.5), until saturating at an empirically determined upper limit of stability to ($\eta(\infty) = 2 \cdot 10^{-3}$).

Separation of classes was quantified using receiver operator characteristic analysis. Across a range of thresholds, the proportion of within-class output values above the threshold (true positive fraction, TPF) was compared to the number of out-of-class values above the threshold (false positive fraction, FPF). The TPF as a function of FPF defines the ROC curve. The area under the ROC curve (AUC) was used as a summary statistic of classification performance for each RSN class.

Figure 9A:
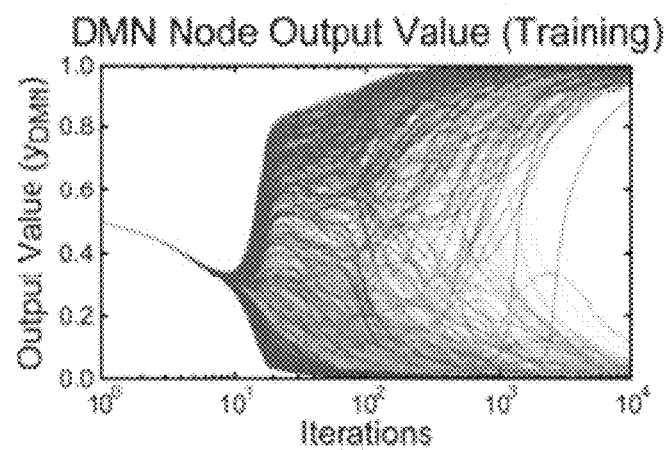
FIGS. 9A-9F are graphs depicting performance levels.
Figure 9B:
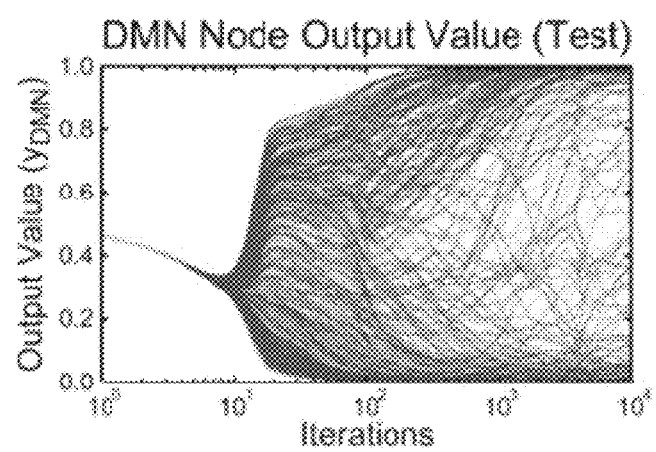
Figure 9C:
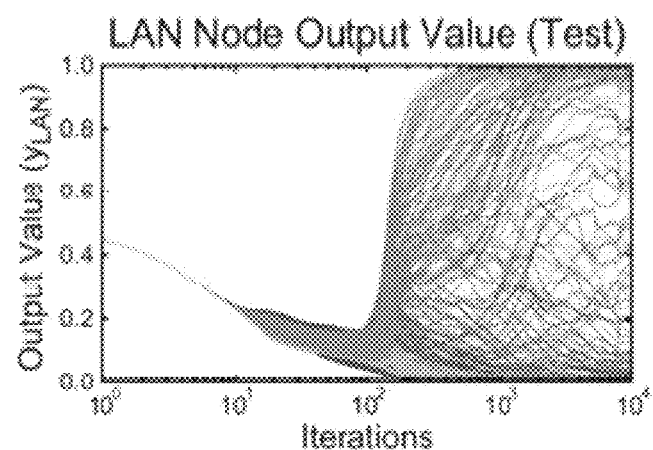
Figure 9D:
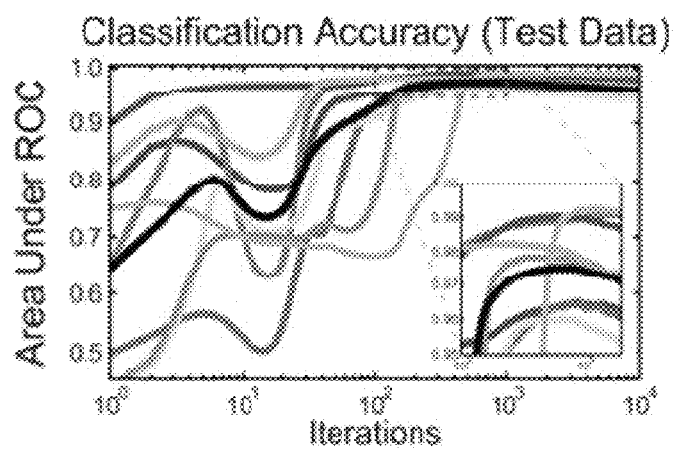

At logarithmically spaced intervals during the training process, training was paused and AUCs were calculated in a separate test data set. This procedure produced training trajectories indicating the relative performance for each RSN (FIG. 9D) throughout the training process. Peak performance for a given RSN was defined at the iteration producing the maximum AUC value in the test data (FIG. 9D). Overall performance was calculated as the average of AUC values across networks (FIG. 9D).

Figure 10:
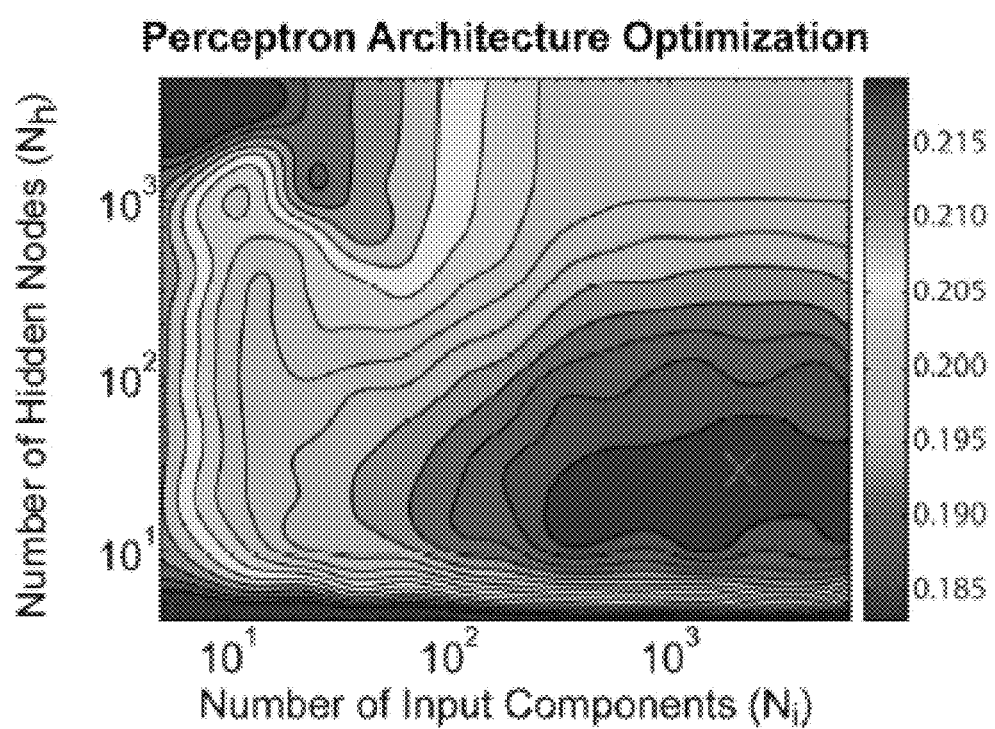
FIG. 10 is a graph depicting search space for perceptron architecture.

In the exemplary embodiment, the number of PCs sampled ($N_i$) and the number of nodes in the hidden layer ($N_h$) constitute hyper-parameters subject to optimization. Overall RMS error was evaluated over a densely sampled $N_i \in [5, 6600] \times N_h \in [4, 5000]$ space. For each ($N_i$, $N_h$) coordinate, a classifier was trained until test set error reached a minimum. The architecture with the least error (minimum of eight repetitions for each coordinate) was selected (FIG. 10).

After identifying the architecture with least error in the test data set, performance was further optimized by simulated annealing, countering the tendency of perceptrons to become trapped in local minima. Mimicking the random movement of atoms aligning in cooling metal, simulated annealing uses random perturbations of model parameters to find the global extremum in an objective function. Perturbations of steadily decreasing size (specified by a 'cooling profile') are guaranteed to find a global minimum with slow enough cooling, although, in practice, the necessary cooling profile is prohibitively slow. After training the perceptron until a minimum in RMS test set error, every weight, {wih} and {who}, was multiplied by a random coefficient. Training was then resumed to find a new minimum. If lower error was achieved, the new weights were accepted. This process was then repeated.

The value for each weight was determined by first sampling from a uniform distribution, $x \in [-1, 1]$, transformed by a hyperbolic function, $N = (1-x)/(1+x)$. Thus each weight was multiplied by $N \in [0, \infty]$, and was thus unchanged when $x = 0$. The range sampled within x determined the amount of noise injected into the system, using values closer to zero over the course of cooling. The maximum value of x was determined by the temperature, T, and the minimum value was determined so that the mean squared value of N was unity:

$$\frac{1}{T-a} \int_a^T \left(\frac{x-1}{x+1}\right)^2 dx = 1 \tag{12}$$

This choice of noise ensured that the sum of squares of the connection weights was unaltered by perturbation and that most weights were decreased, while a small selection was sporadically increased. A geometric cooling function (Eqn. (13)) was used, which decreased over $K_1$ perturbation epochs; this entire annealing process was repeated $K_2$ times, each time with a slightly cooler temperature profile.

$$T_{k_1, k_2} = T_0 \cdot r^{(k_1 + 3k_2)} \tag{13}$$

Figure 7:
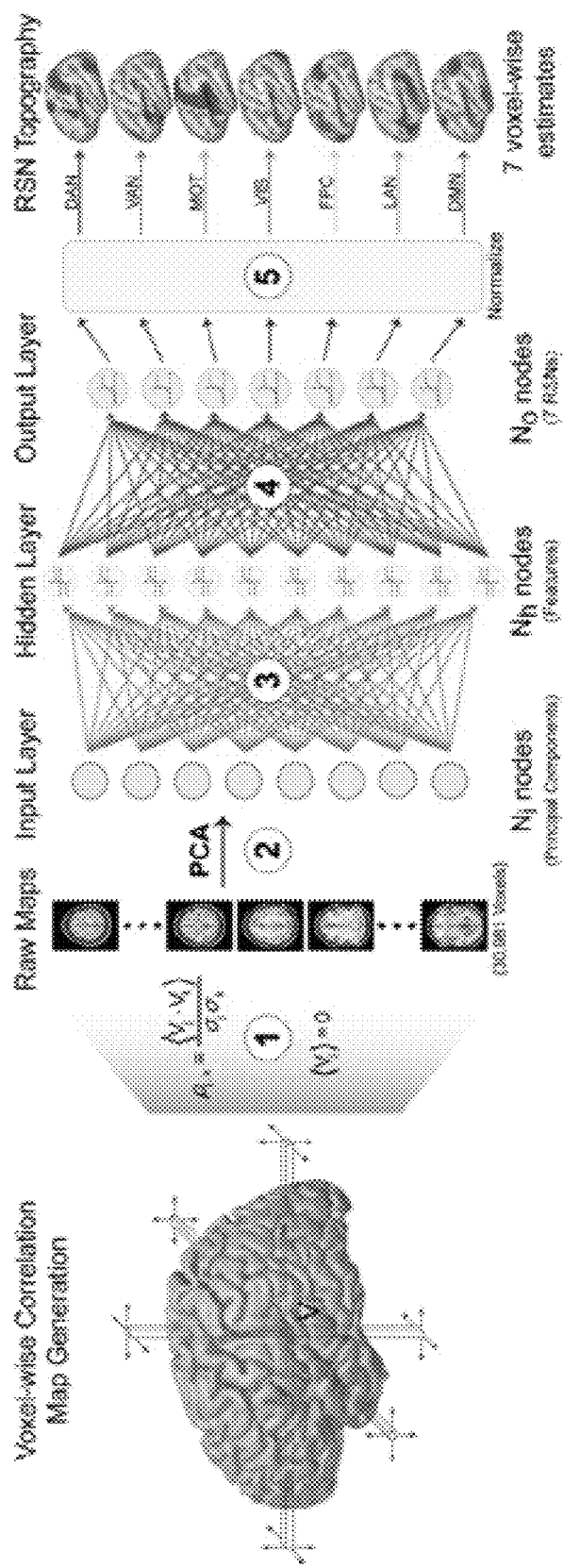
FIG. 7 is a schematic of a voxel-wise classification.

The following parameters were used: r=0.95, $T_0$=0.4, $K_1$=40, $K_2$=20. To map RSNs in individual subjects, a correlation map was generated for every voxel in the brain and then classified using the trained and optimized perceptron. An overall schematic of this process is depicted in FIG. 10. A correlation map was produced for every point in the brain by correlating every voxel's BOLD time-course with every other voxel in the brain. Each map was masked before classification to include only grey matter voxels producing a 65,549 (voxels within brain mask)×30,981 (voxels within grey matter mask) element matrix (FIG. 7). This data was then projected onto the eigenvectors of the training data, reducing the dimensionality to 65,549×2500 (FIG. 7). Thus, all correlation maps were represented in the same input data space for classifier training and testing. The reduced whole-brain connectivity data was then propagated through the perceptron, with the first layer reducing the data to 22 features (65,549×22; FIG. 7), and the second layer producing RSN estimates (65,549×8, FIG. 7). However, FIG. 7 depicts only 7 output classes because one of the 8 outputs is a nuisance component used only in post-processing.

Classifier output values are approximately uniformly [0,1] distributed as a result of the logistic activation function on the output layer (Eqn. (6)). Classifier values were then normalized within each voxel to sum to unity (FIG. 7). This normalization penalized voxels that had high classification values for multiple networks. The presence of a CSF classification component further penalized RSN estimates in voxels exhibiting CSF-related correlation patterns. Within each network, classifier values were then converted back to an exactly uniform [0,1] distribution across voxels (rank-order transform). This transformation resulted in voxels ranked in membership for each network across the brain expressed as a percentile.

To visualize group level results on the cortical surface, RSN topography estimates were projected to the cortical mid-thickness surface for each subject (after surface-registration across subjects). Averages were then computed across surface nodes. The standard deviation of classifier values was also calculated node-wise to illustrate regions of high variability. These group-level results were projected onto the group-average inflated surface. To visualize group level results in sub-cortical structures, classifier values were averaged voxel-wise across subjects. Group-average images were then re-sampled to 1 mm cubic voxels and overlaid on a co-registered MNI152 atlas target.

In the exemplary embodiment, spatial correlation analysis (FIG. 8B) and principal component analysis (FIG. 8C) of the training data (the correlation maps produced for each seed ROI) revealed distinct clustering corresponding to RSNs. In the map-to-map spatial correlation matrix (averaged across subjects), training inputs showed high correlation with other inputs of the same RSN compared to inputs of other classes (FIG. 8B). Additionally, the map-to-map correlation matrix showed two major clusters, one corresponding to the DAN, VAN, VIS, and MOT networks, and the other corresponding to the FPC, LAN, and DMN networks. Projection of all 3,675 correlation maps into principal component space gave rise to partially overlapping clusters corresponding to 7 RSNs. In the PC1×PC2 plane (FIG. 6), DAN (purple) and DMN (red) showed little overlap and appeared at opposite ends of the PC1 axis. MOT (light blue) and VIS (green) clusters were highly overlapping in this plane, but showed little overlap in the PC3×PC4 plane.

FIGS. 9A-9F shows the training performance for the perceptron optimized for overall performance (2500 input PCs, 22 hidden layer nodes). For every correlation map, the perceptron output node values represent an estimate of membership for each RSN. The expectation value of all initial perceptron outputs is 0.5 (FIGS. 9A-9C) as the expected output value with zero-mean weights ($v_o$) is 0 (Eqns. (5) and (6)). As training progresses, within-class output values increase towards unity (e.g., DMN output node values for DMN inputs, red traces in FIG. 9A), while out-of-class output values decrease towards zero (DMN output value for non-DMN ROI-derived maps, all other traces in FIG. 9A).

Figure 9E:
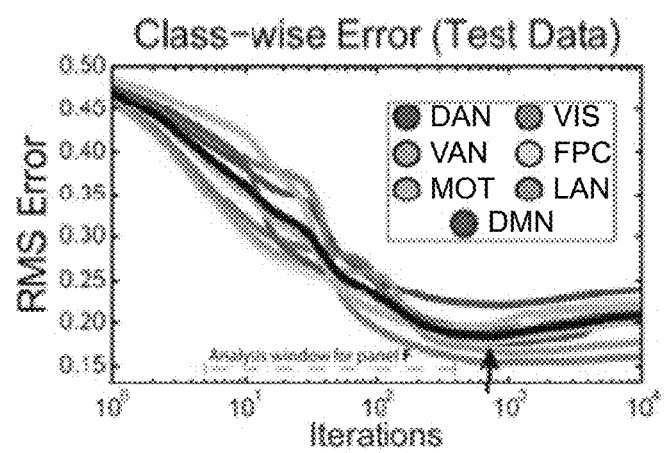
Figure 9F:
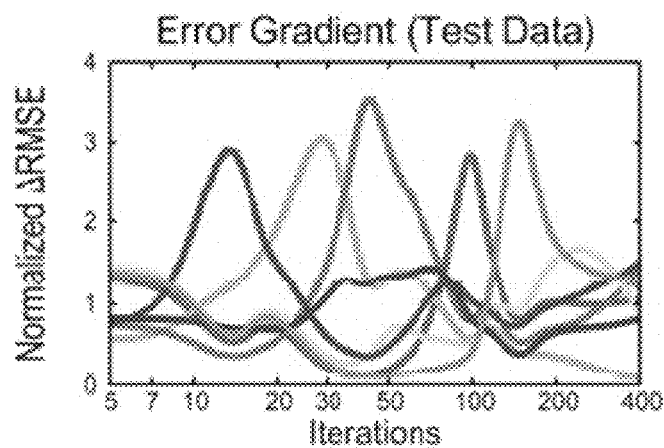

Area under the ROC curve (AUC) trajectories are shown in FIG. 9D. This quantity, averaged across RSN classes, began near chance (0.65 after one iteration) and rose in later iterations. For all networks, the AUC exhibited a transient decrement in performance early in training. This feature corresponded to transient changes of slope in RMS error but did not produce concavity (local minima) in RMS error (FIG. 9E). Class separation was achieved at varying numbers of iterations for different RSNs. Across all perceptron architectures, the default mode network (red trace) always achieved asymptotic performance earliest, and the language network (orange) latest. Asymptotic performance for CSF classification occurred much later than any true RSN. Performance on the test data initially followed training performance until reaching a global maximum (FIG. 9E). This maximum occurred at varying iteration indices for different RSNs. Training beyond this point resulted in over-fitting, manifesting as decreasing test data performance despite increasing training performance. Inputs that were previously correctly classified in the test data became incorrectly classified (FIGS. 9B and 9C).

Over a dense sampling of input and hidden layer sizes ($N_i \times N_h$), the perceptron was trained until the peak AUC could be determined (FIG. 10). The optimal overall performance for the perceptron was found at 2500 PCs and 22 hidden layer nodes (FIG. 10). The perceptron was trained with this architecture using 10 mm ROIs and the result was optimized through simulated annealing, yielding an over-all classification performance of 0.9822 (AUC) with 17.1% RMS error. The maximal AUC and minimal RMS error rates differed by network, as shown in Table 3.

TABLE 3

RSN classification performance.

| Network | Test (Optimization Set) | | Retest (Validation Set) | |
| --- | --- | --- | --- | --- |
| | Accuracy (AUC) | Error (RMS) | Accuracy (AUC) | Error (RMS) |
| DAN | 0.973 | 20.2% | 0.973 | 20.1% |
| VAN | 0.971 | 17.9% | 0.979 | 17.6% |
| SMN | 0.988 | 16.4% | 0.994 | 17.2% |
| VIS | 0.993 | 13.4% | 0.998 | 12.7% |
| FPC | 0.972 | 17.5% | 0.989 | 14.8% |
| LAN | 0.985 | 14.9% | 0.991 | 14.4% |
| DMN | 0.993 | 14.4% | 0.990 | 17.6% |
| Mean | 0.982 | 17.1% | 0.988 | 16.6% |

Figure 11A:
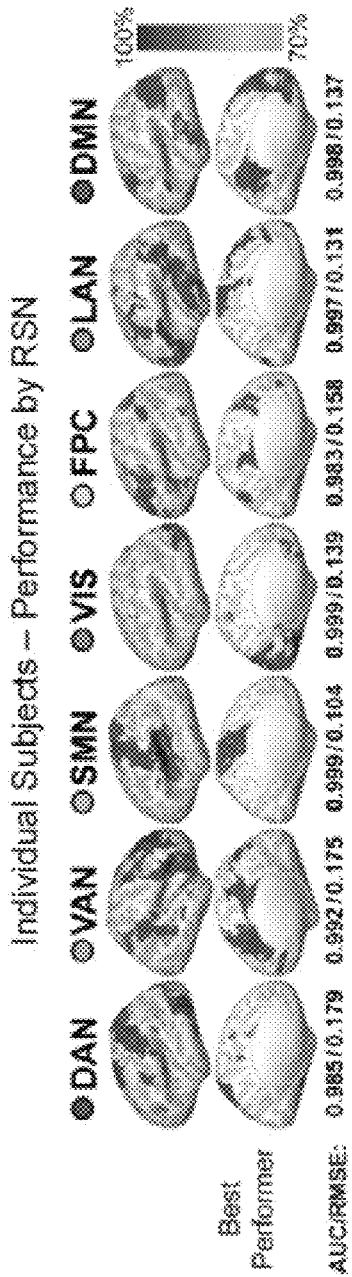
Figure 11B:
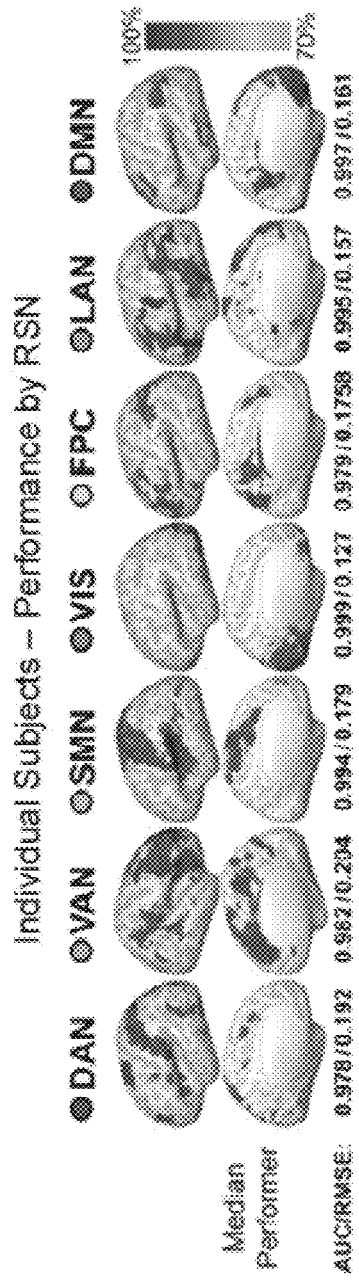

These values reflect MLP training with 10 mm radius seeds (FIGS. 14A and 14B) and optimization with simulated annealing. After completion of classifier training, voxel-wise connectivity patterns were classified in individual subjects in the test data set (FIG. 11A). RSN topography summaries were computed as winner-take-all maps (FIGS. 11A-11F and 12A-12C). Well-defined RSN topography was obtained in all subjects in the test and training groups. Specifically, the subject-wise mean and standard error of the AUC was 0.982±0.007, with the worst performing subject at 0.963. These figures corresponded to RMS error of 16.5±1.4% with the worst subject yielding 19.1%. RSNs were generally contiguous regions that conformed to previously described topography. The relationship of perceptron-defined RSNs to previous findings is discussed more fully below.

Figure 12A:
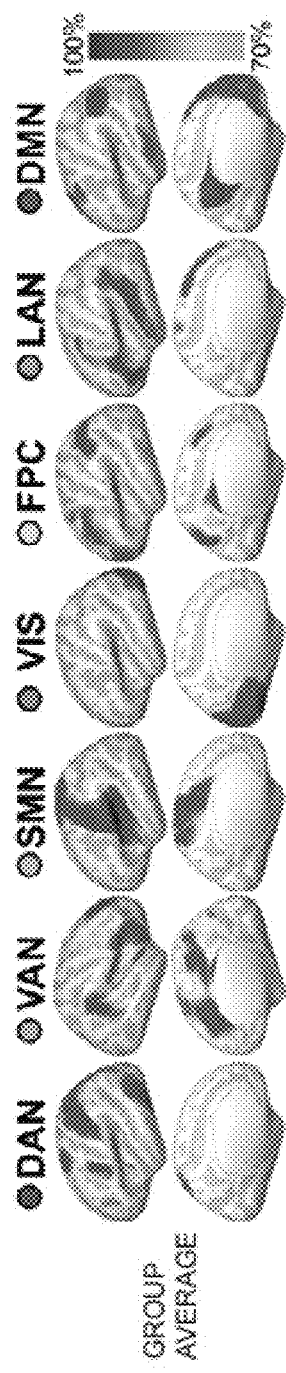
FIGS. 12A-12C are schematics of classification results.
Figure 12B:
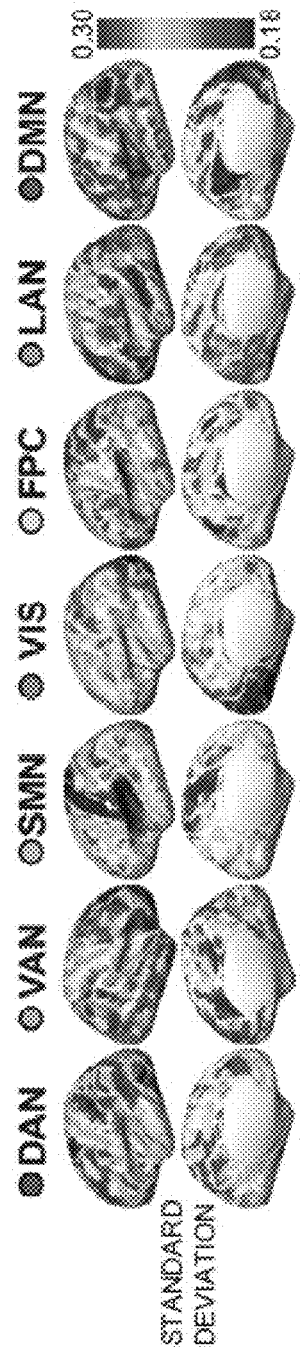
Figure 12C:
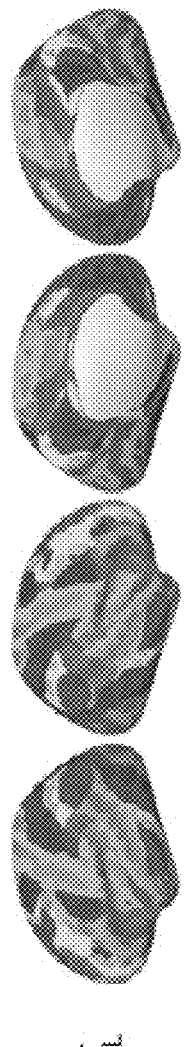

RSN topography estimates were averaged over all subjects in the training and test groups. FIGS. 12A-12C addresses both the central tendency (top row) of each group as well as inter-subject variability (middle row). Average network topographies had higher values near locations of ROIs used to generate training maps. This is expected because voxels within ROIs are likely to have similar correlation maps to the ROI. High classification values (in the top 25%) were also found in contiguous regions not used to generate training data. For example, a lateral temporal region was classified as a fronto-parietal control region, and a dorsal pre-motor region was classified into the language network. This type of result demonstrates external validity (or equivalently, generalizability) of perceptron classification, i.e., recovery of true features in RSNs not included in the training set. These features are also present in the results in individual subjects (FIG. 11A).

Figure 13:
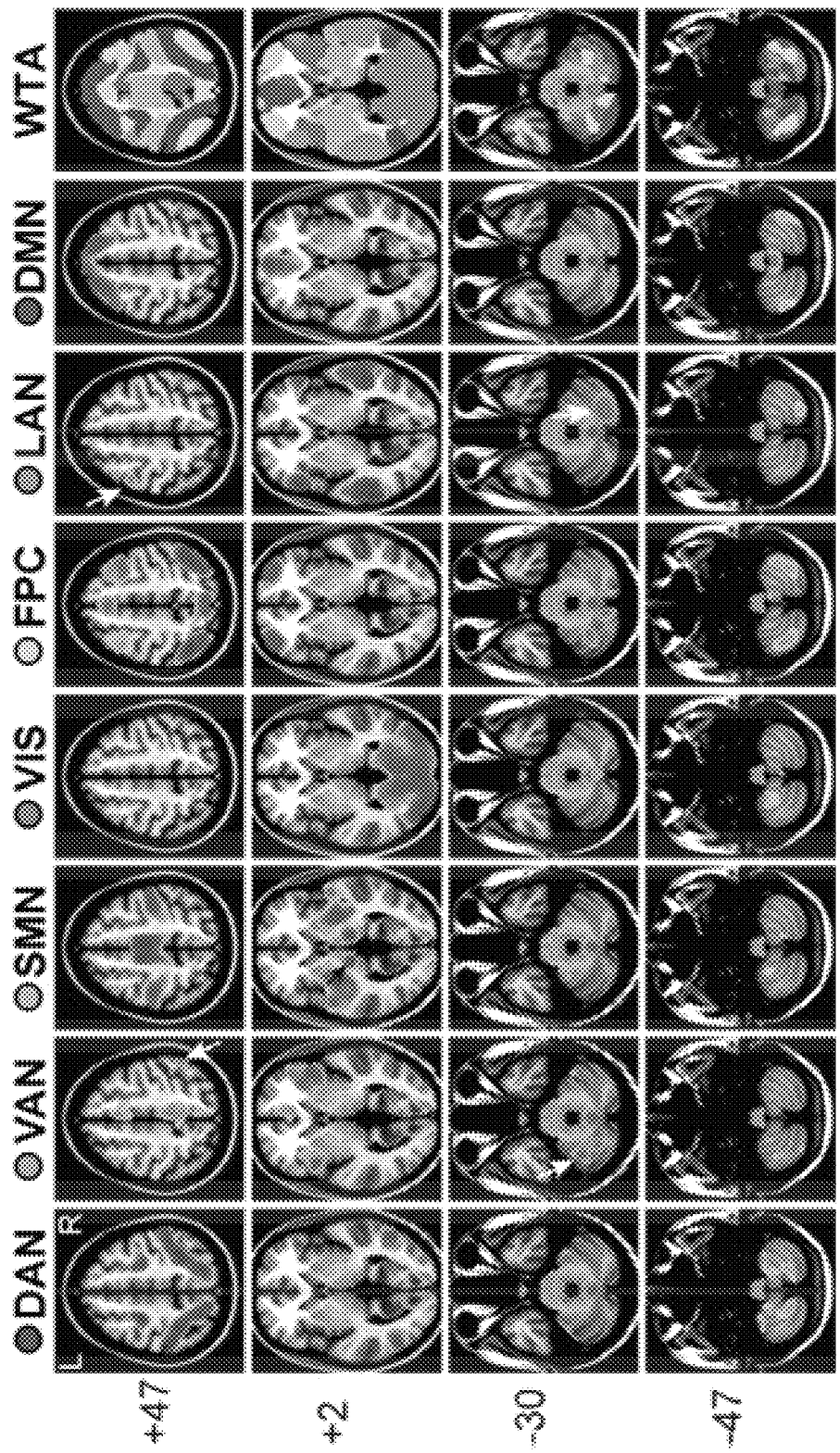
FIG. 13 is a scan of group averaged results.

Further evidence of external validity is shown in FIG. 13. For example, thalamic voxels approximately corresponding to nucleus ventralis posterior were classified as SMN, substantially in agreement. Similarly, voxels in the posterior cerebellum (Crus I and II) and the cerebellar tonsils were classified as DMN (FIG. 13, Z=−30, Z=−47), substantially in agreement. These results are notable because neither cerebellar nor thalamic ROIs were used to generate training data. Further, no cerebellar voxels were within the grey matter mask, which means that the classifier successfully identified cerebellar ROIs purely on the basis of cortical connectivity maps. The perceptron generated asymmetric classification in the cerebellum for the VAN and LAN networks (Z=−30), contralateral to their asymmetric cerebral representation (Z=+47).

The present results (individual and group RSN topographies) exhibit a high degree of face validity with respect to the training data and previously reported RSN results (FIGS. 11A-11F, 12A-12C, and 13). Thus, for example, components of the DMN used as seeds to generate the training data were classified as DMN in all subjects. This was true not only for easily classified networks (e.g., the DMN) but also for networks (e.g., VAN and LAN) that are inconsistently found by unsupervised procedures. The results shown in FIGS. 11A-11F illustrate that the perceptron reliably classified RSNs in each test set individual (AUC>0.971), even in cases in which the RMS error was relatively high (>0.2).

However, inter-individual differences were also evident (FIGS. 11A-11F). These differences systematically varied according to RSN and exhibited RSN-specific zones of high as well as low inter-individual variability (FIGS. 12A-12C). Easily classified voxels (i.e., with high classification values) generally showed the least inter-subject variability. Such regions, e.g., the posterior parietal component of the DMN (FIGS. 12A-12C), were surrounded by zones of high variability (e.g., ring around the angular gyrus). The pre- and post-central gyri consistently showed high SMN classification values but were bordered by regions of high inter-subject SMN variability. Interestingly, inter-subject variability was low also in areas with classification values near 0, particularly in areas typically anticorrelated with other networks (e.g., low DAN variance in the angular gyrus, a component of the DMN; low DMN variance in MT+, a component of the DAN).

At least four factors potentially contribute to observed inter-subject classifier output variability: (i) limited or compromised fMRI data, (ii) limitations intrinsic to the MLP (iii) true inter-individual differences in RSN topography and (iv) misregistration. Each of the possibilities is discussed below.

With regard to (i), the fMRI data used in the present work were obtained in healthy, cooperative young adults. Hence, the fraction of frames excluded because of head motion was low (about 4%). The total quantity of fMRI data acquired in each individual was, by current standards, generous. However, fMRI data quantity clearly affects MLP performance (see 4.4.2 below and FIGS. 14A-14B). Current results suggest that more data generally improves MLP performance. The impact of fMRI data quality and quantity on MLP performance in clinical applications remains to be determined. With regard to (ii), the observation of zones with high classifier values and low variance bordered by regions of high variance may reflect classification uncertainty in areas that truly represent more than one RSN, i.e., voxels with high participation coefficients.

With regard to (iii), on the other hand, the presently observed inter-individual differences may truly reflect individual variability in RSN topography. Previous work has demonstrated that inter-individual differences in task-evoked activity correspond to "transition zones" in resting state networks (e.g., the boundary between parietal DMN and DAN regions). These same regions appear in the inter-subject variance maps for both DMN and DAN (FIGS. 12A-12C). It is also noted that areas of high RSN classification variability (pre-frontal, parietal, lateral temporal) broadly correspond to regions exhibiting the greatest expansion over the course of human development and evolution. This correspondence may possibly be coincidental, but it is consistent with the hypothesis that later developing or evolutionarily more recent areas of the brain tend to be more variable across individuals.

Figure 16A:
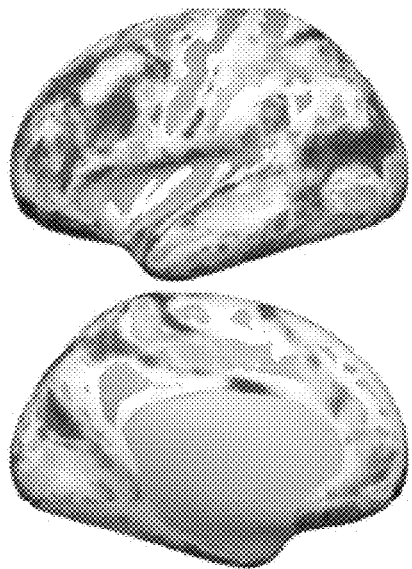
FIGS. 16A and 16B are scans of topography estimates.
Figure 16B:
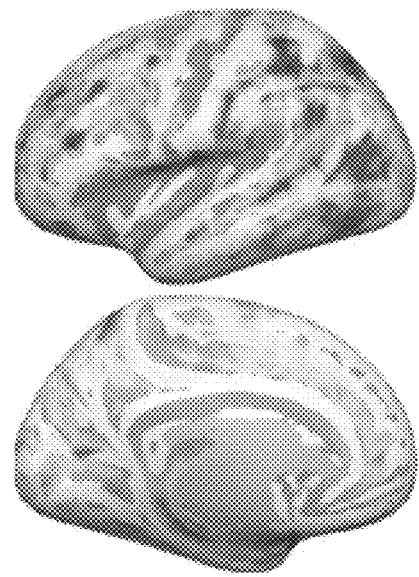

With regard to (iv), some proportion of the variability in observed RSN topography estimates may be explained by uncorrected anatomical variability. To investigate this possibility, the overall RSN standard deviation map (FIG. 16A) was compared to sulcal depth variability (FIG. 16B) and a weak spatial correlation (r=0.2) was found. By inspection, these maps were concordant only at a broad spatial scale: both showed low variability in primary motor/auditory/insular cortices and high variability elsewhere. Little correspondence was evident at finer scales (note lack of annular patterns in FIG. 16B). The degree to which anatomical variability contributes to spurious variance in RSN topography estimates may be addressed by measuring the degree to which non-linear or surface-based registration decreases inter-subject variance and increases overall classifier performance (higher AUC, lower RMSE).

Two distinct types of external validity, that is, correct classification outside the training set, are evident in the results. First, high overall classification performance was achieved for a priori seed-based correlation maps in test (98.2% AUC) and hold-out datasets (98.8% AUC). Performance was reliable in all subjects (97.1% worst-case AUC), which is critical in clinical applications. Second, and perhaps of greater scientific interest, the RSN estimates in areas not covered by seed regions were strongly concordant with previously reported task-based and resting-state fMRI results. For example, while no temporal FPC seed ROI was included in the training set, a posterior temporal gyrus locus was classified as FPC the group level (FIGS. 12A-12C). Similarly, the MLP also identified the parahippocampal gyrus as DMN and a dorsal pre-motor region that has been associated with articulation of speech as LAN. The right inferior cerebellum was first associated with language function by PET studies of semantic association tasks. Identification of this region here as part of the LAN network (FIG. 13, WTA, Z<−30) is doubly significant. First, no cerebellar seeds were used to generate training data and, further, cerebellar voxels were excluded from the gray matter mask, hence, were not seen by the classifier. Second, lateralized RSN components typically are not found by unsupervised seed-based correlation mapping.

These findings highlight the capabilities of supervised classifiers applied to the problem of identifying RSNs in individuals. The representation of language (primarily Broca's and Wernicke's areas) has been extensively studied using task-based fMRI and correlation mapping with a priori selected ROIs. However, the language network, as presently defined, typically is not recovered as such by unsupervised methods. Rather, components of the LAN are generally found only at fine-scale RSN descriptions. Thus, an RSN including Broca's and Wernicke's areas appears as the 11th of 23 components in; these same areas were identified as VAN and DMN. A component consistent with the presently defined LAN at a hierarchical level of 11 (but not 7) clusters has been found. Thus, the exemplary experiment, work demonstrates the potential of supervised classifiers to find networks that are subtle features of the BOLD correlation structure, possibly even minor sub-components within hierarchically organized RSNs that nevertheless have high scientific and/or clinical value. The LAN was specifically included here to meet the clinical imperative of localizing language function in the context of pre-operative neurosurgical planning.

In the exemplary embodiment, the hierarchical scale of an RSN is reflected in training performance trajectories (FIGS. 9E and F): in all $(N_i \times N_h)$ architecture variants, the DMN was the first to be separated from other RSNs. The DMN arguably is the most robust feature in the correlation structure of intrinsic brain activity. Its topography is very similar across RSN mapping strategies (specifically, spatial ICA and seed-based correlation mapping. Here, the DMN and regions anti-correlated with the DMN were well separated along the first principal component of the training data (FIG. 6).

After the DMN, the sensorimotor and visual networks were next to achieve separation during classifier training. These networks are often seen at the next level down in the RSN hierarchy as offshoots of the anti-DMN or extrinsic system. The dorsal attention network achieved only a small peak in error descent compared to other 'extrinsic' networks, though this occurred in close proximity (note overlap of DAN, MOT, VIS peaks in FIG. 9F). In contrast, the LAN and VAN were last to achieve separation during training. This corresponds to the observation that LAN and VAN systems are typically found by analyses extending to lower levels of the RSN hierarchy.

In the exemplary embodiment, the observer is a multi-layer perceptron and the task is to assign RSN labels to each voxel. Performance is evaluated in terms of mean squared classification error and ROC analyses. It follows that MLP performance can be used to evaluate image quality across a wide range of variables, e.g., scanners, and acquisition parameters (e.g., TR, run length, resolution), preprocessing strategies (nuisance regression, filtering, spatial smoothing) and data representations (surface or volume based). This principle is demonstrated by systematically evaluating MLP performance in relation to quantity of fMRI data and seed ROI size.

Figure 14A:
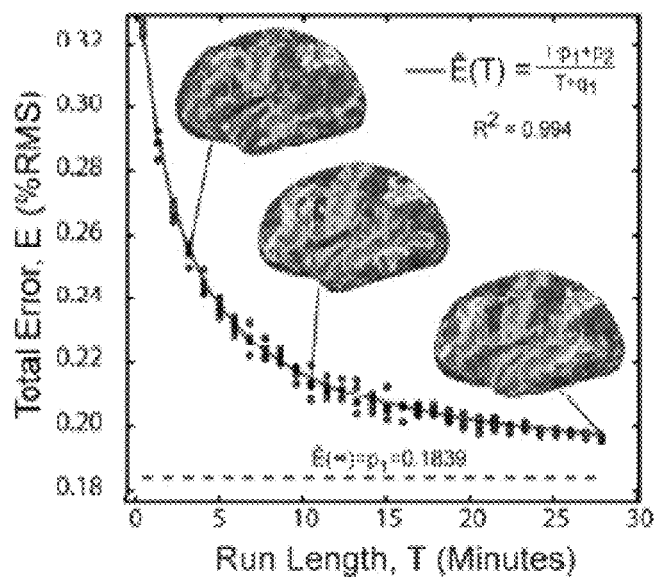
FIGS. 14A and 14B are graphs of exemplary evaluations.

The relation between total quantity of fMRI data and MLP performance (test dataset RMS error) is shown in FIG. 14A. The plotted points represent five replicate MLP training/test runs. RMS error as a function of data quantity was well fit ($R^2=0.994$) by a three-parameter empirically derived hyperbolic function. The parameterized function implies that classifier error monotonically decreases with increasing total fMRI data length but ultimately asymptotes at −18% RMS (with 5 mm radius seeds and no simulated annealing). The existence of this asymptote may indicate that resting-state brain networks are inherently non-separable in the sense of classification. This is consistent with the notion of "near decomposability" of hierarchical systems formed by multiple, sparsely inter-connected modules. This concept has since been extended to brain networks.

Figure 14B:
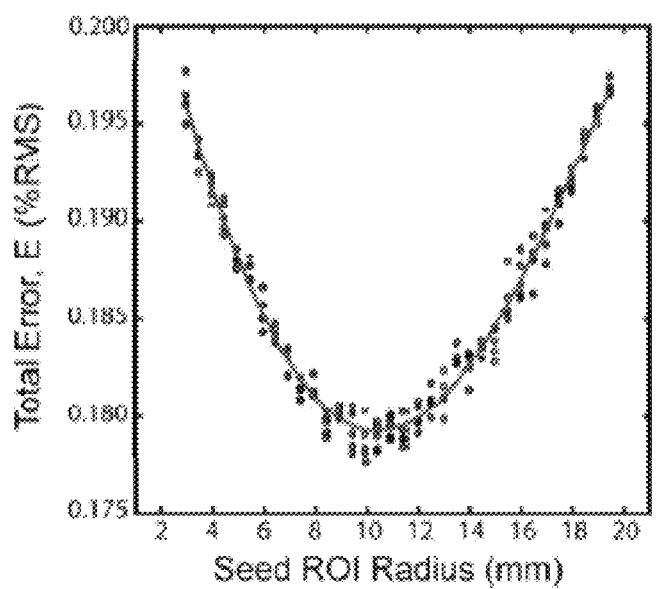

The relationship between seed ROI radius and RMS classification error was explored using a perceptron architecture optimized with 5 mm radius seeds (2500 PCs, 22 hidden nodes). All seeds were masked to include only gray matter voxels. The results of systematically varying seed ROI size are shown in FIG. 14B. A clear minimum in RMS error was obtained with seeds of approximately 10 mm radius. Voxel-wise RSN topographies were qualitatively similar across ROI sizes, but larger seeds generated less noisy RSNs with more pronounced peaks. This result is unexpected, as it deviates from the current standard practice of using approximately 6 mm radius seeds. There are several possible explanations for the present results. Large seeds may best match the characteristic dimensions of RSNs in the 7-network level description of the brain. Alternatively, large seeds may compensate for misregistration in affine-coregistered, volume-preprocessed data. Smaller seeds may be used in classifiers operating on non-linear, surface-coregistered, geodesically smoothed data. The results shown in FIG. 14B reflect the effect of seed radius on the correlation maps used to train the MLP. It is formally possible for a corrupted training set to yield a better classifier as evaluated by test set classification error. Thus, the results shown in FIG. 14B should not be interpreted as unambiguously indicating that 10 mm radius seeds are optimal for correlation mapping.

Inter-individual differences in computed RSN topographies may reflect multiple factors. Cross-gyral contamination due to the relatively large voxels used in this study (4 mm acquisition, 3 mm post-processing analyses) may limit the precision of RSN classification in the dataset. Potential strategies for validating perceptron-derived results include comparison with measures of structural (axonal) connectivity and invasive electrophysiological recording.

The MLP RSN classifier operates at the voxel level via computed correlation maps. After training, it reliably identifies RSN topographies in individual subjects. Classification is rapid (2 minutes using Matlab running on Intel i7 processors) and automated, hence suitable for deployment in clinical environments. After training, classification is independent of any particular seed. Therefore, the trained MLP is expected to be robust to anatomical shifts and distortions, for example, owing to enlarged ventricles and mass effects or even loss of neural tissue (e.g., stroke).

In this experiment, the classifier was trained to operate in 3D image space for compatibility with clinical imaging formats. However, the MLP concept can be readily adapted to operate on correlation maps represented on the cortical surface. Similarly, voxel-wise classifiers can be trained to classify subjects despite anatomical abnormalities (e.g., brain tumors) by altering the domain of the training set, i.e., excluding tumor voxels. Another potentially useful MLP modification would be removal by regression of the relationship between correlation and distance to the seed. Such regression may decrease the reliance of the classifier on local connectivity, thereby reducing susceptibility to corruption by movement artifact.

As compared to known systems that are used for brain mapping, the embodiments described herein enable a substantially efficient task-less system for brain mapping. More specifically, the embodiments described herein include a computing device for use in a system for mapping brain activity of a subject that generally comprises a processor. The processor is programmed to select a plurality of measurements of brain activity that is representative of at least one parameter of a brain of the subject during a resting state. Moreover, the processor is programmed to compare at least one data point from each of the measurements with a corresponding data point from a previously acquired data set from at least one other subject. The processor is also programmed to produce at least one map for each of the measurements based on the comparison of the resting state data point and the corresponding previously acquired data point. The processor may also be programmed to categorize the brain activity in a plurality of networks in the brain based on the map. By using previously acquired data points to categorize the brain activity in a plurality if networks in the brain of the subject, task-based techniques may be avoided. Moreover, by having the processor select the plurality of measurements, a user may no longer need to spend a considerable amount of time determining which measurements, such as voxels, to select.

In various aspects, the workflow associated with the implementation of the MLP-based functional mapping methods disclosed herein may be integrated into any existing workflow management platform without limitation. In these various aspects, the use of an existing workflow management platform streamlines this workflow and provides a means of facilitating the application of the MLP-based functional mapping methods disclosed herein into a wide range of clinical settings.

Figure 31:
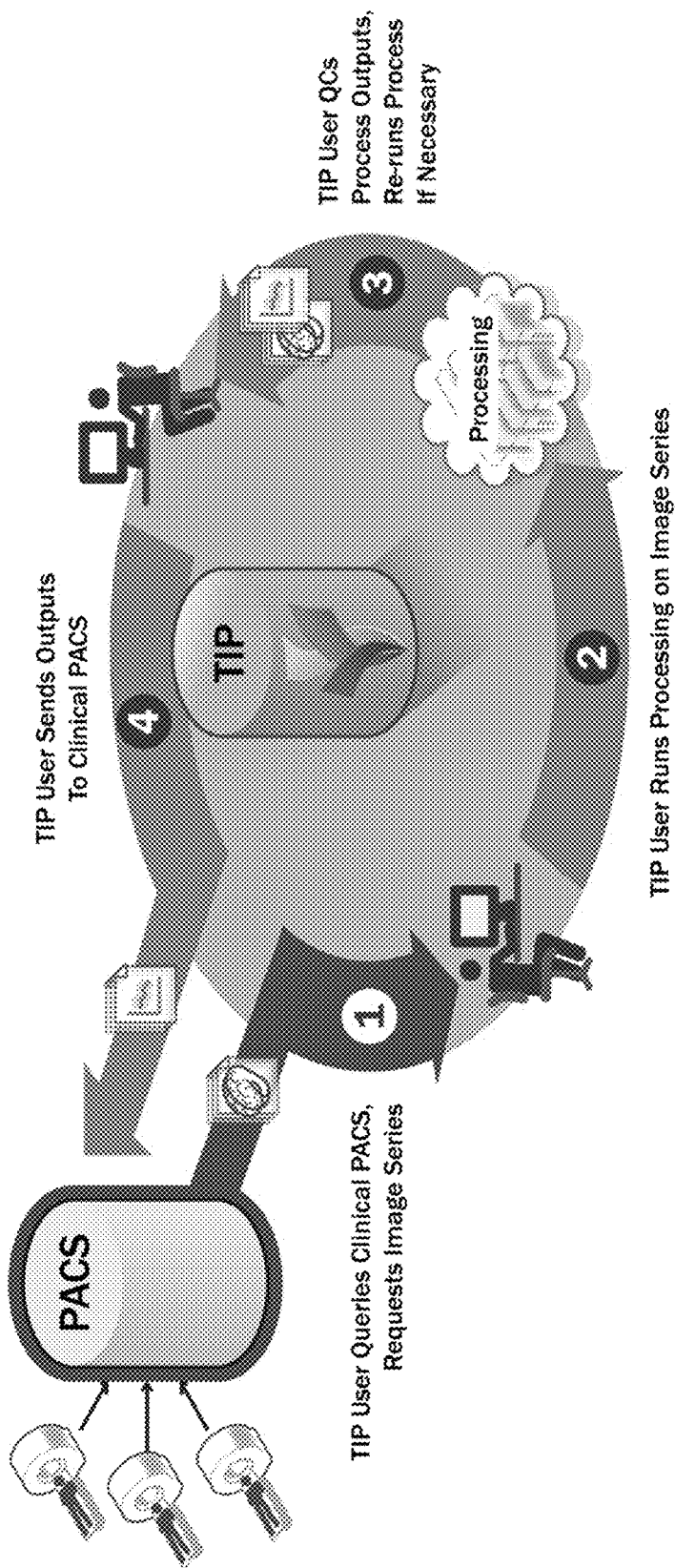
FIG. 31 is a schematic illustration of a workflow software platform for managing workflow associated with rs-fMRI data acquisition and analysis.
Figure 32:
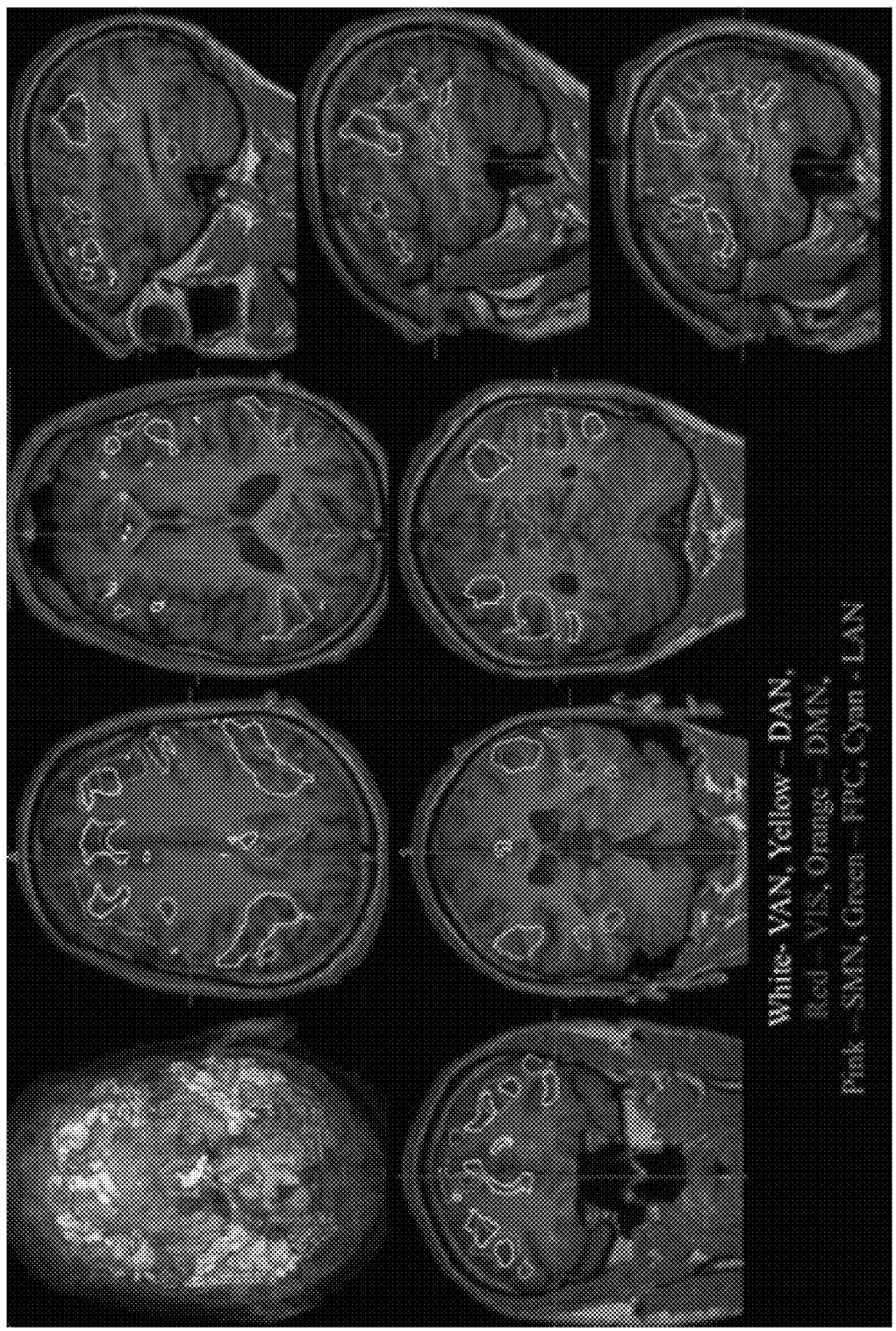
FIG. 32 is screen capture showing perceptron-based RSNs overlaid on a display of a neuronavigation system.

In one aspect, the workflow associated with the implementation of the MLP-based functional mapping methods disclosed herein is streamlined to facilitate acquisition of the rs-fMRI data and to rapidly transfer data before and after processing using an existing system including, but not limited to, a Translational Imaging Portal (TIP). TIP is a customized version of the existing XNAT imaging informatics platform configured to facilitate the translation of imaging research into clinical practice, illustrated schematically in FIG. 31. XNAT is a web-based software platform designed to facilitate common management and productivity tasks for imaging and associated data. The XNAT platform includes an image repository to store raw and post-processed images, a database to store metadata and non-imaging measures, and user interface tools for accessing, querying, visualizing, and exploring data. XNAT supports all common imaging methods, and its data model can be extended to capture virtually any related metadata. XNAT includes a DICOM workflow to enable exams to be sent directly from scanners, PACS, and other DICOM devices. A web-based application enabling use of the XNAT platform provides a number of productivity features, including, but not limited to, data entry forms, searching, reports of experimental data, upload/download tools, access to standard laboratory processing pipelines, and an online image viewer. A fine-grained access control system ensures that users are restricted to accessing only authorized data. XNAT also includes a web services API for programmatic access and open plugin architecture for extending XNAT's core capabilities.

In various aspects, the individual resting state network (RSN) maps produced using the supervised classifier methods as described above are used to determine a target location for a therapeutic intervention in a subject with a neurological disorder. The target locations determined from the individual resting state network (RSN) maps in these various aspects, are associated with any suitable therapeutic intervention without limitation. Non-limiting examples of suitable therapeutic interventions include implantable brain stimulators, non-invasive transcranial magnetic stimulations, non-invasive direct transcranial electric stimulation, implantable drug release devices, pharmacologic interventions, electroconvulsive therapies, radiation therapies, surgical resections of lesions, laser interstitial thermal therapies, brain computer interfaces, stereotactic radiation treatments, focused ultrasound treatments, and any other suitable therapeutic interventions.

Figure 36:
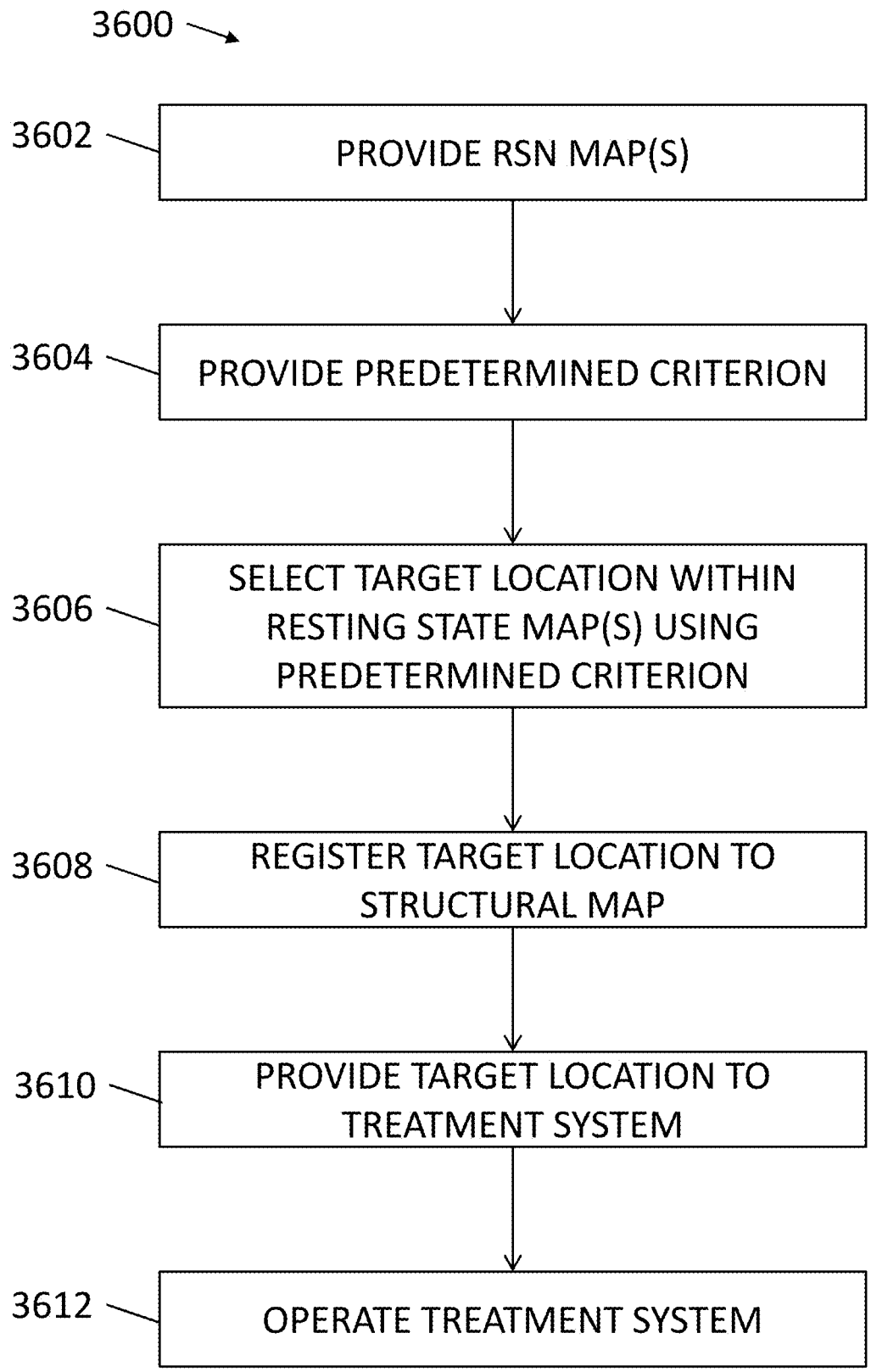
FIG. 36 is a flow chart summarizing a method to determine a target location for a therapeutic intervention in a subject according to one aspect of the disclosure.

FIG. 36 is a flowchart summarizing a method 3600 of determining a target location for a therapeutic intervention in a subject with a neurological disorder in one aspect. As illustrated in FIG. 36, the method 3600 includes providing at least one RSN map the brain of the subject at step 3602. In one aspect, the at least one RSN map is produced using a supervised classified method including, but not limited to, a supervised classifier method using the multi-layer perceptron as described above. Each of the at least one RSN maps includes a plurality of functional voxels within a brain of the subject, with a probability of membership in an RSN associated with each functional voxel.

In one aspect, the at least one RSN map is provided at 3602 by determining each probability of membership in each RSN of each functional voxel of the plurality of functional voxels of a resting-state functional MRI (rs-fMRI) of the brain of the subject using a supervised classifier method, and associating each probability of membership in each RSN with each functional voxel of the plurality of functional voxels to produce each RSN map. In an additional aspect, providing at least one RSN map the brain of the subject at step 3602 further includes obtaining an rs-fMRI of the brain of the subject that is analyzed to produce the at least one RSN map as described above.

Referring again to FIG. 36, the method 3600 further includes providing a predetermined criterion at 3604. In one aspect, the predetermined criterion provided at 3604 is specifically defined for the particular neurological disorder to be treated using the therapeutic intervention targeted by the method 3600. In various aspects, the predetermined criterion is provided at 3604 in the form of predetermined target range of values of an index derived from the at least one RSN map provided at 3602, as described in additional detail below.

Figure 37:
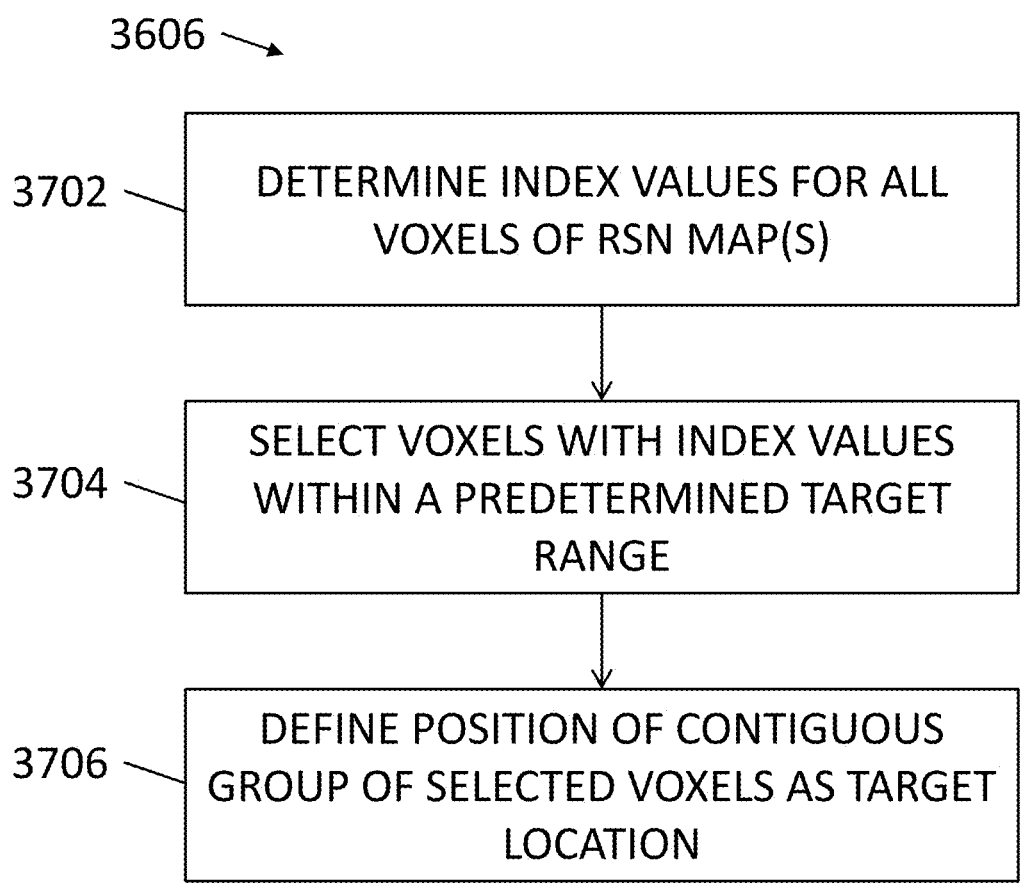
FIG. 37 is a flow chart summarizing steps for the selection of the target location using a predetermined criteria from the method illustrated in FIG. 36 according to one aspect of the disclosure.

The method 3600 further includes selecting the target location within the RSN map(s) at 3606 using the predetermined criterion. As illustrated in FIG. 37 in one aspect, selecting the target location within the RSN map(s) at 3606 includes determining index values for all voxels of the RSN map(s) at 3702. In various aspects, each index value is based on the probability of membership in an RSN from at least one of the RSN maps. Non-limiting examples of index values determined at 3702 include the probability of membership in one RSN from one of the RSN maps and/or a combination of two or more probabilities of membership in two or more RSNs from two or more RSN maps.

In various aspects, the combination of two or more probabilities of membership in two or more RSNs from two or more RSN maps include, but are not limited to, mathematical combinations of at least two probabilities of membership. Mathematical combinations include, but are not limited to, a sum, a difference, a product, a ratio, and any combination thereof. In various other aspects, the combination of two or more probabilities of membership in two or more RSNs from two or more RSN maps include, but are not limited to, transformations of one or more of the at least two or more probabilities of membership, transformations of the mathematical combination of the at least two or more probabilities of membership, and any combination thereof. Non-limiting examples of transformations include trigonometric transformations, logarithmic transformations, normalizations, and any combination thereof.

Referring again to FIG. 37, selecting the target location within the RSN map(s) at 3606 includes further includes selecting at least one functional voxel of the plurality of functional voxels with an index value falling within a predetermined target range for the neurological disorder at 3704. In one aspect, the predetermined target range of index values are defined by a statistic derived from the RSN map(s) including, but not limited to, a maximum index value and a minimum index value calculated using all functional voxels of the plurality of functional voxels of the RSN map(s). In one aspect, a functional voxel with an index value equal to the maximum index value or the minimum index value is selected at 3704. In another aspect, a functional voxel with an index value less than the maximum index value is selected at 3704. In an additional aspect, a functional voxel with an index value greater than the minimum index value is selected at 3704. In another additional aspect, a functional voxel with an index value between the minimum index value and the maximum index value is selected at 3704. The functional voxels selected at 3704 are analyzed further and a group forming a contiguous group is selected as the target location at 3706.

Referring again to FIG. 36, the target location selected within the RSN map(s) at 3606 are registered to a structural map of the brain of the subject at 3608. As described above, the structural map is an image representing anatomical structures within the brain of the subject in various aspects including, but not limited to, a structural MRI. In one aspect, the method 3600 further includes providing and/or obtaining the structural MRI from the brain of the subject. The method 3600 also includes providing the target location to a treatment system used to provide the therapeutic intervention at 3610. In various aspects, the operation of the treatment system is defined relative to, or registered to, the structural MRI coordinate system. In one additional aspect, the method 3600 includes operating the treatment system 3612 based on the target location provide at 3610.

In various aspects, the predetermined criterion is a functionally-based criterion or a structurally-based criterion. In one aspect, the functionally-based criterion includes defining the target location exclusively in terms of functional data summarized in the RSN map(s) analyzed using the method 3600 as illustrated in FIG. 36 and as described above. In one aspect, all functional voxels of the RSN map(s) are analyzed to identify the target location for the therapeutic intervention. In another aspect, the structurally-based criterion includes selecting a structural feature or region known to be associated with the neurological disorder of the subject, and/or selecting a structural feature or region containing target locations thought to be suitable for a therapeutic intervention for the neurological disorder. In this other aspect, once the structural feature or region of the brain of the subject is selected, the structurally-based criterion further includes analyzing the portion of the functional voxels positioned within the structural feature or region of the brain to determine the target location.

Figure 38:
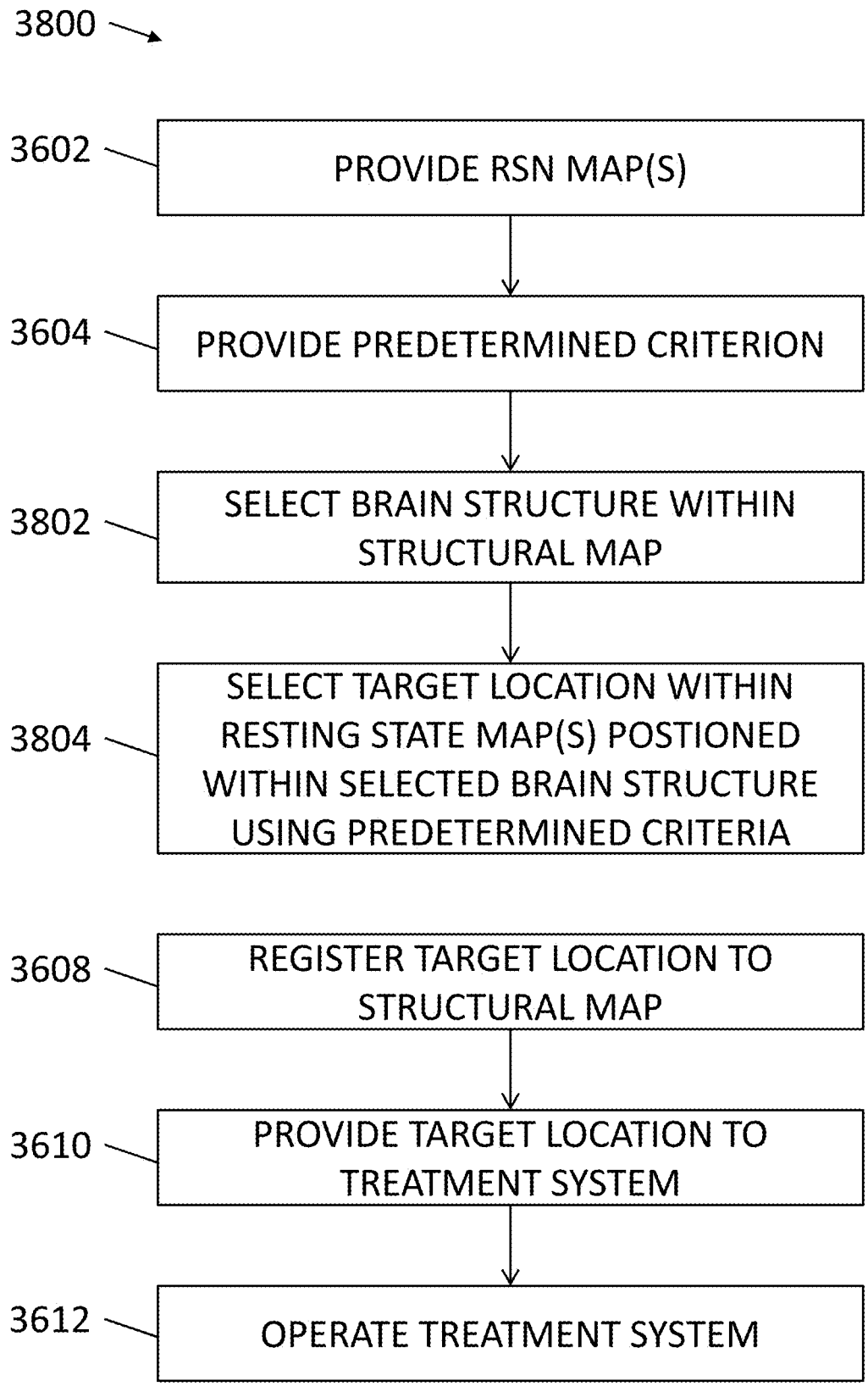
FIG. 38 is a flow chart summarizing a method to determine a target location for a therapeutic intervention in a subject according to another aspect of the disclosure.

FIG. 38 is a flow chart illustrating a method 3800 of determining a target location for a therapeutic intervention in a subject with a neurological disorder using a structurally-based criterion in one aspect. The method 3800 includes selecting structural feature or region of the brain of the subject at 3802 from within a structural map. Non-limiting examples of structural features or regions of the brain of the subject include a tumor region, Broca's area, Wernicke's area, left/right dorsolateral prefrontal region, anterior cingulate cortex (ACC), dorsolateral prefrontal cortex (DLPFC), primary motor cortex, premotor cortex, supplementary motor area, posterior parietal cortex, cerebellum, basal ganglia, and pedunculopontine nucleus. In this aspect, the structural map is an image representative of anatomic structures and/or features within the brain of the subject including, but not limited to, a structural MRI. In one aspect, the method 3800 further includes providing a structural map and/or obtaining a structural MRI from the brain of the patient (not illustrated).

Referring again to FIG. 38, the target location is selected at 3804 within the RSN map(s) in a manner similar to the target location selection at 3606 as illustrated in FIG. 36 and described above, except that the target location is selected from within the brain structure or region selected at 3802, rather than from within all voxels of the RSN maps, as illustrated at 3606 of FIG. 36 and described above. Referring again to FIG. 38, the method 3800 further includes registering the selected target location to a structural map at 3608, providing the selected target location to a treatment system at 3610, and operating the treatment system at 3612 in a manner similar to the method 3600 illustrated in FIG. 36 and described above.

In an additional aspect, the individual resting state network (RSN) maps produced using the supervised classifier methods as described above are used to determine a path to the target location identified as described above. In this additional aspect, the path extends from the cortical surface of the brain of the subject to the target location. The path is selected to minimize injury to functional brain tissue as a result of accessing the target location using the treatment device. The path includes a group of adjoining voxels of the plurality of functional voxels of the at least one RNS map extending from the cortical surface to the target location.

In this additional aspect, the path is determined by identifying a group of candidate voxels of the plurality of functional voxels with likelihoods of membership in the RSNs from the at least one RSN map below a functional threshold and selecting a group of adjoining voxels forming the path from the group of candidate voxels. In one aspect, the functional threshold is defined as a likelihood of membership in the RSN that is greater than the lowest 10% of all likelihoods of membership of the plurality of functional voxels of the at least one RSN map. In another aspect, the functional threshold is defined as a likelihood of membership in the RSN that is greater than the lowest 5% of all likelihoods of membership of the plurality of functional voxels of the at least one RSN map.

Figure 39:
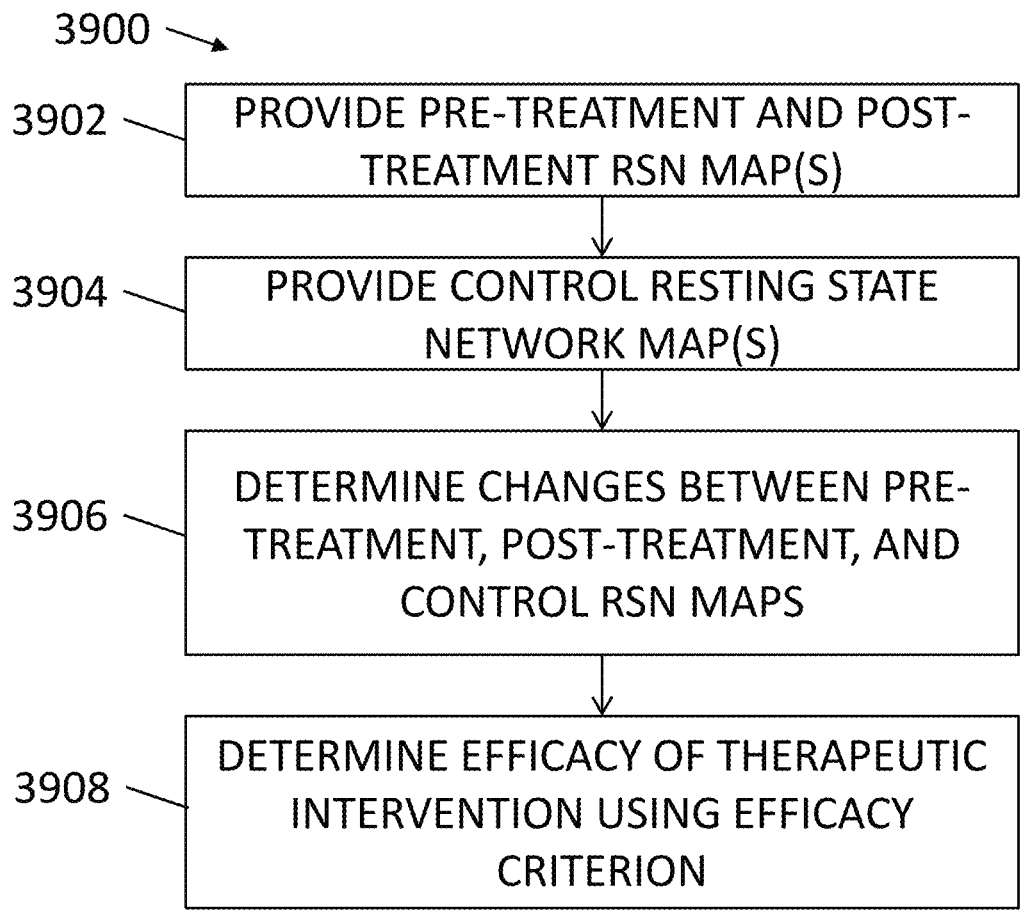
FIG. 39 is a flow chart summarizing a method for monitoring an efficacy of a therapeutic intervention according to an aspect of the disclosure.

In another additional aspect, the individual resting state network (RSN) maps produced using the supervised classifier methods as described above are used to monitor an efficacy of a therapeutic intervention in a subject with a neurological disorder. FIG. 39 is a flowchart summarizing a method 3900 of monitoring the efficacy of the therapeutic intervention in one aspect. As illustrated in FIG. 39, the method 3900 includes providing at least one pre-treatment RSN map of the subject prior to the therapeutic intervention and at least one post-treatment RSN map of the subject after the therapeutic intervention at 3902. Each of the at least one pre-treatment and post-treatment RSN maps includes a plurality of pre-treatment functional voxels and post-treatment functional voxels within a brain of the subject, respectively. Each of the pre-treatment and post-treatment functional voxels is associated with a probability of membership in an RSN. The method 3900 further includes providing at least one control RSN map representative of a healthy subject that includes a plurality of control functional voxels associated with a probability of membership in an RSN least one RSN map the brain of the subject at 3904. In an additional aspect (not illustrated) the method 3900 further includes providing at least one disorder RSN map representative of a subject with the neurological disorder in which each of the at least one disorder RSN maps includes a plurality of disorder functional voxels within a brain of the subject associated with a probability of membership in an RSN. In one aspect, the pre-treatment, post-treatment, control, and disorder RSN maps are produced using the supervised classified method including, but not limited to, a supervised classifier method using the multi-layer perceptron as described above.

Figure 40:
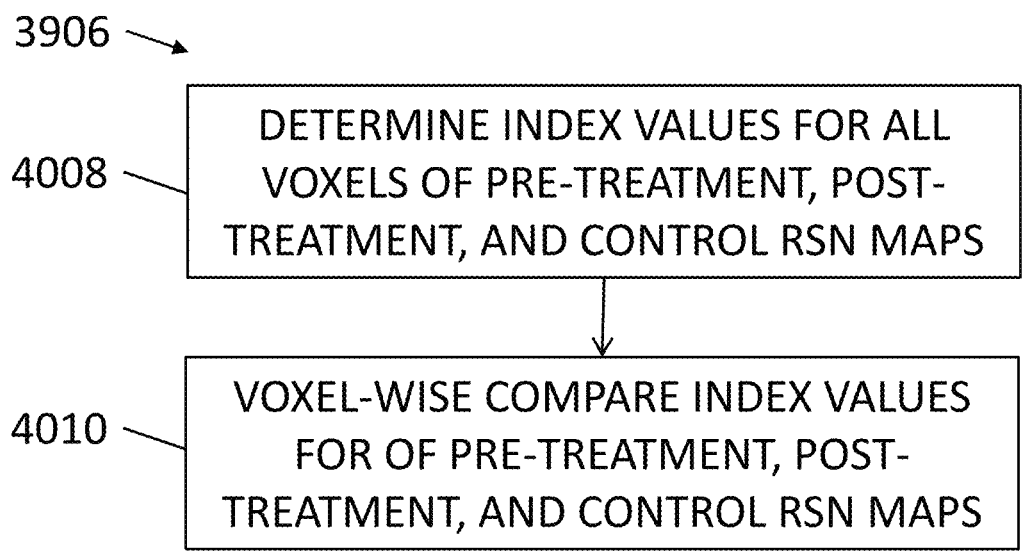
FIG. 40 is a flow chart summarizing steps for determining changes between pre-treatment, post-treatment, and control RSN maps from the method illustrated in FIG. 39 according to one aspect of the disclosure.

Referring again to FIG. 39, the method 3900 also includes determining changes between at least a portion of the pre-treatment, post-treatment, and control RSN maps at 3906. FIG. 40 is a flow chart illustrating a method of determining the changes at 3906 in one aspect. As illustrated in FIG. 40, the index values of all functional voxels of the pre-treatment, post-treatment, and control RSN maps are determined at 4008. Each of the at least one RSN maps includes a plurality of functional voxels within a brain of the subject, with a probability of membership in an RSN associated with each functional voxel. Each index value of each voxel, as described above, includes, but is not limited to a probability of membership in one RSN, a combination of two or more probabilities of membership in two or more RSNs, and any combination thereof. The index values of each corresponding voxel of the pre-treatment, post-treatment, and control RSN maps are compared at 4010 to determine the changes.

Referring again to FIG. 39, the method 3900 further includes determining the efficacy of the therapeutic intervention using an efficacy criterion at 3908. Any efficacy criterion may be used in the method 3900 including, but not limited to, an efficacy criterion that includes assessing whether each voxel's index value for the post-treatment RSN map is characterized as closer to the corresponding index values for the control RSN and/or further from the corresponding index values for the disorder RSN, as compared to the index values for the pre-treatment RSN. In another aspect, the efficacy criterion includes assessing the magnitude and direction of changes in the index values of the post-treatment RSN relative to the pre-treatment RSN, as compared to the magnitude and direction of changes in the index values of the control RSN relative to the disorder RSN.

In one aspect, the efficacy criterion includes classifying the therapeutic intervention as effective if each index value of each post-treatment voxel falls between each corresponding index value of each pre-treatment voxel and each corresponding index value of each control voxel. In another aspect, the efficacy criterion includes classifying the therapeutic intervention as not effective if each index value of each post-treatment voxel is essentially equal to each corresponding index value of each pre-treatment voxel, or if each index value of each pre-treatment voxel falls between each corresponding index value of each post-treatment voxel and each corresponding index value of each control voxel. In an additional aspect, the efficacy criterion includes classifying the therapeutic intervention as effective if each index value of each pre-treatment voxel falls between each index value of each corresponding post-treatment voxel and each index value of each corresponding disorder voxel. In another additional aspect, the efficacy criterion includes classifying the therapeutic intervention as not effective if each index value of each post-treatment voxel falls between each index value of each corresponding pre-treatment voxel and each index value of each corresponding disorder voxel.

Exemplary embodiments of the system, apparatus, and method are described above in detail. The system, apparatus, and method are not limited to the specific embodiments described herein, but rather, components of the system and apparatus, and/or steps of the methods may be utilized independently and separately from other components and/or steps described herein. For example, but not limited to, the system may also be used in combination with other apparatus, systems, and methods, and is not limited to practice with only the system as described herein. Rather, the exemplary embodiment can be implemented and utilized in connection with many other applications.

EXAMPLES

The following examples demonstrate various aspects of the disclosure.

Example 1: Guidance of rTMS Treatment Using rs-fMRI Functional Mapping

To assess clinical utility and neural network dynamics of resting-state functional MRI (rs-fMRI) for the targeting of bilateral repetitive transcranial magnetic stimulation (rTMS) for a subject with neurological disturbances associated with chronic/repetitive traumatic brain injury (TBI), the following experiments were conducted.

Individual-level connectome mapping was used to identify left/right dorsolateral prefrontal targets with maximum autocorrelation between dorsal attention network (DAN) and default mode network (DMN). Twenty sessions of left-sided excitatory and right-sided inhibitory rTMS were delivered to a retired NFL defensive lineman as part of a randomized, controlled trial. Montgomery-Asberg Depression Rating Scale (MADRES), cognitive testing, headache measures, and rs-fMRI were conducted before and after treatment. Baseline rs-fMRI findings were compared with 12 age- and gender-matched healthy individuals and 10 subjects with depression and TBI.

The rTMS-treated subject was a male in his fourth decade of life with a history of neurological illness associated with repetitive head trauma during a prior career as a defensive lineman in the National Football League and at the amateur level. The subject reported a history of at least 12 prior concussions, likely experienced at least 7,000 sub-concussive head impacts prior to his NFL career as estimated by the Cumulative Head Impact Index, and further experienced an unknown but likely comparable number during his NFL career. The subject described a history of progressively worsening depression, anxiety, impulsivity, anger, and neurocognitive impairment (particularly long-term and short-term memory) over the previous two or three years. The subject indicated that he was unable to work and had restricted social function because of cognitive impairments and emotional dysregulation. The subject had previously demonstrated inadequate response to sertraline, paroxetine, and alprazolam and was not taking any neurological medications at the time of the study. The subject was part of a pilot double-blind randomized-controlled trial of rTMS for depression associated with TBI with a planned sample size of 20.

For comparison, 10 additional subjects with a history of depression and TBI (8 males, ages 19 to 64) received rs-fMRI scans as part of the aforementioned randomized-controlled trial with the same imaging protocol as the experimental subject, but without rTMS treatment. This included patients with clinically significant depression as quantified by a score of at least 10 on the Montgomery-Asberg Depression Rating Scale (MADRS) as well as a history of TBI associated with low risk of seizure disorder. A healthy control group was also selected that included 12 male volunteers (ages 30 to 36) who received rs-fMRI scans as part of a previous study.

Repetitive transcranial magnetic stimulation (rTMS) was selected as a treatment for the subject due to previous efficacy of rTMS as a novel treatment modality for major depressive disorder (MDD) and in stroke rehabilitation. Without being limited to any particular theory, the rTMS likely resulted in selective modulation of cortical excitability, which is also known to be affected in traumatic brain injury (TBI).

It was hypothesized that individualized rs-fMRI map-based rTMS targeting of the portion of DAN within DLPFC most anti-correlated with DMN would effectively modulate submental ACC, a key region involved in dysfunctional attention-default interactions in depression, resulting in improved mood in TBI patients. Without being limited to any particular theory, TBI is associated with connectivity changes in regions and networks involved in emotion regulation, including anterior cingulate cortex (ACC), dorsolateral prefrontal cortex (DLPFC), dorsal attention network (DAN), and default mode network (DMN). These regions are also central in recent efforts to identify methods for functional connectivity-based targeting of rTMS for major depression disorder (MDD).

All subjects were subjected to clinical testing to characterize neurological state independently of the rs-fMRI measurements described below. The rTMS-treated subject was assessed at baseline (pre-treatment) and after the full course of treatment. The clinical testing included depression testing with MADRS, personality testing with the temperament and character inventory (TCI), self-report mood scales in the NIH Toolbox Emotion Battery (EB) and TBI Quality of Life scale (TBI-QoL), neurocognitive testing with the NIH Toolbox Cognitive Battery (CB), self-report headache Likert scores and six-question Headache Impact Test (HIT-6), and an expert psychiatric evaluation based on DSM-5 diagnostic criteria. MADRS, TCI, and EB were repeated at a follow-up assessment six weeks after the completion of the treatment course for the rTMS-treated subject; CB was not repeated due to the subject's preference. MADRS was the primary outcome measure for the double-blind randomized-controlled trial.

In addition, structural and functional MRI scans were performed on the rTMS-treated subject the baseline and at the end of the treatment course. For all subjects, functional and anatomical images were acquired with a 3T Siemens Magnetom Prisma magnetic resonance scanner (Siemens, Erlangen, Germany). The rTMS-treated subject was imaged both before and after rTMS treatment. Acquisition included 16.5 minutes of resting-state blood oxygen-level dependent (BOLD) scans in three runs (416 frames per run, 48 axial slices using 4-band acquisition, 3 mm cubic voxel resolution, repetition time (TR) 800 ms, echo time (TE) 26.6 ms, flip angle 61 degrees, imaging matrix 72×72) in addition to a T1 MPRAGE structural sequence (176 frames, 0.9375× 0.9375×1 mm voxel resolution, TR 2400 ms, TE 3.19 ms, flip angle 8 degrees, imaging matrix 256×256).

Figure 17:
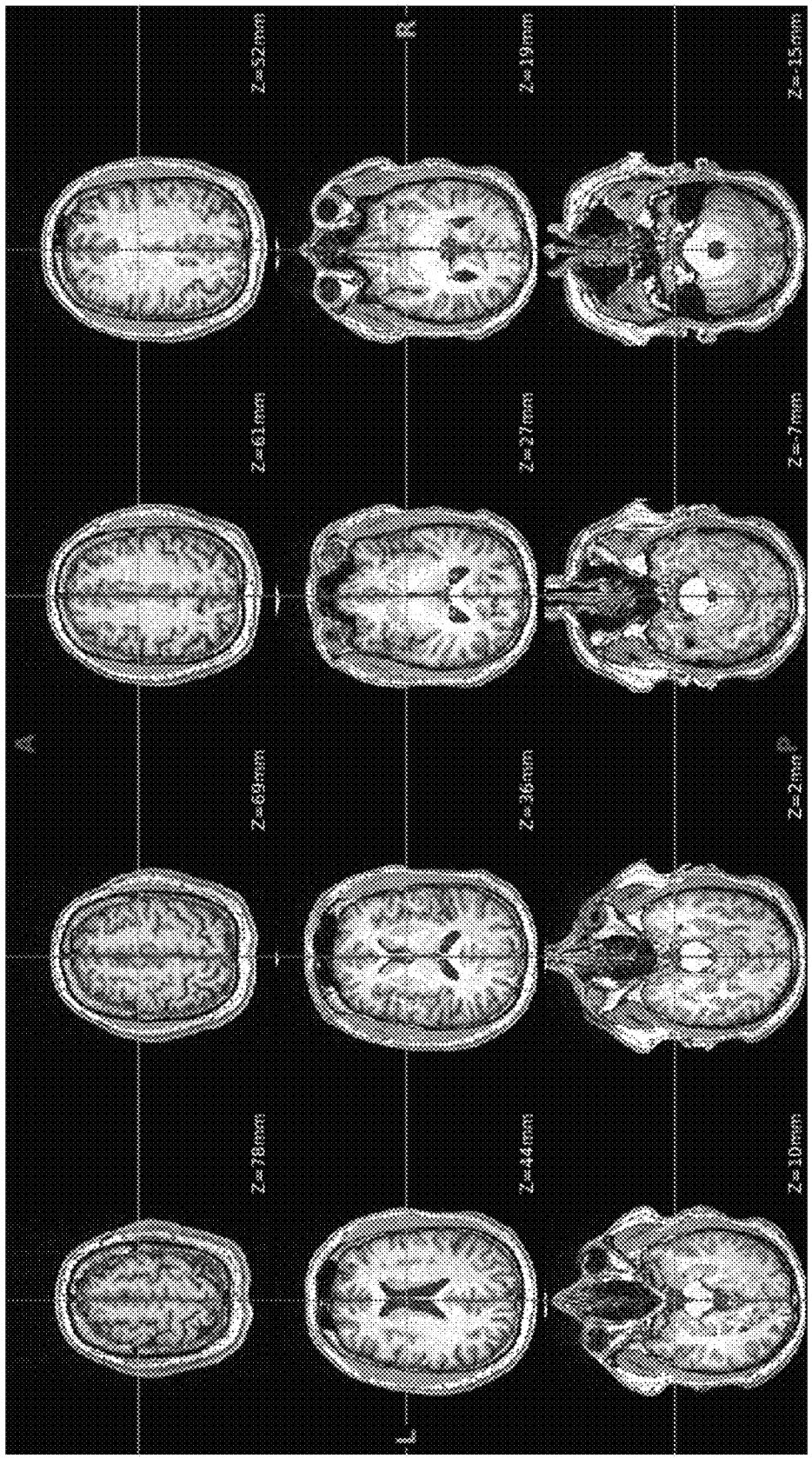
FIG. 17 is a series of images showing axial views of T1-weighted anatomical MRI scans obtained from a brain of a subject prior to an rTMS treatment.

FIG. 17 shows representative axial views of a T1-weighted anatomical MRI scan obtained from the subject prior to rTMS treatment. Reference alignment lines were added for the purpose of comparing slices to one another; red and green reference lines represent the center of the image along the x- and y-axes, respectively. No gross anatomical abnormalities were noted.

Spatial alignment and common Talairach atlas registration of the functional and anatomical images were performed using a 4 dfp suite of tools developed in-house. Anatomical segmentation and surface reconstruction was conducted using FreeSurfer (version 5.3.0, Human Connectome Project release) on the subject's T1-weighted anatomical MRI scan. Motion scrubbing with framewise displacement (FD) of 0.5 mm, nuisance regression, global signal regression, temporal filtering, spatial smoothing, and motion epoch interpolation were performed using in-house scripts.

Quality control plots for the pre-treatment and post-treatment scans were used to estimate the influence of artifact from head motion and nuisance signals qualitatively. These plots were used to calculate frame-wise FD (frame-wise displacement of the head after realignment) and DVARS (root mean square value of the overall change in signal intensity between frames). The Pearson correlation between FD and DVARS were calculated in order to determine the influence of head motion on overall BOLD signal fluctuations. After processing, FD-DVARS correlation was minimized for both pre-treatment scans (from $r=0.63$ to $r=0.08$) and post-treatment scans (from $r=0.69$ to $r=0.13$). To verify that the FD threshold was appropriate for the scan parameters, processing was repeated with a more aggressive FD threshold of 0.3 mm, which yielded similar pre- and post-treatment values of $r=0.06$ and $r=0.02$, respectively.

Figure 18A:
FIG. 18A is a graph of framewise BOLD signal fluctuation (DV) and framewise displacement of the head after realignment (FD) as a function of image frame number, based on pre-processed rs-fMRI imaging data obtained from a subject prior to rTMS treatment.
Figure 18B:
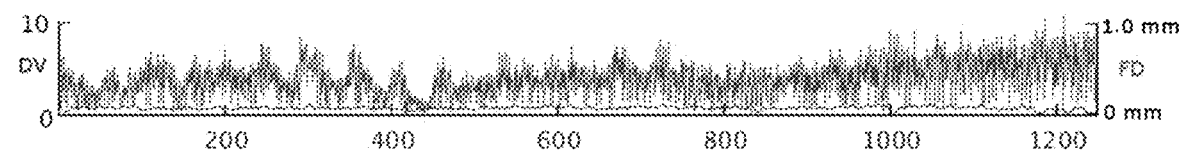
FIG. 18B is a graph of framewise BOLD signal fluctuation (DV) and framewise displacement of the head after realignment (FD) as a function of image frame number, based on post-processed rs-fMRI imaging data obtained from a subject prior to rTMS treatment.
Figure 18C:
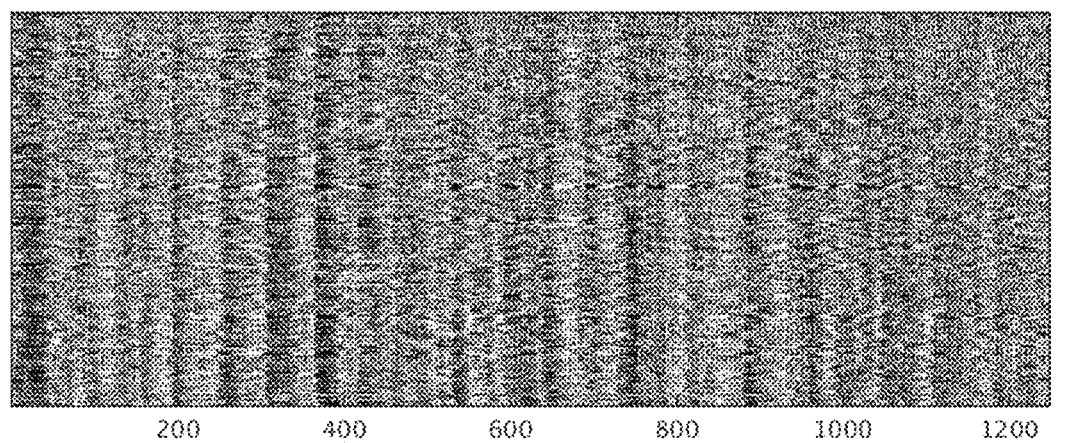
FIG. 18C is a voxel-wise map of BOLD signal fluctuations calculated using pre-processed rs-fMRI imaging data obtained from a subject prior to rTMS treatment.
Figure 18D:
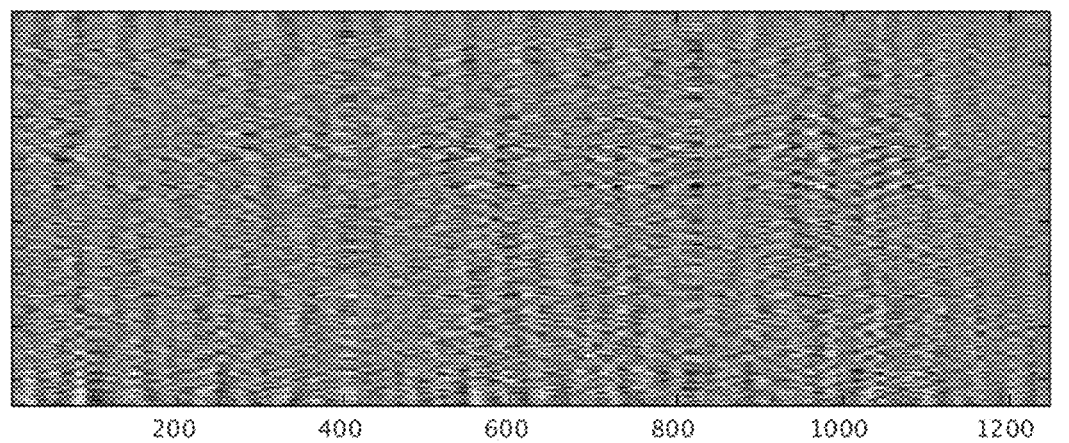
FIG. 18D is a voxel-wise map of BOLD signal fluctuations calculated using post-processed rs-fMRI imaging data obtained from a subject prior to rTMS treatment.
Figure 18E:
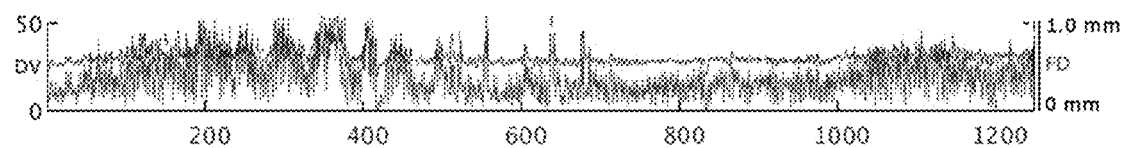
FIG. 18E is a graph of framewise BOLD signal fluctuation (DV) and framewise displacement of the head after realignment (FD) as a function of image frame number, based on pre-processed rs-fMRI imaging data obtained from a subject after rTMS treatment.
Figure 18F:
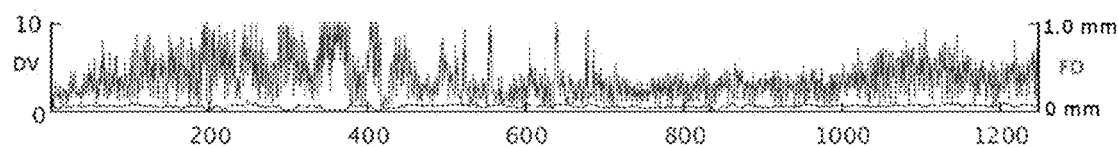
FIG. 18F is a graph of framewise BOLD signal fluctuation (DV) and framewise displacement of the head after realignment (FD) as a function of image frame number, based on post-processed rs-fMRI imaging data obtained from a subject after rTMS treatment.
Figure 18G:
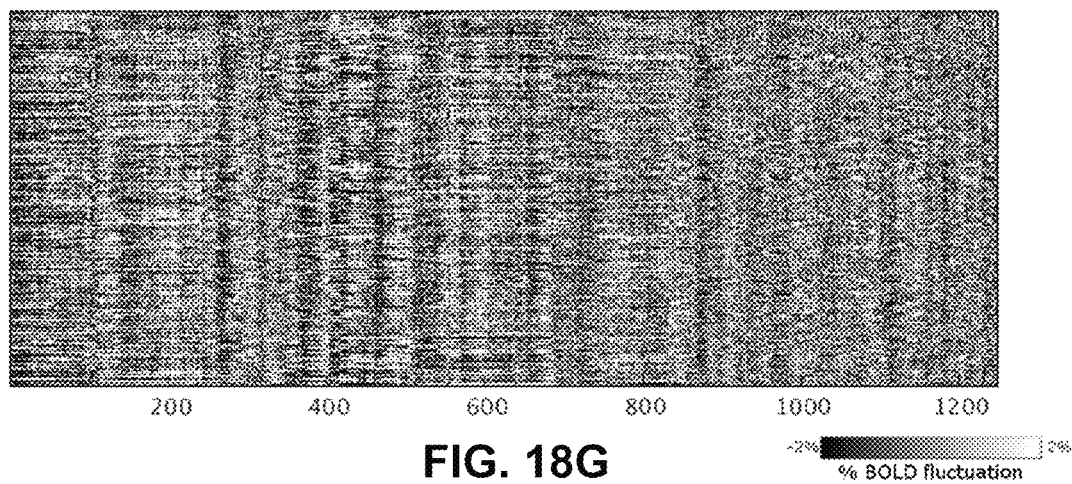
FIG. 18G is a voxel-wise map of BOLD signal fluctuations calculated using pre-processed rs-fMRI imaging data obtained from a subject prior to rTMS treatment.
Figure 18H:
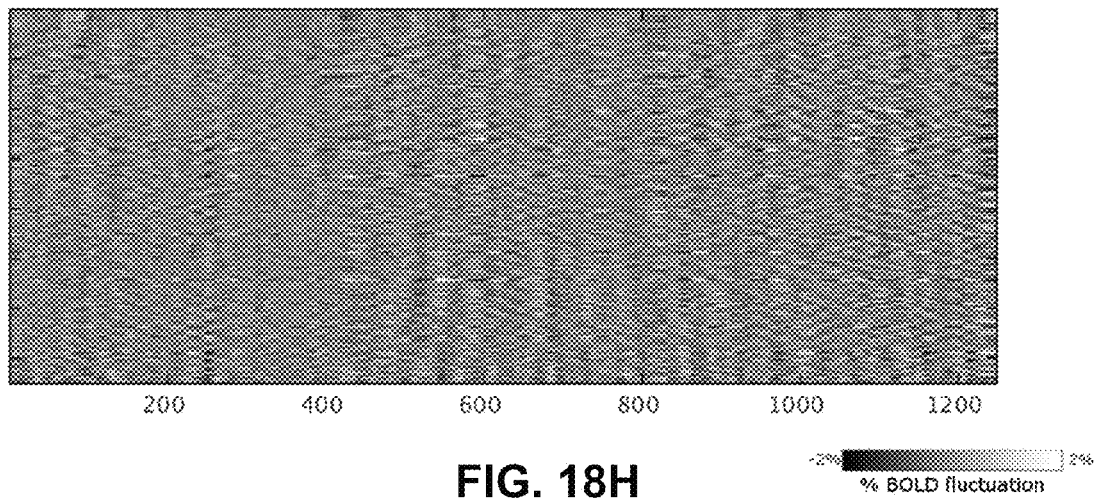
FIG. 18H is a voxel-wise map of BOLD signal fluctuations calculated using post-processed rs-fMRI imaging data obtained from a subject after rTMS treatment.

FIGS. 18A, 18B, 18C, and 18D include quality control plots obtained from rs-fMRI imaging data obtained from the subject prior to rTMS treatment, and FIGS. 18E, 18F, 18G, and 18F are corresponding quality control plots obtained from the subject after rTMS treatment. FIGS. 18A and 18E are graphs of the DV (framewise BOLD signal fluctuation) and FD (framewise displacement) as a function of image frame number calculated from the pre-treated subject's pre-corrected rs-fMRI imaging data. FIGS. 18A and 18E are graphs of the DV (framewise BOLD signal fluctuation) and FD (framewise displacement) as a function of image frame number calculated from the pre-corrected rs-fMRI imaging data obtained from the pre-treated (FIG. 18A) and post-treated (FIG. 18E) subject. FIG. 18B and FIG. 18F are graphs of DV and FD obtained using post-processed rs-fMRI imaging data obtained from the pre-treated (FIG. 18B) and post-treated (FIG. 18F). FIGS. 18C and 18G are total framewise BOLD fluctuation maps calculated from the pre-corrected rs-fMRI imaging data obtained from the pre-treated (FIG. 18C) and post-treated (FIG. 18G) subject. FIGS. 18D and 18H are total framewise BOLD fluctuation maps calculated from the post-corrected rs-fMRI imaging data obtained from the pre-treated (FIG. 18D) and post-treated (FIG. 18H) subject. For the total framewise BOLD fluctuation maps, the x-axis represents frame number and the y-axis represents the total framewise BOLD fluctuation for each of the 147,456 voxels in the image.

DV (framewise BOLD signal fluctuation) and association between DV and FD (framewise displacement) were reduced for the post-processed rs-fMRI imaging data (FIG. 18B and FIG. 18F) relative to the pre-processed rs-fMRI imaging data (FIG. 18A and FIG. 18E). Voxel-wise BOLD signal fluctuations were also reduced for the post-processed rs-fMRI imaging data (FIG. 18D and FIG. 18H) relative to the pre-processed rs-fMRI imaging data (FIG. 18C and FIG. 18G).

Individualized rs-fMRI functional mapping was obtained using the post-corrected rs-fMRI imaging data according to a supervised classification method using a multilayer perceptron (MLP) as described herein above. BOLD time courses were used to construct individual-level resting-state network maps via the multilayer perceptron-based machine learning classifier described above. Briefly, this algorithm classifies each voxel in the BOLD time course into its principal components based on its voxel-wise correlation maps. These components are iteratively refined based on their similarity with a set of reference maps from a trained machine learning algorithm in order to determine the likelihood of each voxel's membership in one of seven cortical networks (dorsal attention, ventral attention/cingulo-opercular, frontoparietal control, default mode, motor, language, and visual).

Based on the individualized cortical network maps obtained as described above, a separate map was computed to visualize the spatial distribution of the absolute difference between dorsal attention network and default mode network. The resulting image was masked to include only voxels within 6 mm of the dural surface, as deeper regions were less accessible via rTMS treatment using the available treatment device. As a liberal approximation of dorsolateral prefrontal cortex, a second mask was applied to include only voxels within 20 mm of previously-reported coordinates for Brodmann areas 9 and 46. Although previous retrospective work has utilized a 25 mm radius, this parameter was less practical for this study due to inclusion of excessively anterolateral regions, which are likely to produce substantial facial muscle contraction in the subject during rTMS treatment. Positive clusters in the resulting image were identified using FSL's cluster algorithm (FMRIB Software Library, Oxford, UK). The centers of gravity of the peak clusters in each hemisphere were selected as the optimal left- and right-sided rTMS stimulation sites. These coordinates were transformed from Talairach to native space using the 4 dfp tool suite.

Figure 19A:
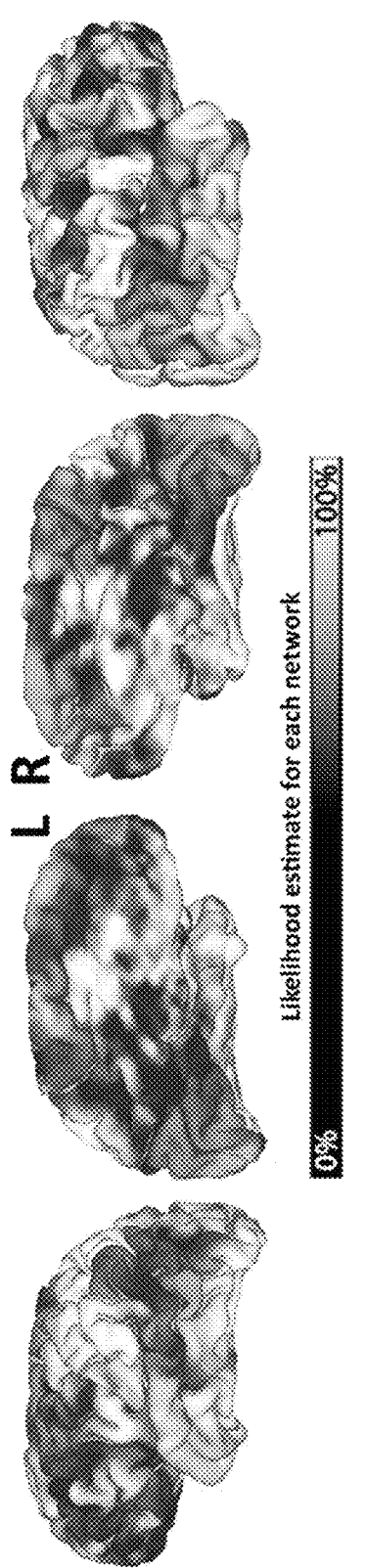
FIG. 19A is an individualized connectome map of voxel-wise likelihood estimates for dorsal attention network membership.
Figure 19B:
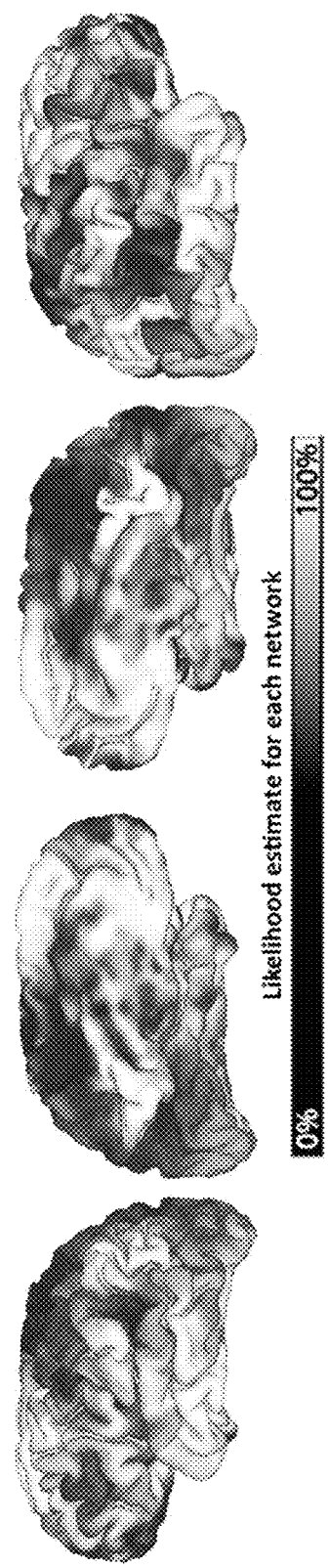
FIG. 19B is an individualized connectome map of voxel-wise likelihood estimates for default mode network membership.
Figure 19C:
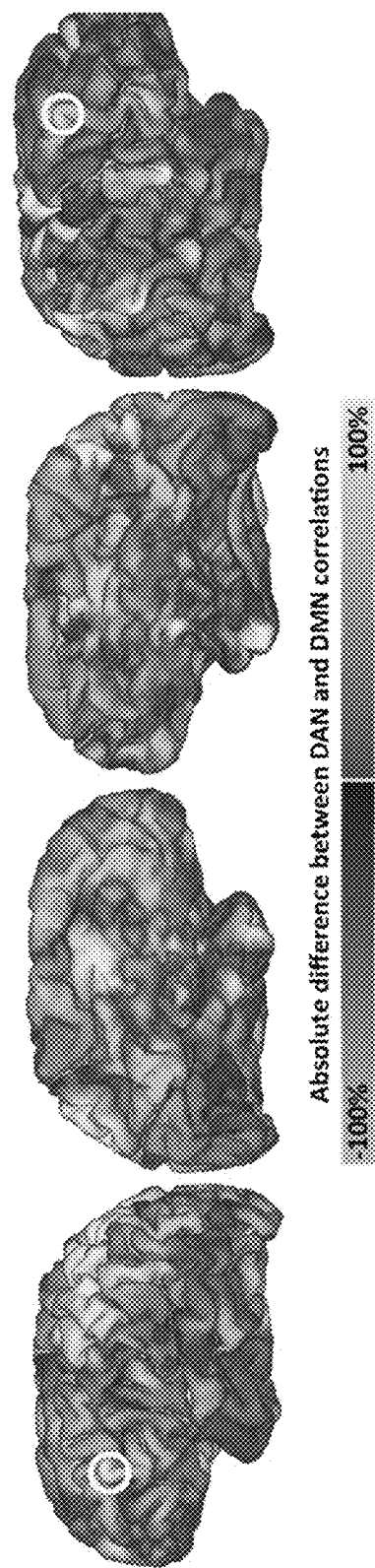
FIG. 19C is a map of the absolute difference between the dorsal attention correlation map illustrated in FIG. 19A and default mode network correlation map illustrated in FIG. 19B.

FIG. 19C is a map of the absolute difference between the dorsal attention correlation map illustrated in FIG. 19A and default mode network correlation map illustrated in FIG. 19B. All maps shown in FIGS. 19A, 19B, and 19C are shown as surface projections on a three-dimensional reconstruction of the subject's anatomical MRI scan. Circled regions overlaid on the maps of FIG. 19C indicate the TMS stimulation sites selected for the subject. The TMS stimulation sites were chosen to be the prefrontal clusters with maximal difference between DAN and DMN correlations according to the difference map shown in FIG. 19C.

The subject received a course of 20 active rTMS treatments at the selected regions over a 4-week period. Each treatment session included 4000 left-sided excitatory pulses and 1000 right-sided inhibitory pulses. Each session of bilateral rTMS included high-frequency left-sided stimulation (4000 pulses at 10 Hz frequency with 5-second trains and 20-second inter-train interval) and low-frequency right-sided stimulation (a single train of 1000 pulses with 1 Hz frequency) with a Magstim Rapid stimulator and 70 mm air-cooled coil. The intensity of rTMS stimulation was 120% of resting motor threshold determined using the TMS Motor Threshold Assessment Tool.

To guide the rTMS device, native-space coordinates were selected on the surface reconstruction of the subject's structural MRI scan using the Brainsight neuronavigation system (Rogue Research, Montreal, Canada). An optimal stimulation trajectory was chosen as a vector perpendicular to the dural surface at the target coordinate. Stimulation was guided along this trajectory using frameless stereotactic neuronavigation. The magnetic coil was adjusted in real-time when the subject's head motion caused greater than 5 mm of displacement from the target, which sometimes required slight modification of the angle between the trajectory vector and the dural surface.

The results of the rTMS treatment of the treatment subject are summarized in Table 4 below. Table 4 includes changes from baseline (pre-treatment) to 6-week post-treatment follow-up in MADRS (primary outcome), personality scores, and self-report emotion scores, as well as changes from baseline to post-treatment in neurocognitive scales, headache scales, and TBI-QoL scales. Secondary outcome variables, including changes in personality scales, neurocognitive scales, and self-report emotion scales, are also summarized in Table 4.

MADRS score improved from 32 at baseline to 9 (72% improvement) immediately after the treatments and remained 9 at six-week follow-up. Cognitive/headache measures showed mild improvement and rTMS treatments were well-tolerated. The subject experienced no seizures, headaches, or other persistent adverse effects. Transient twitching of facial muscles occurred during treatment, but was not associated with pain or persistent discomfort. The subject also incidentally reported a reduction in nicotine cravings, and successfully discontinued cigarette use over the course of the study.

TABLE 4

Neurological Changes Associated with rTMS Treatment.

| Scale | Before | After | 6-week follow-up | Change (post-treatment) | Change (6 week post-treatment) |
|---|---|---|---|---|---|
| MADRS (total score) | 32 | 9 | 9 | −23 (72%) | −23 (72%) |
| TCI (T-score) | | | | | |
| Novelty seeking | 56 | 63 | 56 | 7 | 0 |
| Harm avoidance | 71 | 53 | 65 | −18 | −6 |
| Reward dependence | 25 | 26 | 28 | 1 | 3 |
| Persistence | 3 | 25 | 42 | 22 | 39 |
| Self-directedness | 35 | 42 | 59 | 7 | 24 |
| Cooperativeness | 56 | 52 | 55 | −4 | −1 |
| Self-transcendence | 27 | 22 | 23 | −5 | −4 |
| NIH Toolbox Emotional Battery (T-score) | | | | | |
| Negative Affect Summary | 69 | 57 | 53 | −12 | −16 |
| Social Satisfaction Summary | 29 | 34 | 39 | 5 | 10 |
| Psychological Well Being Summary | 19 | 33 | 39 | 14 | 20 |
| NIH Toolbox Cognitive Battery (T-score) | | | | | |
| Fluid | 40 | 52 | | 12 | |
| Crystallized | 65 | 63 | | −2 | |
| Total | 53 | 57 | | 4 | |

TABLE 4-continued

Neurological Changes Associated with rTMS Treatment.

| Scale | Before | After | 6-week follow-up | Change (post-treatment) | Change (6 week post-treatment) |
|---|---|---|---|---|---|
| Headaches | | | | | |
| HIT6 | 74 | 64 | | −10 | |
| Likert | 5 | 3 | | −2 | |
| TBI-QOL | | | | | |
| Anger | 70 | 47 | | −23 | |
| Anxiety | 72 | 54 | | −18 | |
| Depression | 70 | 46 | | −24 | |
| Emotional/behavioral dyscontrol | 66 | 52 | | −14 | |
| Executive function | 22 | 36 | | 14 | |

Example 2: Comparison of rTMS Treatment Targeting Using rs-fMRI Functional Mapping with Existing Treatment Targeting Methods To identify similarities and differences between the brain regions identified for rTMS treatment using the methods described in Ex. 1 above to existing treatment targeting methods, the following experiments were conducted.

The spatial coordinates targeted for rTMS treatment determined in Ex. 1 were compared to corresponding target coordinates determined using three previously-described methods: "5 cm rule" targeting, structural MRI-based targeting, and individualized anti-sgACC targeting.

The target coordinates determined by the 5 cm rule targeting method were published estimates of coordinate values from a previous study of rTMS targeting. As previously described, this method utilizes a target that is 5 cm anterior to a location in the motor cortex at which single-pulse TMS stimulation leads to contraction of the contralateral abductor pollicis brevis muscle. The 5 cm rule targeting method is an empirical method that remains widely used in the clinical setting.

The target coordinates determined by the structural MRI-based targeting method utilized dorsolateral prefrontal coordinates that have been used previously for targeting at a large-scale neuronavigated rTMS clinic. Without being limited to any particular theory, recent consensus among rTMS clinical practitioners is converging towards the use of targeting coordinates in which a group-mean connectivity analysis indicates maximum anticorrelation of the targeted region with the subgenual anterior cingulate cortex (sgACC).

Figure 20:
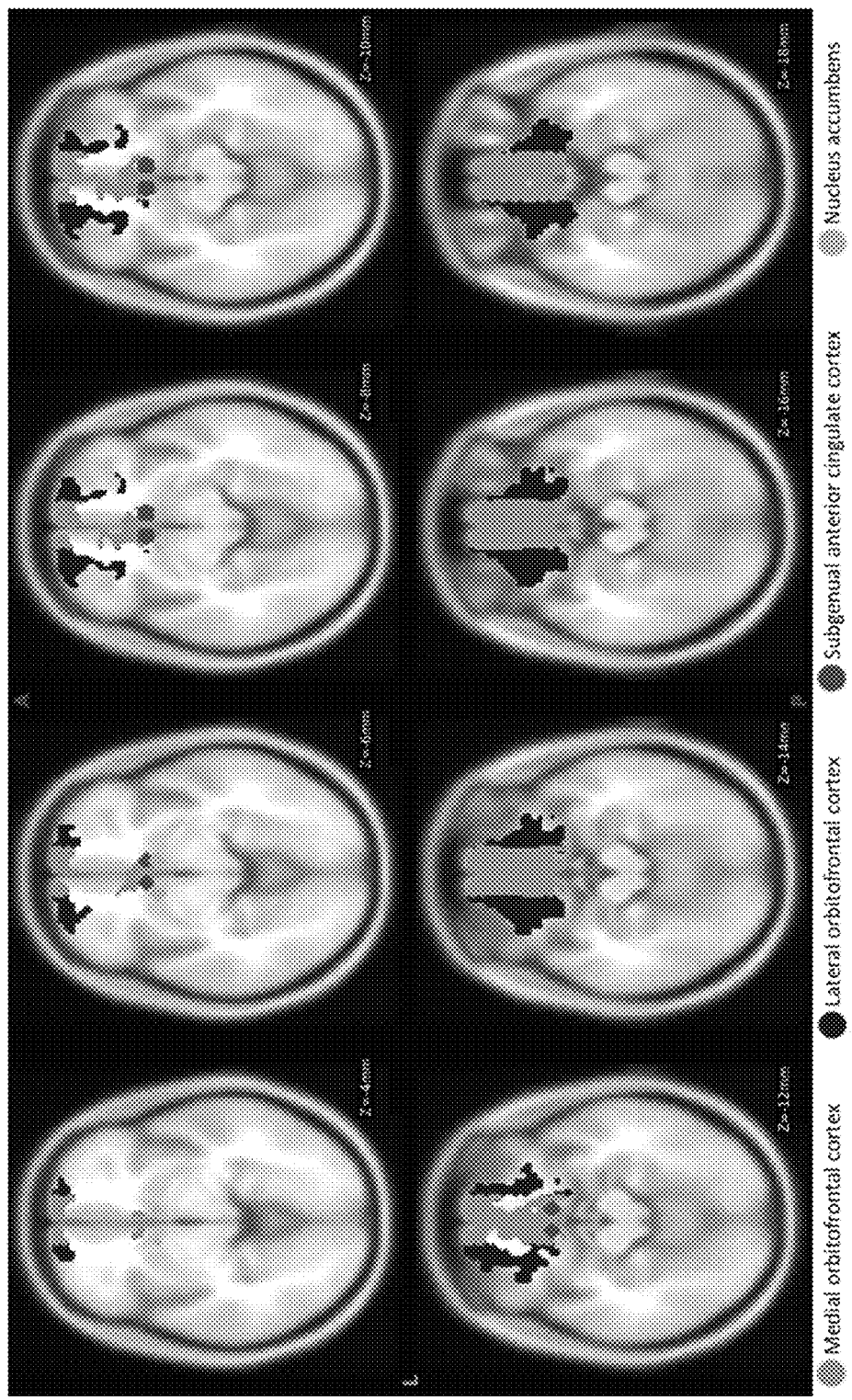
FIG. 20 is a series of images showing the spatial extent of four group-based ROIs used for seed-based connectivity analysis: medial orbitofrontal cortex (mOFC), lateral orbitofrontal cortex (lOFC), subgenual anterior cingulate cortex (sgACC), and nucleus accumbens (NAcc); all of four group-based ROIs were based on previously published data.

The target coordinates determined by the individualized anti-sgACC targeting method made use of an individual subject's anti-correlation with a group-mean definition of the sgACC. A whole-brain correlation map was produced for the rTMS-treated subject using the pre-treatment rs-fMRI data and the previously-published coordinates of a seed region representative of the sgACC seed region representative of the sgACC, shown as red-shaded regions in FIG. 20. The whole-brain correlation map was masked to include only cortical regions within 20 mm of previously-reported coordinates for Brodmann areas 9 and 46. All values in the resulting masked correlation map were multiplied by −1 in order to identify anti-correlations rather than correlations. A peak cluster was identified using FSL's cluster algorithm, and the center of this identified cluster was identified as the "anti-sgACC" rs-fMRI-based target.

All targeting coordinates identified using the methods described above were transformed into a common Talairach atlas space to provide a consistent basis for comparison. The spatial distances between the left and right targeting coordinates identified in Ex. 1 and the targeting coordinates calculated using the three previously-published methods described above were calculated to quantify the consistency of the targeting coordinates determined by the various methods. Table 5 below summarizes the results of this comparison.

TABLE 5

Comparison of Targeting Coordinates for Treatment

| Targeting Method | Supervised Classifier with Perceptron | Standard 5 cm | Structural | Anti-sgACC |
|---|---|---|---|---|
| Left Side Target Coordinates | (−45, 39, 21) | (−41, 54, 12) | (−38, 44, 26) | (−40, 18, 49) |
| Distance from Supervised Classifier with Perceptron | 0 | 18 mm | 10 mm | 36 mm |
| Right Side Target Coordinates | (43, 39, 28) | (41, 45, 24) | (38, 44, 26) | (40, 18, 49) |
| Distance from Supervised Classifier with Perceptron | 0 | 8 mm | 7 mm | 30 mm |

Figure 21:
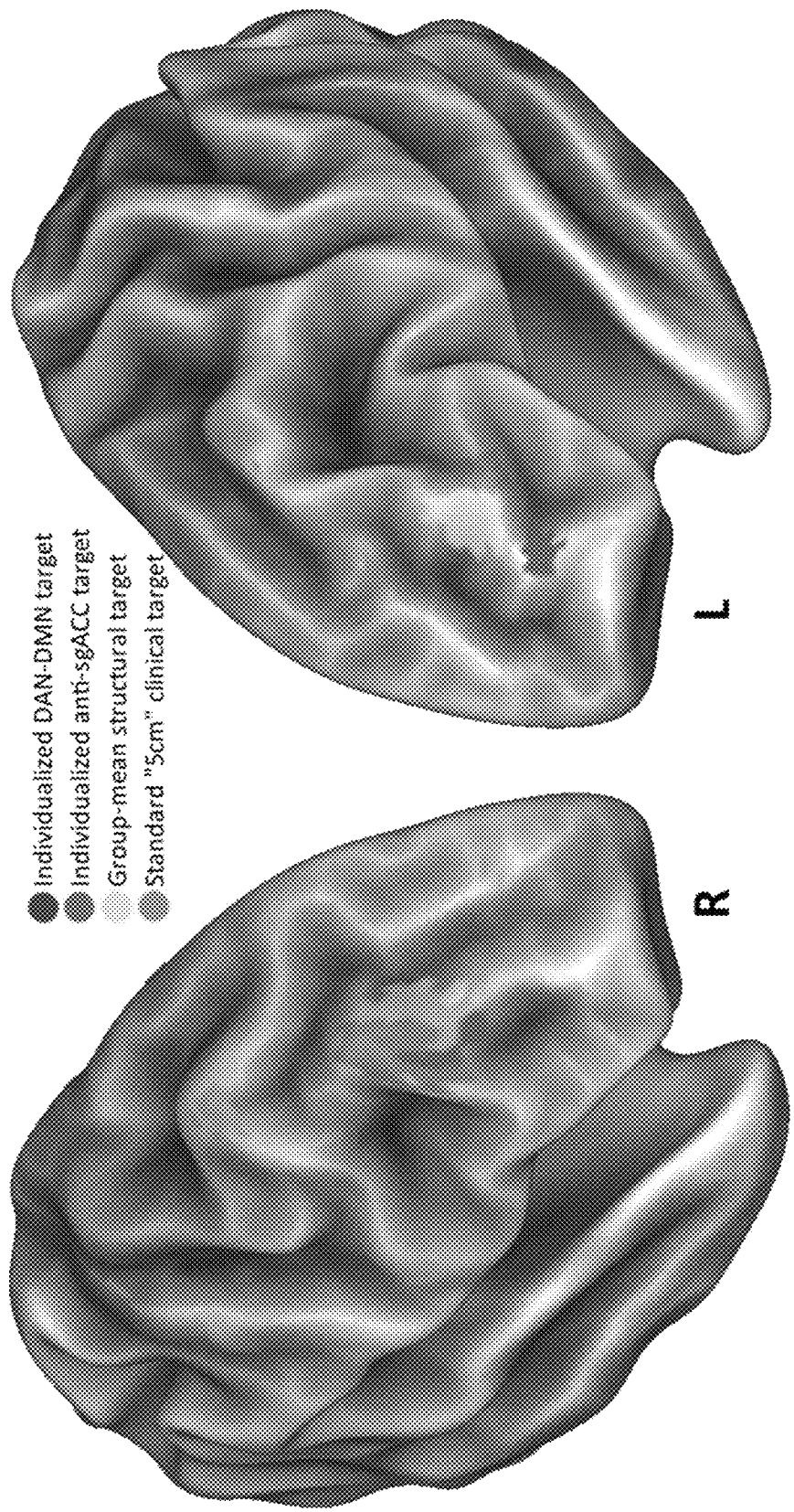
FIG. 21 includes images illustrating the anatomical locations of targeting regions generated by using individualized resting-state network mapping according to an aspect of the disclosure, a clinical "5-cm rule" targeting method, a structural MRI-based targeting method, and an individualized anti-sgACC targeting method.

FIG. 21 contains images illustrating the anatomical locations of targets generated using individualized resting-state network mapping method described in Ex. 1, the individualized sgACC anticorrelation method, the group-mean structural targeting method, and traditional clinical "5-cm rule" targeting method. The colored patches superimposed over the structural/anatomical brain images represent an estimated TMS stimulation volume based on spatial distribution of cortical regions within 15 mm of each target. All estimated TMS stimulation volumes were projected onto a surface reconstruction generated from the subject's anatomical T1-weighted scan.

The identified left- and right-sided rTMS targets were 36 mm and 30 mm away from traditional 5 cm rule clinical targets for major depression. They were 10-18 mm and 7-8 mm away from targets identified by previously-described imaging-based targeting methods.

Individualized rTMS targets determined using the individualized resting-state network mapping method described in Ex. 1 were anatomically distinct from the treatment targets generated by prior approaches. A limited amount of overlap between the expected stimulation volumes from the imaging-based targeting approaches was observed for the right side of the brain, but a spatial distinction remained evident. On the left side of the brain, there was minimal overlap of expected stimulation volume determined using the different targeting approaches. All of the imaging-based targeting approaches resulted in expected stimulation volumes that were distinct from the clinical "5 cm" rule target sites.

Example 3: Comparison of Cortical Parcellation of TBI and Normal Subjects

To assess differences in the functional maps of the rTMS-treated subject and normal subjects described in Ex. 1 obtained using the methods described in Ex. 1, the following experiments were conducted.

Using the voxel-wise estimates for each of the seven individualized resting-state network maps obtained as described in Ex. 1, each voxel was assigned to the network with which it exhibited the maximum likelihood of membership. These values were used to construct a winner-take-all map of cortical parcels.

Figure 22A:
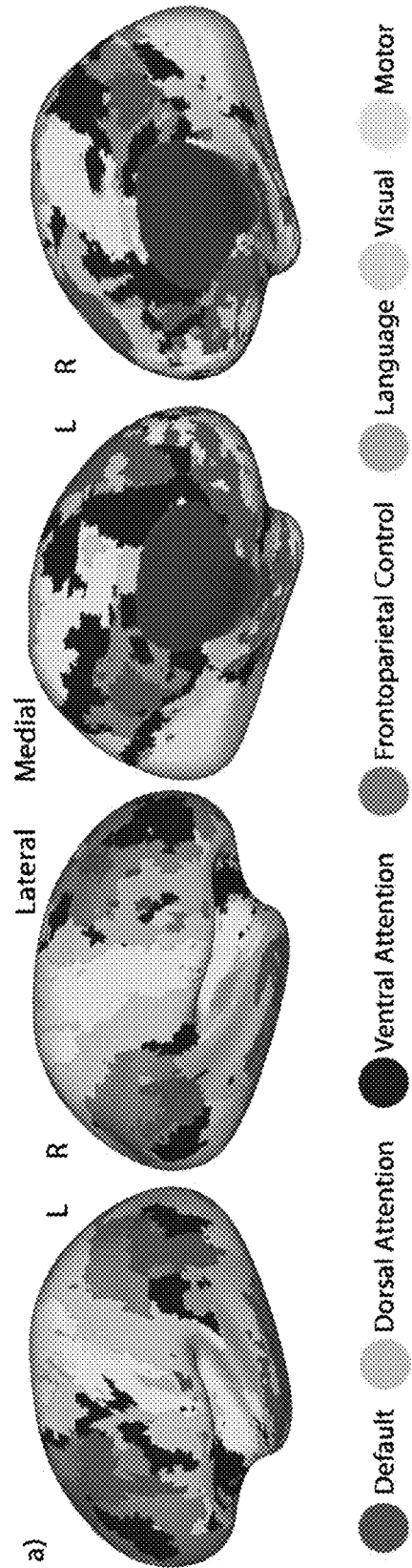
FIG. 22A contains images showing winner-take-all maps of individualized resting-state network parcellation obtained for a subject exposed to traumatic brain injury.
Figure 22B:
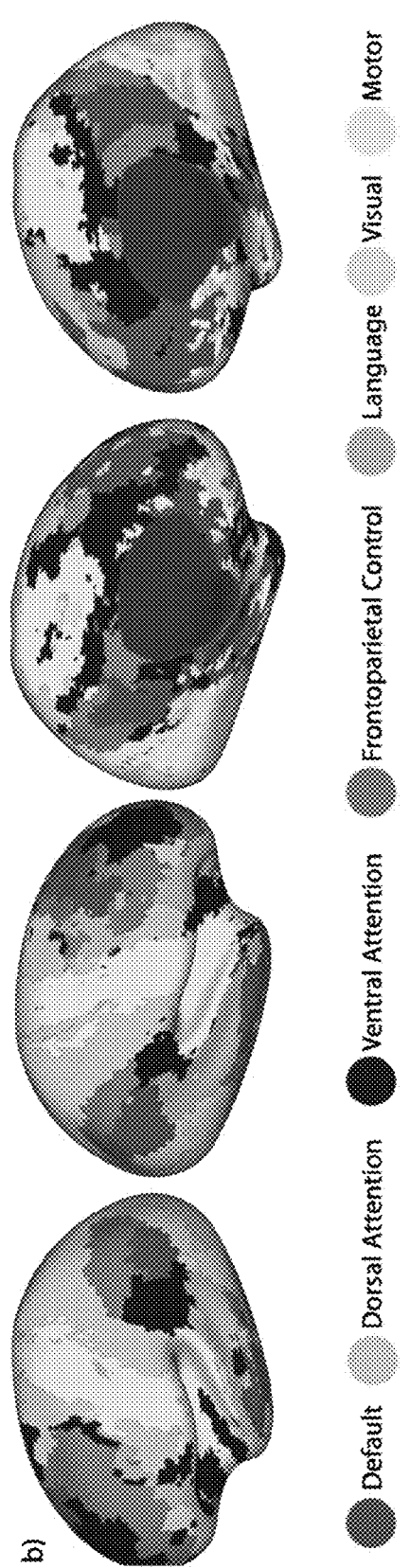
FIG. 22B contains images showing winner-take-all maps of individualized resting-state network parcellation obtained using mean values of a group of healthy control subjects.
Figure 22C:
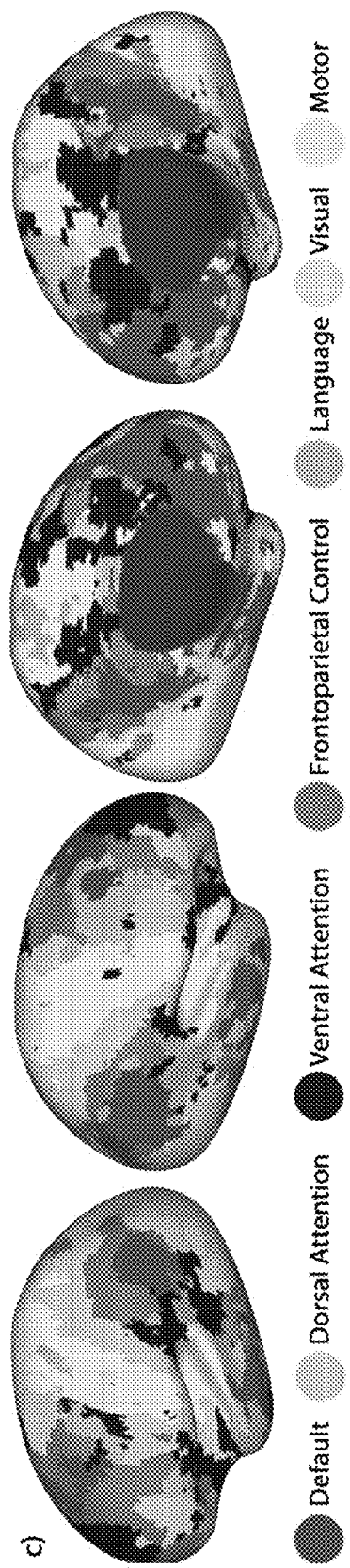
FIG. 22C contains images showing winner-take-all maps of individualized resting-state network parcellation obtained for a representative example of a healthy control subject.

FIGS. 22A, 22B, and 22C are images showing winner-take-all maps of individualized resting-state network parcellation obtained for the rTMS-treated subject (FIG. 22A), the group mean of healthy controls (FIG. 22B), and a representative example of a healthy control subject (FIG. 22C). For visualization, maps are projected onto a mean inflated surface from the Human Connectome Project.

The rTMS-treated subject's baseline individual-level parcellation revealed atypical findings in location, size, and left-right symmetry of dorsal attention, ventral attention, frontoparietal, and default mode networks. In comparison with healthy controls, the rTMS-treated subject's baseline individual-level parcellation revealed differences in location, size, and left-right symmetry of dorsal attention, ventral attention, frontoparietal, and default mode networks, particularly in the prefrontal cortex. Due to this spatial variability, these individual subject parcels were used for ROI-based connectivity analysis described below in order to achieve enhanced individualized precision relative to previous methods that made use of group-mean parcellations.

Example 4: Effects of rTMS Treatment of Traumatic Brain Injury-Related Depression on Functional Connectivity To assess the effects of rTMS treatment of a subject with TBI-associated depression on functional connectivity architecture, the following experiments were conducted.

BOLD time courses measured using the methods described in Ex. 1 were analyzed for seed-based functional connectivity by determining correlation matrices between several regions of interest (ROIs), including both individualized parcels and group-mean parcels. The absolute differences in Fisher-transformed ROI-ROI correlations were compared between pre-treatment scans of the rTMS-treated subject, post-treatment scans, and control subjects described in Ex. 1. Seed-based correlation maps for the left- and right-sided rTMS targets were generated for the experimental subject's pre-treatment and post-treatment scans.

Table 6 summarizes the ROIs used to determine the correlation matrices described above, as well as the source by which each ROI was identified.

TABLE 6

ROIs Used for Seed-Based Correlation Analysis

| Region of interest | Identification method |
|---|---|
| Dorsal attention network (DAN) | Subject-specific winner-take-all map (FIG. 22A) |
| Ventral attention network (VAN) | Subject-specific winner-take-all map (FIG. 22A) |
| Default mode network (DMN) | Subject-specific winner-take-all map (FIG. 22A) |
| Medial orbitofrontal cortex (mOFC) | Medial half of parcel 10 from published literature (FIG. 20) |
| Lateral orbitofrontal cortex (lOFC) | Lateral half of parcel 10 from published literature (FIG. 20) |
| Medial temporal lobe (MTL) | Parcel 9 from published literature (FIG. 20) |
| Left/right sgACC | 10-mm sphere at coordinates from published literature (FIG. 20) |
| Left/right nucleus accumbens (NAcc) | 6-mm sphere at coordinates from published literature (FIG. 20) |
| Left/right rTMS target | 15-mm sphere at coordinates generated by TMS targeting algorithm (FIG. 21) |

The comparison of baseline resting-state functional connectivity between specific large-scale networks and cortico-limbic-striatal reward circuits obtained from analysis of pre-treatment scans of the rTMS-treated subject, post-treatment scans of the rTMS-treated subject, and scans of the healthy and TBI-associated depression subjects are summarized in FIGS. 23A, 23B, 23C, 23D, 23E, 23F, 23G, 23H, 23I, 23J, 23K, 23L, 23M, 23N, and 23O.

In comparison with both the healthy and the TBI-associated depression comparator groups, the baseline rs-fMRI revealed near-absence of the typical DAN-DMN anticorrelation (see FIG. 23O) and changes in limbic connectivity with nucleus accumbens (NAcc). Limbic-NAcc connectivity patterns were partly normalized with rTMS treatment (see FIG. 23J).

Figures 23A, 23B:
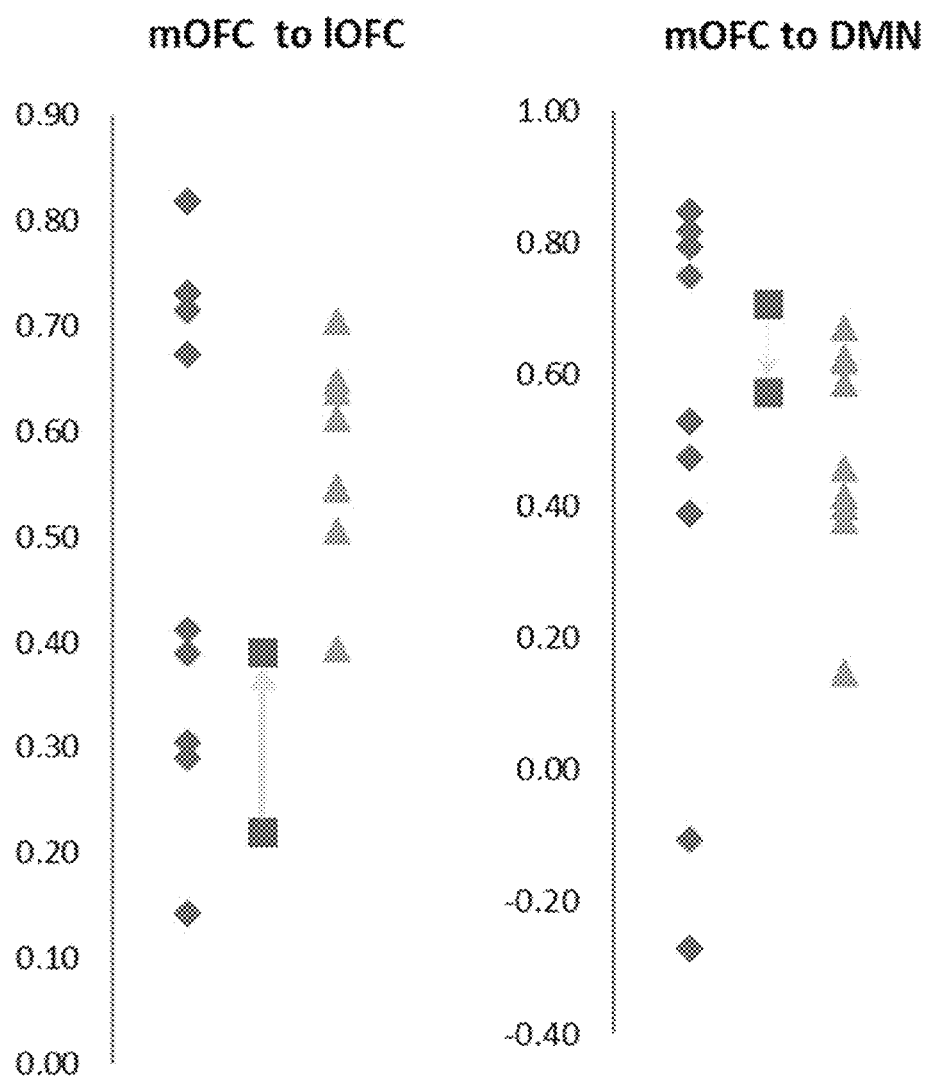
FIG. 23A is a graph comparing pre- and post-treatment mOFC-lOFC ROI correlations for a subject treated for traumatic brain injury-related depression using rTMS with baseline correlations for healthy controls and for comparator subjects with untreated TBI-associated depression.
FIG. 23B is a graph comparing pre- and post-treatment mOFC-DMN ROI correlations for a subject treated for traumatic brain injury-related depression using rTMS with baseline correlations for healthy controls and for comparator subjects with untreated TBI-associated depression.
Figures 23C, 23D:
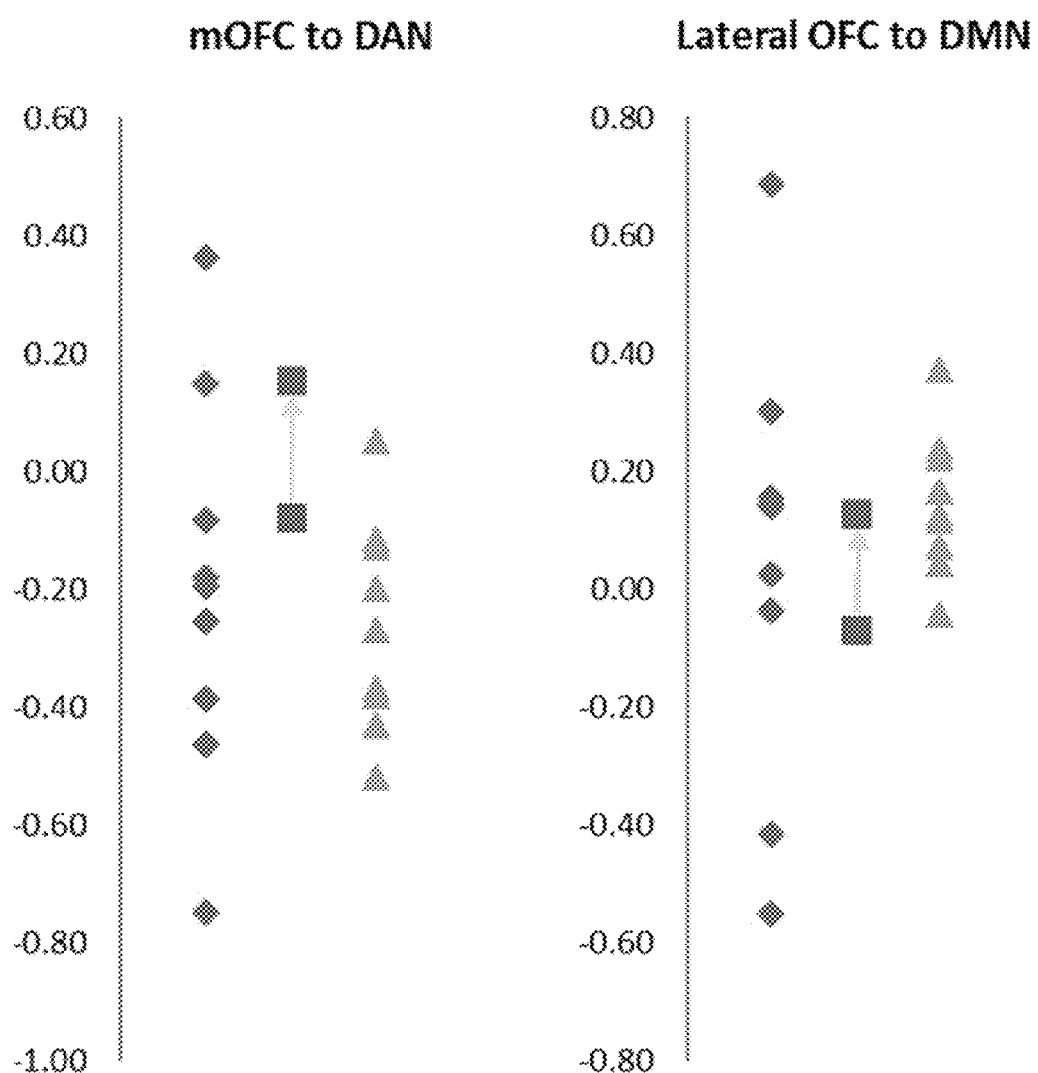
FIG. 23C is a graph comparing pre- and post-treatment mOFC-DAN ROI correlations for a subject treated for traumatic brain injury-related depression using rTMS with baseline correlations for healthy controls and for comparator subjects with untreated TBI-associated depression.
FIG. 23D is a graph comparing pre- and post-treatment lOFC-DMN ROI correlations for a subject treated for traumatic brain injury-related depression using rTMS with baseline correlations for healthy controls and for comparator subjects with untreated TBI-associated depression.
Figures 23E, 23F:
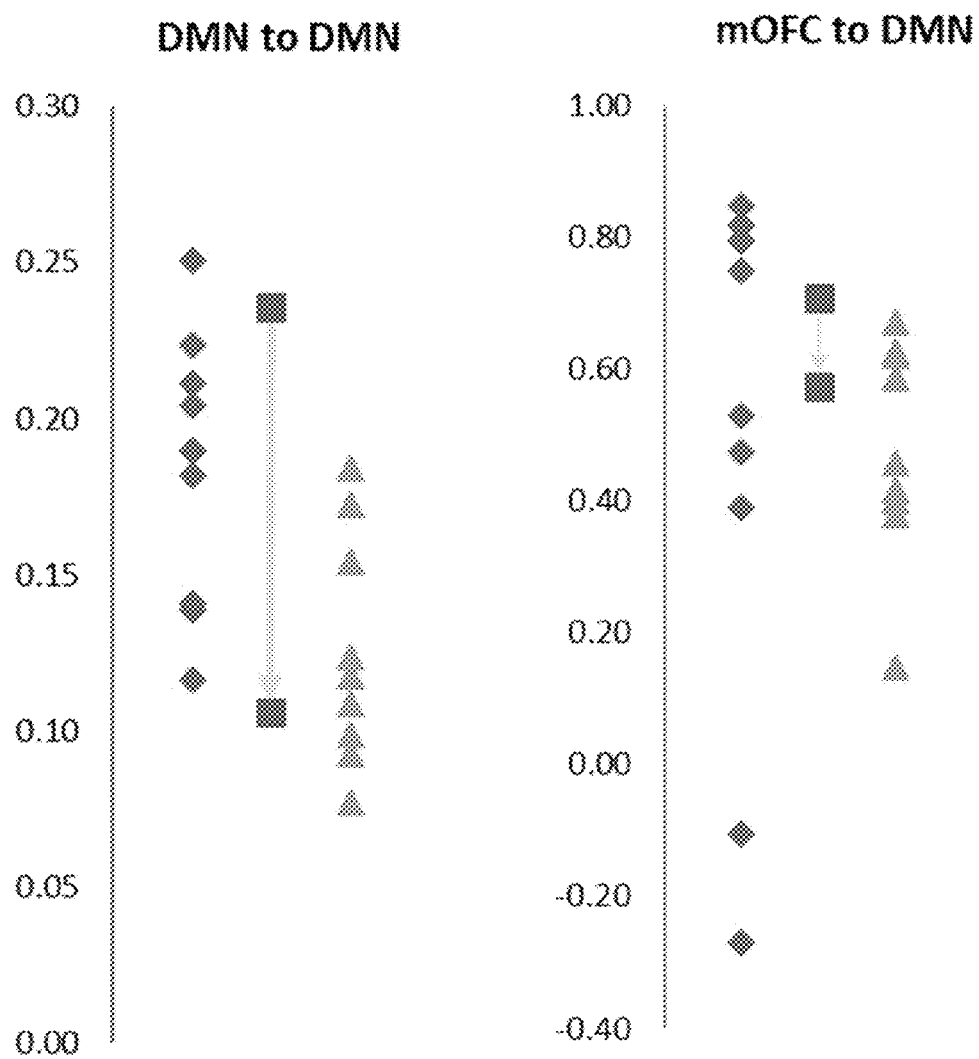
FIG. 23E is a graph comparing pre- and post-treatment DMN-DMN ROI correlations for a subject treated for traumatic brain injury-related depression using rTMS with baseline correlations for healthy controls and for comparator subjects with untreated TBI-associated depression.
FIG. 23F is a graph comparing pre- and post-treatment mOFC-DMN ROI correlations for a subject treated for traumatic brain injury-related depression using rTMS with baseline correlations for healthy controls and for comparator subjects with untreated TBI-associated depression.
Figures 23G, 23H:
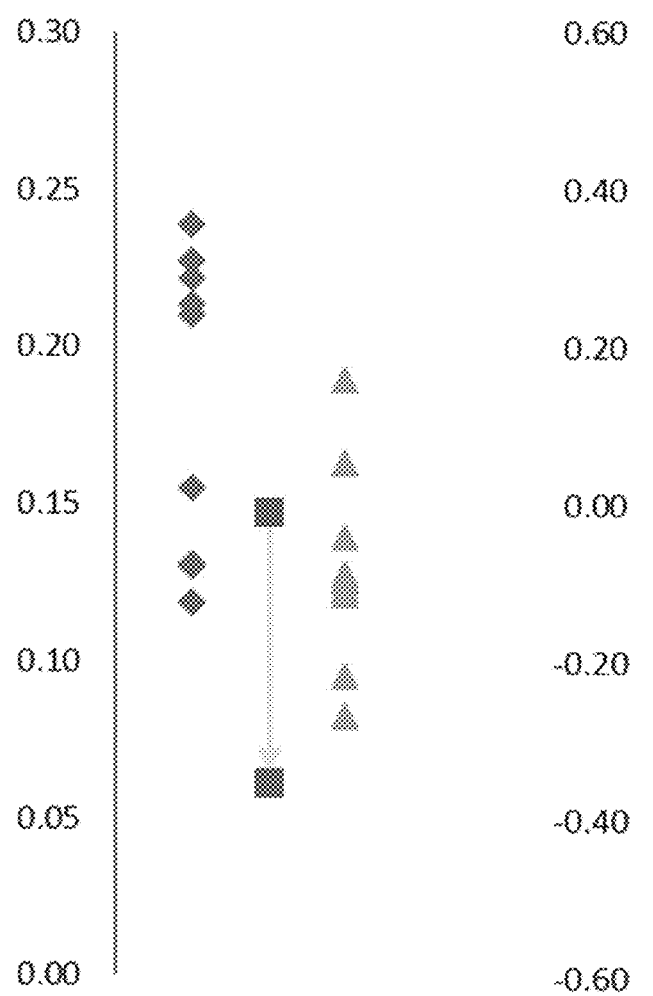
FIG. 23G is a graph comparing pre- and post-treatment DAN-DAN ROI correlations for a subject treated for traumatic brain injury-related depression using rTMS with baseline correlations for healthy controls and for comparator subjects with untreated TBI-associated depression.
FIG. 23H is a graph comparing pre- and post-treatment DAN-VAN ROI correlations for a subject treated for traumatic brain injury-related depression using rTMS with baseline correlations for healthy controls and for comparator subjects with untreated TBI-associated depression.
Figures 23I, 23J:
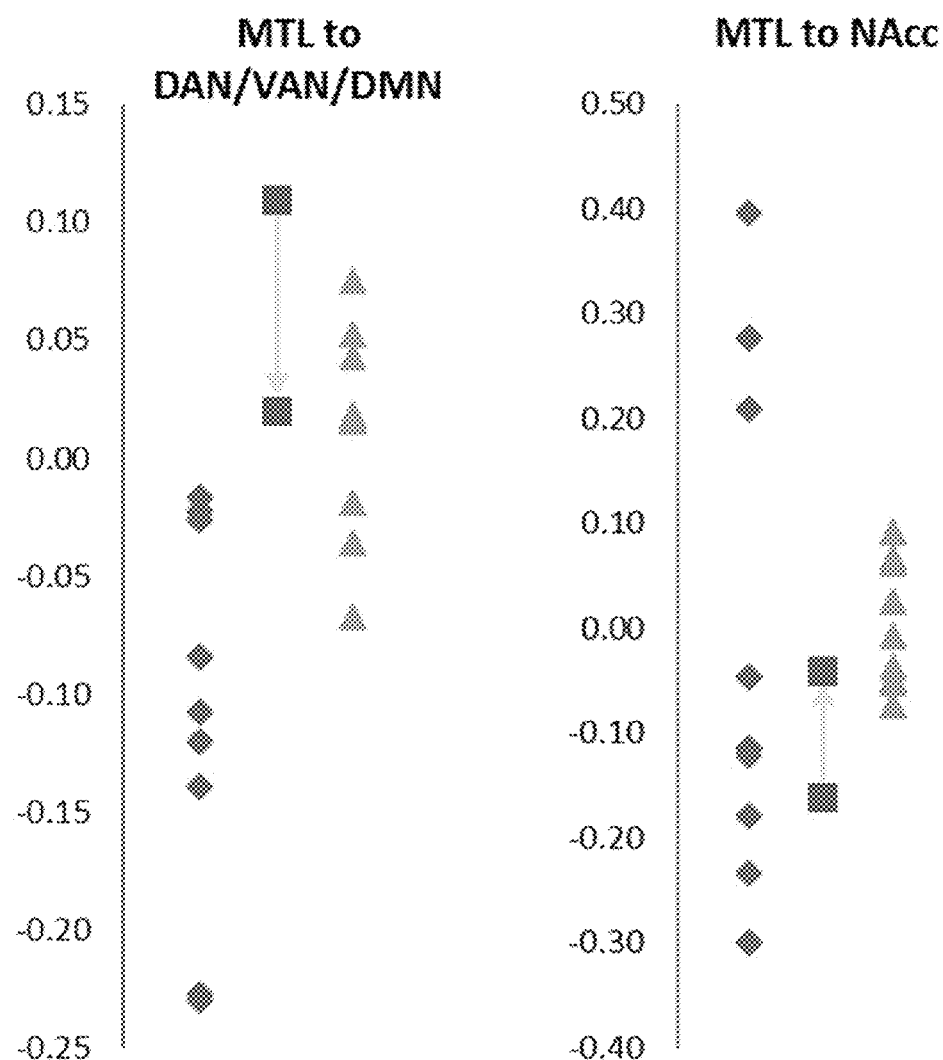
FIG. 23I is a graph comparing pre- and post-treatment MTL-DAN/VAN/DMN ROI correlations for a subject treated for traumatic brain injury-related depression using rTMS with baseline correlations for healthy controls and for comparator subjects with untreated TBI-associated depression.
FIG. 23J is a graph comparing pre- and post-treatment MTL-NAcc ROI correlations for a subject treated for traumatic brain injury-related depression using rTMS with baseline correlations for healthy controls and for comparator subjects with untreated TBI-associated depression.
Figures 23K, 23L:
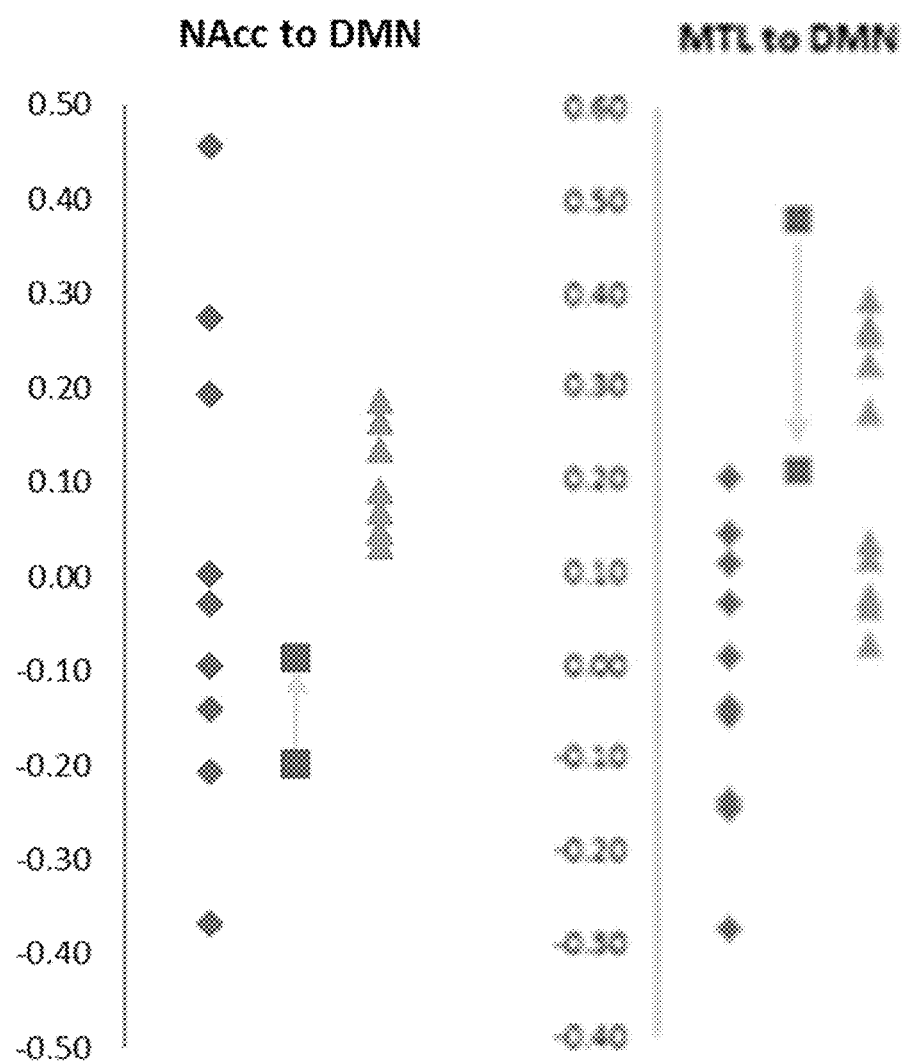
FIG. 23K is a graph comparing pre- and post-treatment NAcc-DMN ROI correlations for a subject treated for traumatic brain injury-related depression using rTMS with baseline correlations for healthy controls and for comparator subjects with untreated TBI-associated depression.
FIG. 23L is a graph comparing pre- and post-treatment MTL-DMN ROI correlations for a subject treated for traumatic brain injury-related depression using rTMS with baseline correlations for healthy controls and for comparator subjects with untreated TBI-associated depression.
Figures 23M, 23N:
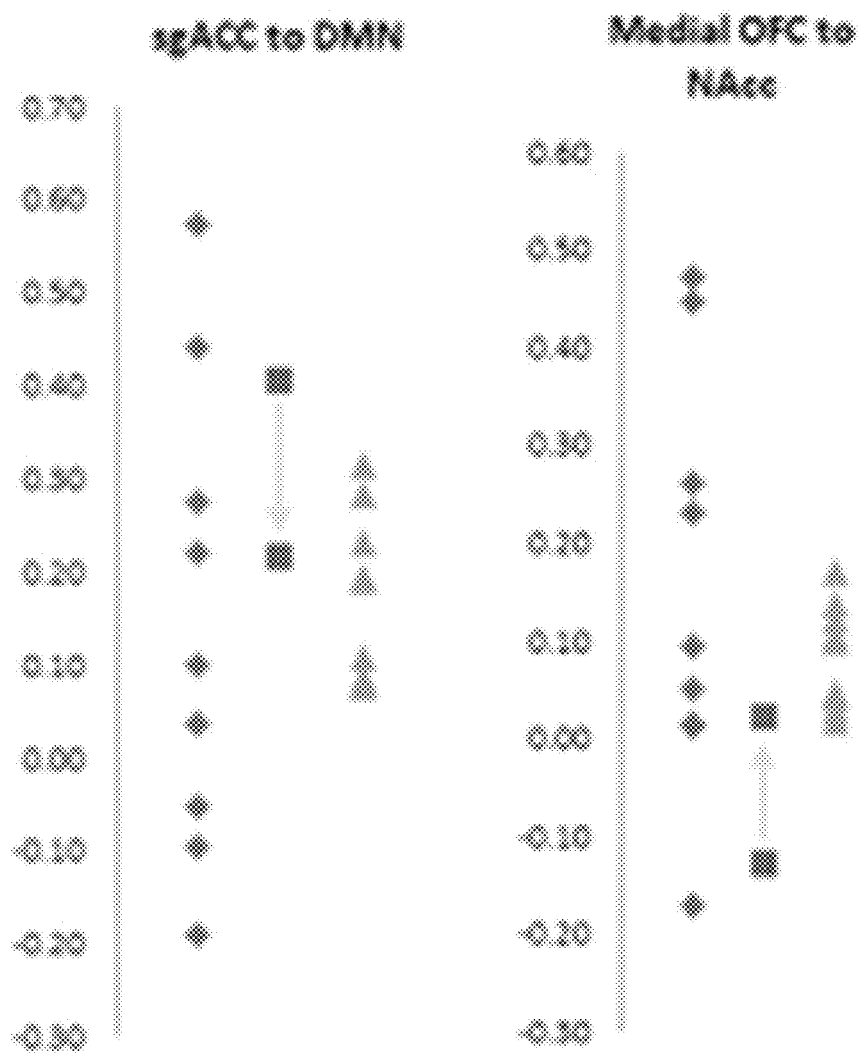
FIG. 23M is a graph comparing pre- and post-treatment sgACC-DMN ROI correlations for a subject treated for traumatic brain injury-related depression using rTMS with baseline correlations for healthy controls and for comparator subjects with untreated TBI-associated depression.
FIG. 23N is a graph comparing pre- and post-treatment mOFC-NAcc ROI correlations for a subject treated for traumatic brain injury-related depression using rTMS with baseline correlations for healthy controls and for comparator subjects with untreated TBI-associated depression.
Figure 23O:
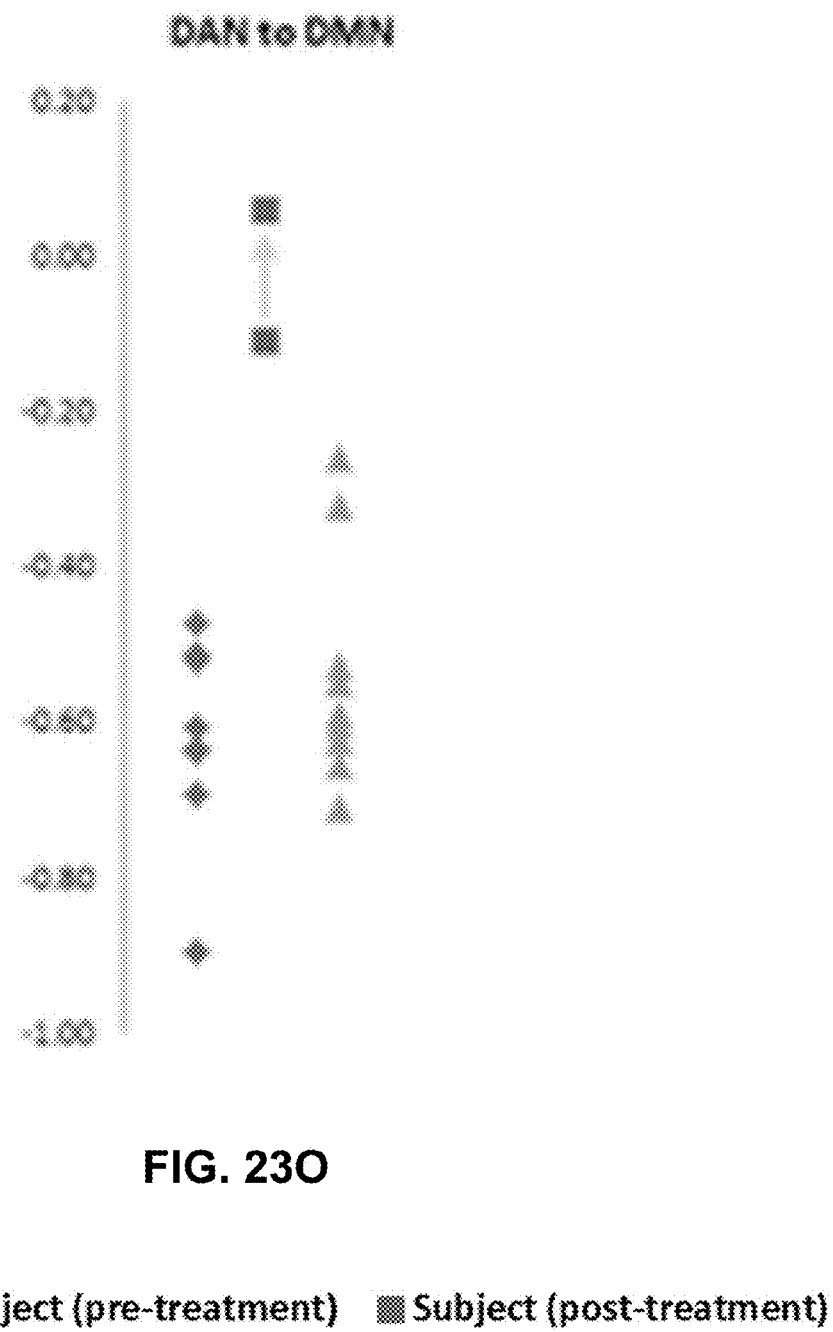
FIG. 23O is a graph comparing pre- and post-treatment DAN-DMN ROI correlations for a subject treated for traumatic brain injury-related depression using rTMS with baseline correlations for healthy controls and for comparator subjects with untreated TBI-associated depression.

Baseline seed-based connectivity analysis revealed several correlation coefficients that were outside the corresponding range of healthy controls. Some correlation coefficients, including MTL to DMN (FIG. 23L), MTL to DAN/VAN/DMN (FIG. 23I), and DAN to DMN (FIG. 23O) were also outside the range of comparator subjects with TBI-associated depression. MTL to DMN and MTL to DAN/VAN/DMN correlations normalized with treatment, although DAN to DMN became more abnormal after treatment. Furthermore, voxel-wise DAN to DAN connectivity (FIG. 23G) was within the normal range before treatment, but became lower than all controls or comparator TBI-associated depression subjects after treatment. Treatment additionally led to normalization of hyperconnectivity between subgenual anterior cingulate cortex (sgACC) and DMN (FIG. 23M) as well as normalization of hypoconnectivity between medial orbitofrontal cortex (mOFC) and nucleus accumbens (NAcc) (FIG. 23N).

In addition, maps of whole-brain seed-to-voxel connectivity with the left-sided stimulation site and the right-sided stimulation site as described in Ex. 1 were generated for the rTMS-treated subject based on pre-treatment rs-fMRI data, and post-treatment rs-fMRI data using methods similar to the methods described in Ex. 1 to further assess changes in function map architecture as a result of the rTMS treatment.

Figure 24A:
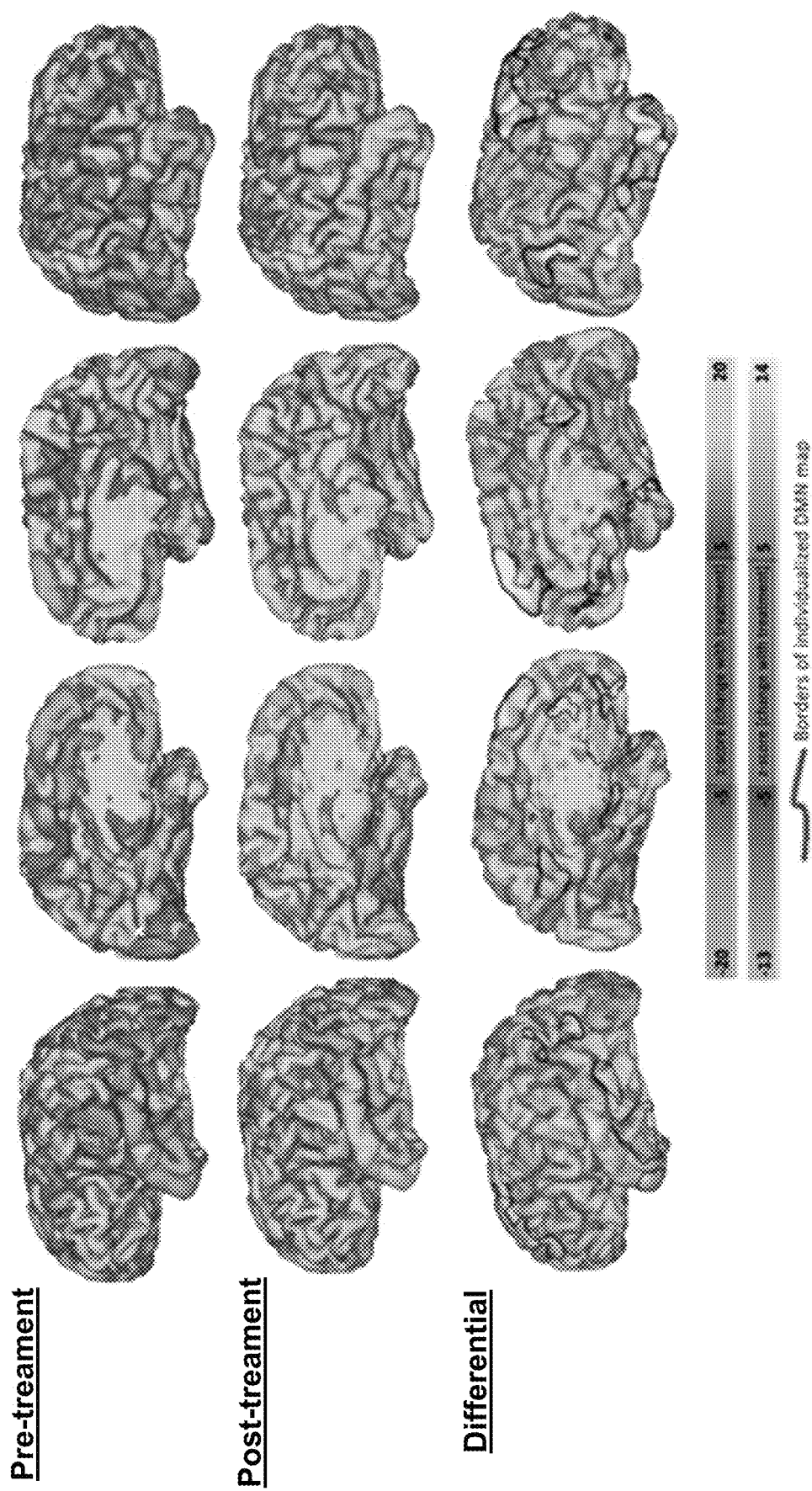
FIG. 24A contains images showing whole-brain connectivity maps of seed-based correlation with a 15-mm spherical ROI at a left-sided rTMS target before and after rTMS treatment.
Figure 24B:
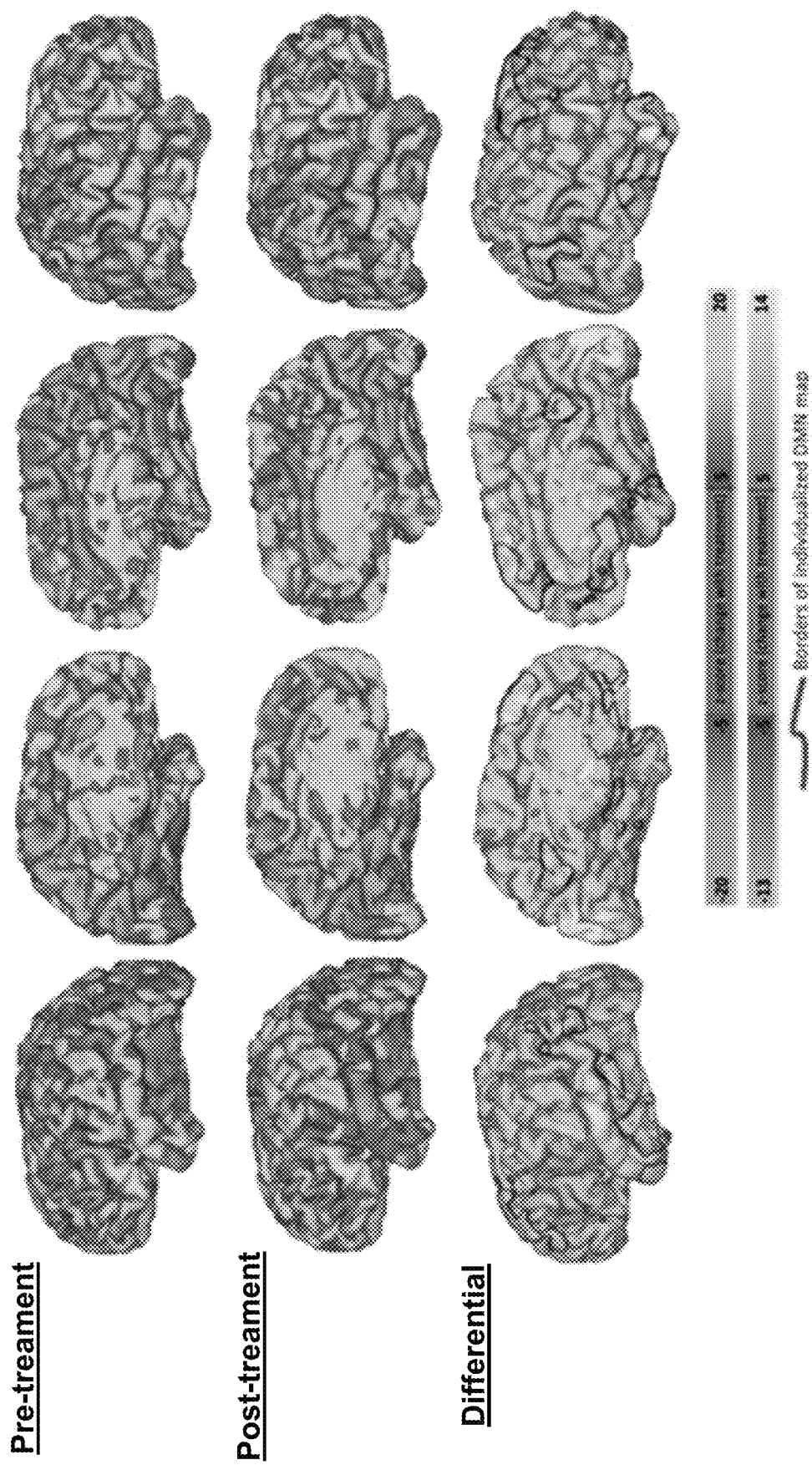
FIG. 24B contains images showing whole-brain connectivity maps of seed-based correlation with a 15-mm spherical ROI at a right-sided rTMS target before and after rTMS treatment.
Figure 25A:
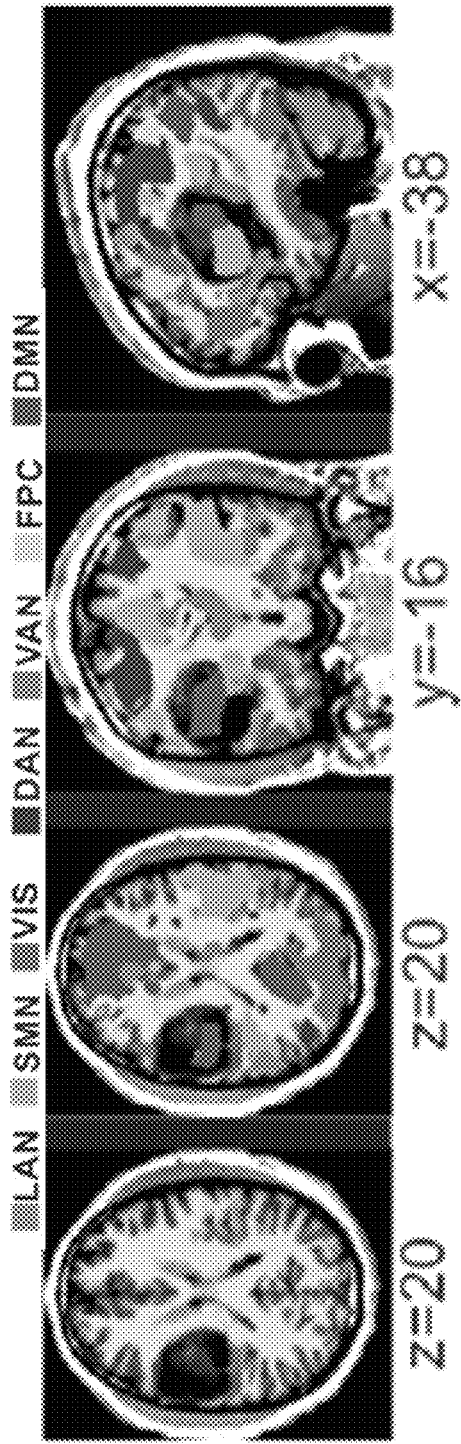
FIG. 25A is a series of resting state network (RSN) maps of a first patient with brain tumor produced using a multi-level perceptron RSN mapping method according to one aspect of the disclosure.
Figure 25B:
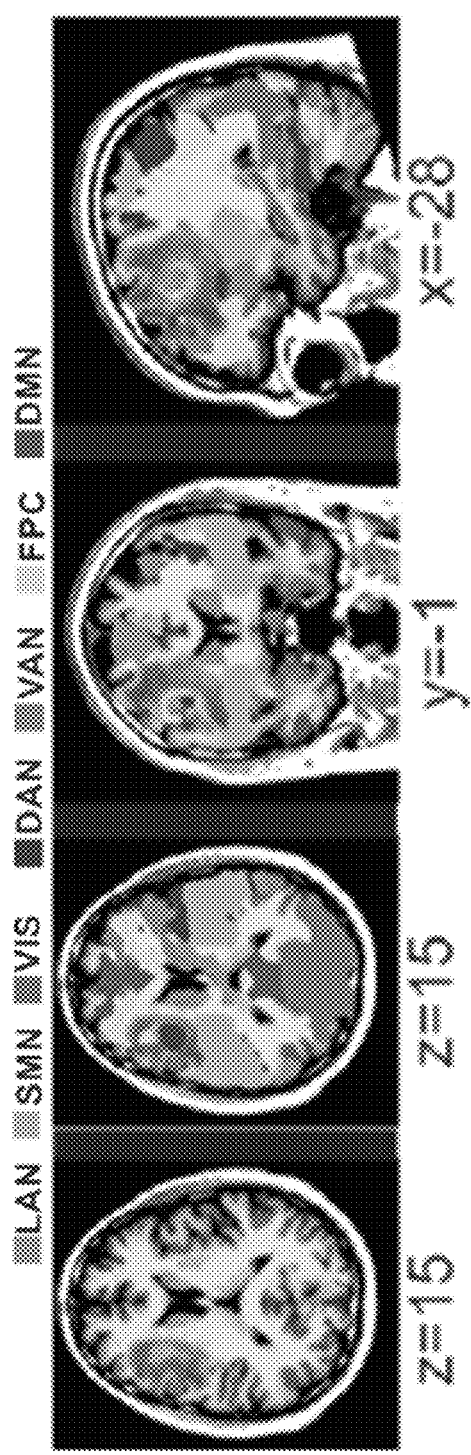
FIG. 25B is a series of resting state network (RSN) maps of a second patient with brain tumor produced using a multi-level perceptron RSN mapping method according to one aspect of the disclosure.
Figure 25C:
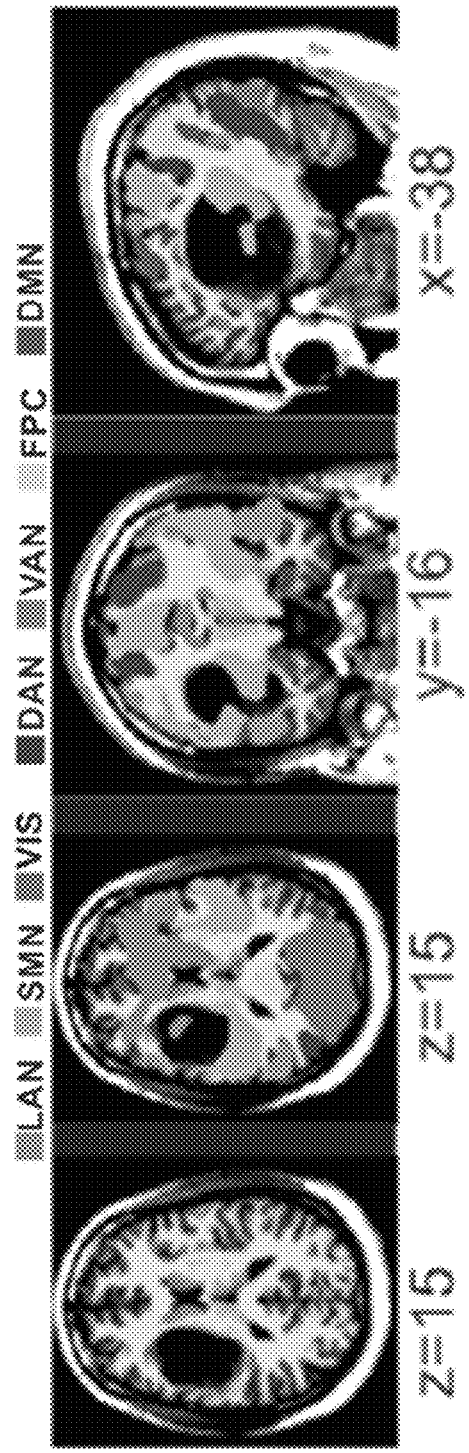
FIG. 25C is a series of resting state network (RSN) maps of a third patient with brain tumor produced using a multi-level perceptron RSN mapping method according to one aspect of the disclosure.
Figure 25D:
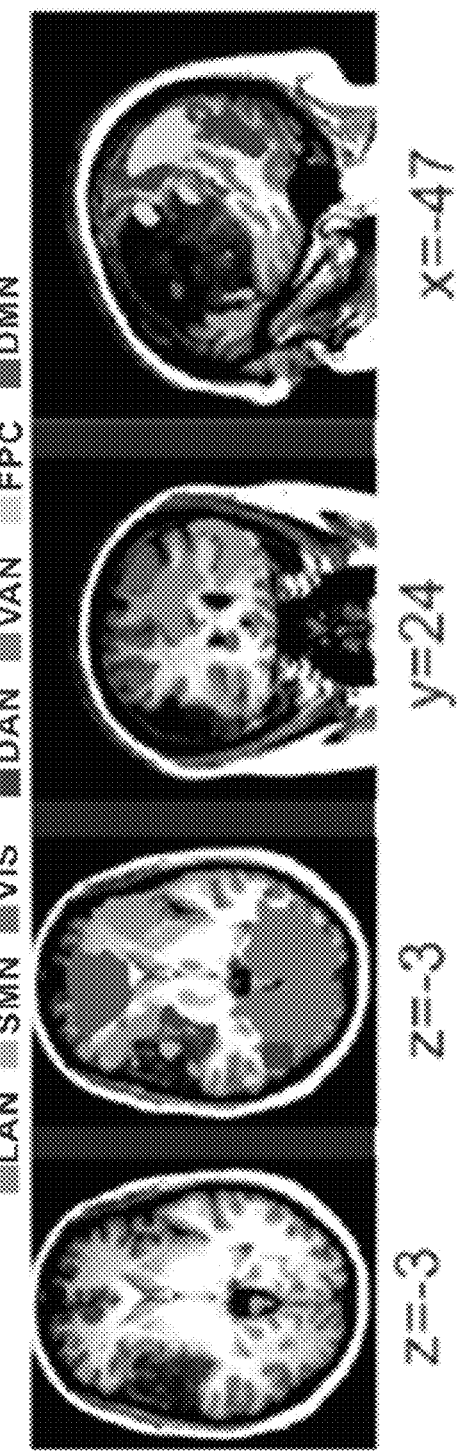
FIG. 25D is a series of resting state network (RSN) maps of a fourth patient with brain tumor produced using a multi-level perceptron RSN mapping method according to one aspect of the disclosure.
Figure 25E:
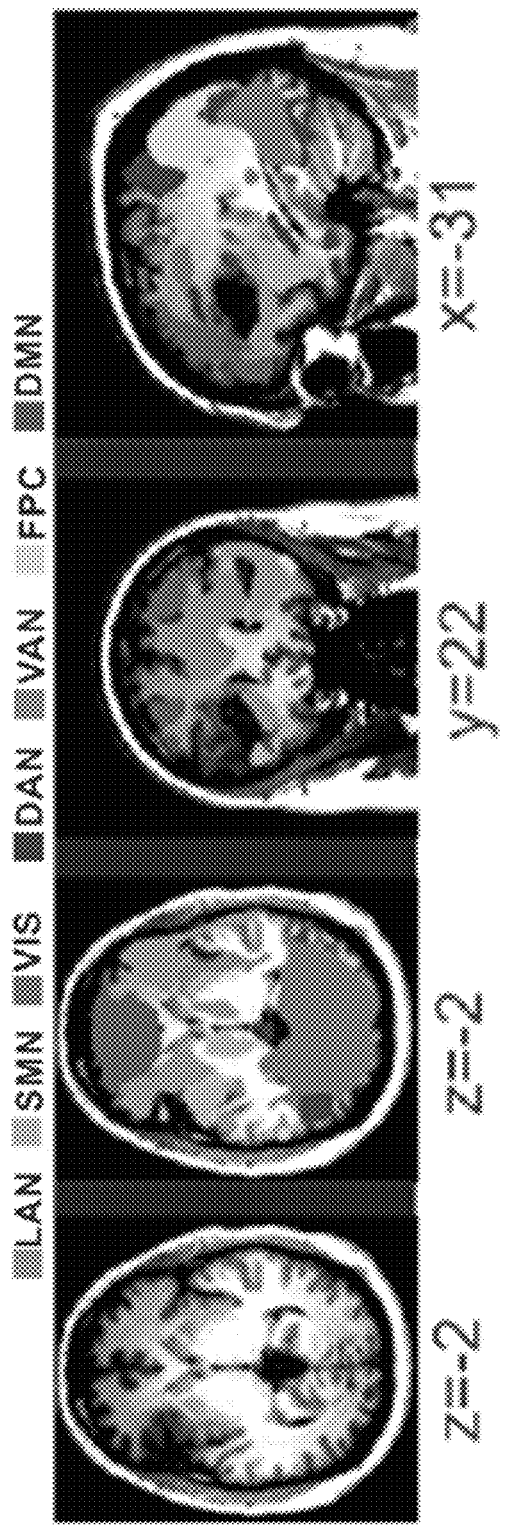
FIG. 25E is a series of resting state network (RSN) maps of a fifth patient with brain tumor produced using a multi-level perceptron RSN mapping method according to one aspect of the disclosure.
Figure 26A:
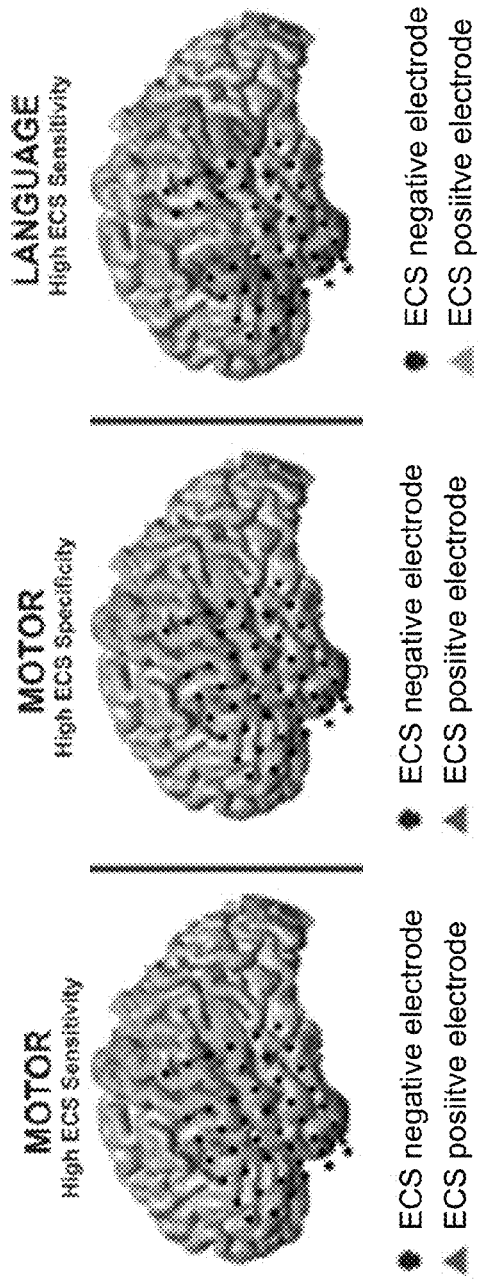
FIG. 26A contains a series of MLP-based RSN maps overlaid with a corresponding map of ECS electrode classifications for a first patient.
Figure 26B:
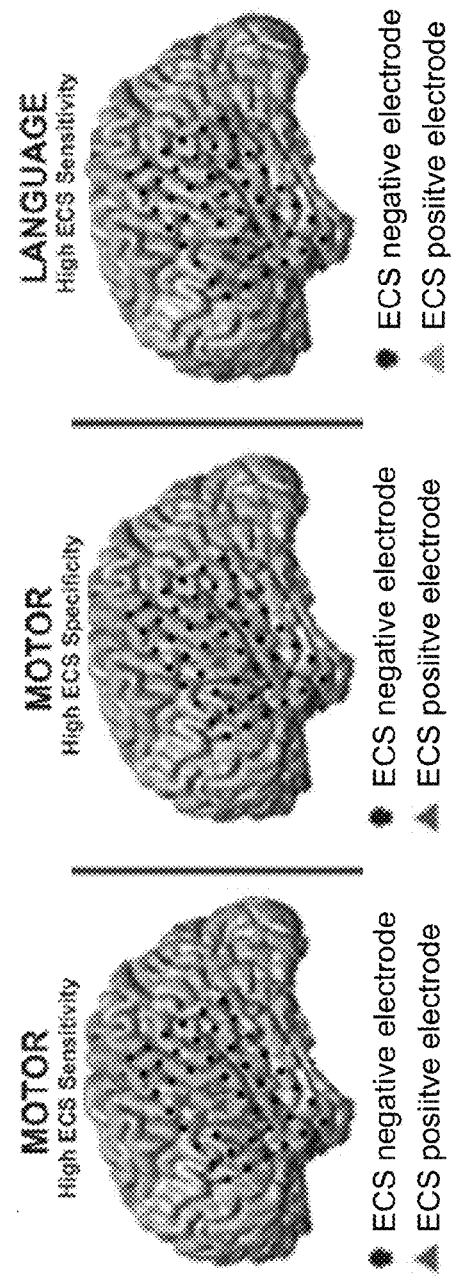
FIG. 26B contains a series of MLP-based RSN maps overlaid with a corresponding map of ECS electrode classifications for a second patient.
Figure 26C:
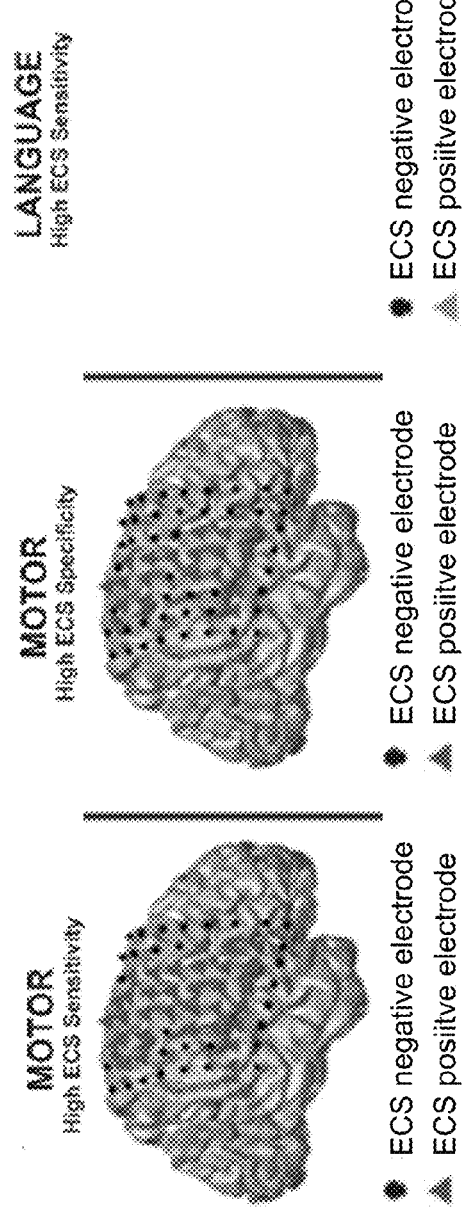
FIG. 26C contains a series of MLP-based RSN maps overlaid with a corresponding map of ECS electrode classifications for a third patient.
Figure 26D:
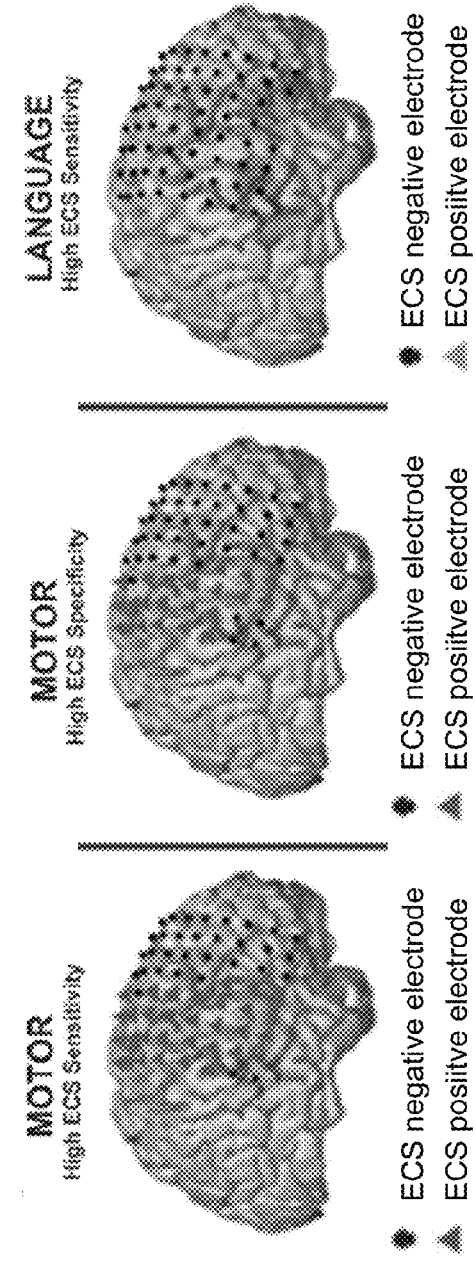
FIG. 26D contains a series of MLP-based RSN maps overlaid with a corresponding map of ECS electrode classifications for a fourth patient.
Figure 26E:
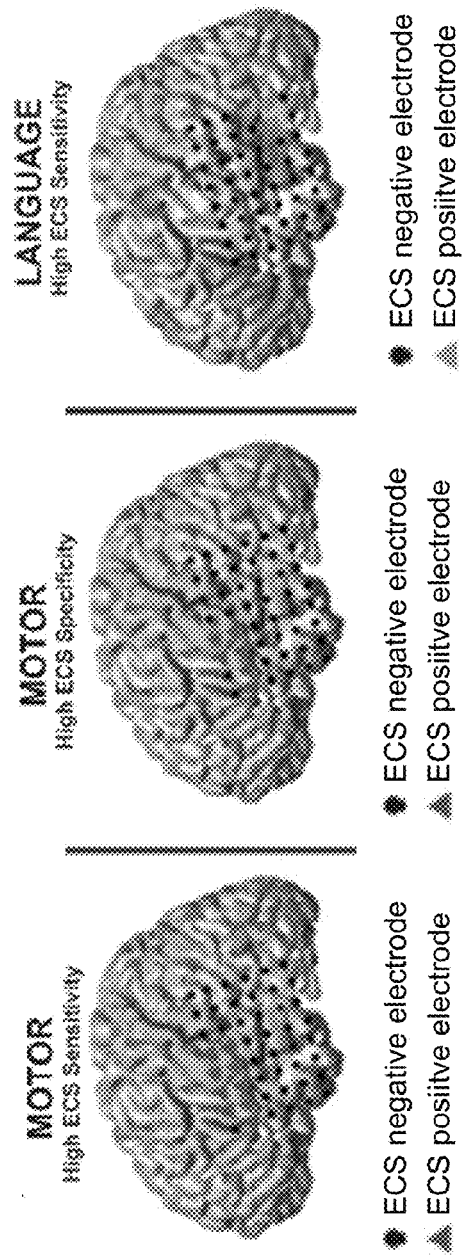
FIG. 26E contains a series of MLP-based RSN maps overlaid with a corresponding map of ECS electrode classifications for a fifth patient.
Figure 26F:
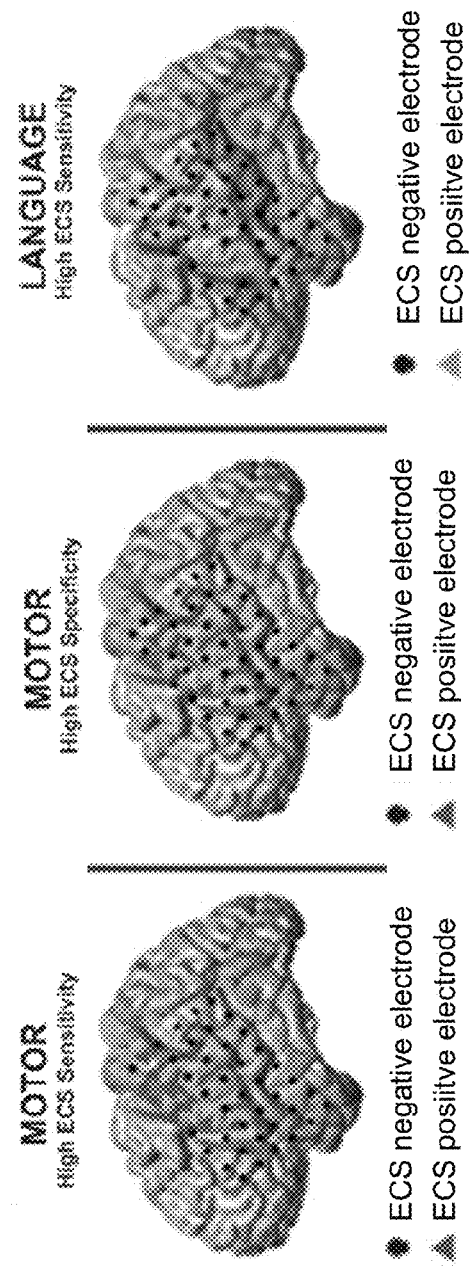
FIG. 26F contains a series of MLP-based RSN maps overlaid with a corresponding map of ECS electrode classifications for a sixth patient.

FIGS. 24A and 24B includes whole-brain maps (left and right, respectively) of seed-based correlations with a 15-mm spherical ROI at the left-sided rTMS target, including pre-treatment maps, post-treatment maps, and differential change with treatment, obtained by subtracting corresponding pre-treatment and post-treatment maps.

Whole-brain seed-to-voxel connectivity with the left-sided stimulation site showed anti-correlation with bilateral DMN nodes (ventromedial/dorsomedial prefrontal cortices, precuneus, and temporal poles), which was attenuated with treatment. The right-sided stimulation site did not show such a clear pattern of anti-correlation with DMN.

The results of these experiments demonstrated a method of identifying TBI-related depression and the effects of rTMS treatment on TBI-related depression based on correlations between individual voxels and defined function network regions of a functional map produced using the supervised classifier with multi-level perceptron method described herein.

Example 5: MLP-Based RSN Mapping of Patients with Brain Tumors

To compare the efficacy of MLP-based RSN mapping in the presence of focal anatomic distortions and rearrangements of RSN topography, the following experiments were conducted.

Seven patients with brain tumors were subjected to MLP-based RSN mapping. For each patient, T1-weighted and T2-weighted images were obtained and regions including the brain tumor were segmented manually from these images. The MLP-based RSN mapping was performed for each patient using methods similar to those described in Ex. 1 above, except that the multi-layer perceptron (MLP) was individually trained in each patient to exclude lesion voxels segmented T1-weighted and T2-weighted images.

FIGS. 25A, 25B, 25C, 25D, and 25E each contain a series of images of RSN maps obtained for each of five of the patients, respectively. The MLP-based RSN mapping method reliably assigned RSN membership in all voxels, including voxels not included in the training set. The results of this experiment demonstrated that the MLP-based RSN mapping method accommodated focal anatomic distortions and rearrangements of RSN topography, as is typical in patients with brain tumors.

Example 6: Comparison of MLP-Based RSN Mapping to Cortical Stimulation Mapping in Epilepsy Patients To assess the accuracy of functional cortical mapping obtained using MLP-based RSN mapping, the following experiments were conducted.

Six patients with intractable epilepsy were subjected to both functional mapping using an MLP-based RSN mapping method similar to the method described in Ex. 1 as well as existing cortical stimulation methods (ECS). Before surgical implantation of electrodes, all patients underwent anatomic and rs-fMRI imaging. Epilepsy patients underwent an initial craniotomy for subdural placement of an electrode array that was removed with a second craniotomy approximately one week later during resection of the epileptic foci. The implanted electrodes were precisely aligned to preoperative T1-weighted anatomic imaging obtained using standard clinical protocols. Subjects underwent intracranial electrocorticographic monitoring to localize the epileptogenic zone of seizure onset and to perform functional mapping with ECS. CT images were acquired prior to removal of the grid. Electrodes imaged on the postoperative CT images were displaced inward relative to the location of the subject's cortical surface imaged preoperatively. This displacement of the cortical electrodes was compensated for in subsequent comparisons by projecting electrode coordinates to the surface of the brain along a path normal to the surface of the grid.

The ECS electrodes in each patient were classified with respect to motor or language function according to two existing methods: a high ECS sensitivity scheme and to a high ECS specificity scheme. Using the high ECS sensitivity scheme, any ECS electrode that elicited a motor or language response when activated in isolation was classified as ECS positive, and any ECS electrode that failed to elicit a motor or language response when activated in isolation was classified as ECS negative. ECS electrodes were also activated pairwise and similarly assessed as part of the high ECS specificity scheme. Using the high ECS specificity scheme, any ECS electrode that elicited a motor or language response when activated in isolation was classified as ECS positive, so long as it was not also part of an electrode pair that was classified as ECS negative during pair-wise assessment. In addition, any ECS electrodes that failed to elicit a motor or language response when activated in isolation was classified as ECS negative.

FIGS. 26A, 26B, 26C, 26D, 26E, 26F contain a series of MLP-based RSN maps overlaid with a corresponding map of ECS electrode classifications for each of the six patients, respectively. The left-most image in each of these figures contains a map of the MLP-based somato-motor network (SMN), shown in turquoise, with ECS electrode position overlaid and classified according to the high ECS sensitivity scheme as ECS positive (red triangles) and ECS negative (black circles). The center image in each of these figures contains a MLP-based SMN map, shown in turquoise, with ECS electrode positions overlaid and classified according to the high ECS specificity scheme as ECS positive (red triangles) and ECS negative (black circles). The right-most image in each of these figures contains a map of the MLP-based language network (LAN) and frontoparietal control network (FPC), respectively shown in orange and yellow, along with ECS electrode position overlaid and classified according to the high ECS sensitivity scheme as ECS positive (green triangles) and ECS negative (black circles).

Despite anatomical distortion, there was good agreement between ECS and MLP-based functional localization. The positive motor ECS electrodes were centered in the precentral gyrus. The positive language ECS electrodes were centered in the pars opercularis area of the inferior frontal gyrus (IFG) (approximately Brodmann area (BA) 44) posterior to the MLP language positive regions, which were in the pars triangularis of the IFG (approximately BA 45).

Figure 27A:
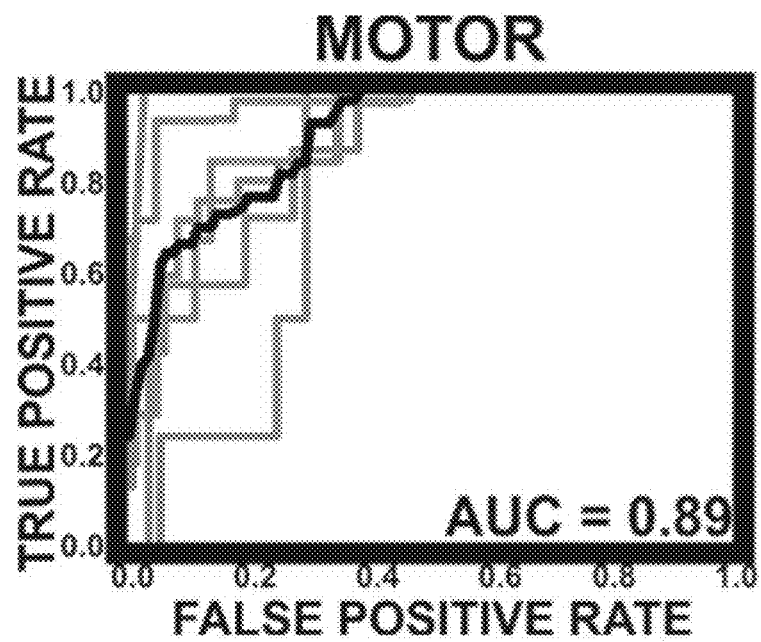
FIG. 27A is a receiver-operating characteristic (ROC) curve for classification of motor network-related ECS electrodes using MLP-based RSN mapping methods.
Figure 27B:
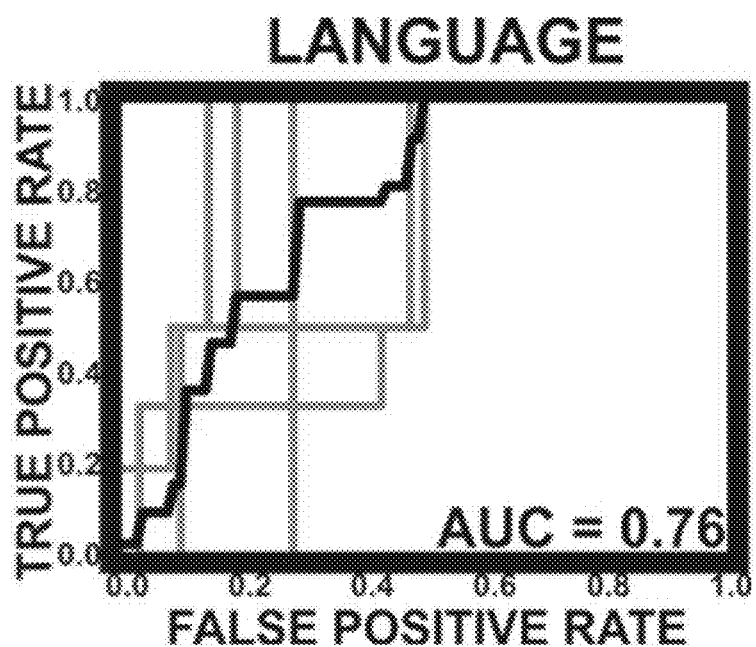
FIG. 27B is a receiver-operating characteristic (ROC) curve for classification of language network-related ECS electrodes using MLP-based RSN mapping methods.

Receiver-operating characteristic (ROC) curves were determined based on measurements from each individual patient. FIG. 27A is graph showing the ROC curves for the motor cortical network for the six patients, and FIG. 27B is a similar graph showing the ROC curves for the language cortical network. The ROC analysis yielded an average area under the curve (AUC) of 0.89 for the motor network and an average AUC of 0.76 for the language network.

The results of these experiments demonstrated agreement between the topography of resting state networks and cortical stimulation mapping, even in the presence of distortion of the brain due to the insertion of ECS electrode grids.

Example 7: Comparison of MLP-Based RSN Mapping with Task-Based Network Mapping for Patients with Brain Tumors To assess the accuracy of functional mapping using MLP-Based RSN mapping as compared conventional task-based fMRI that includes activation of the motor and language systems, the following experiments were conducted.

Twenty patients with large brain neoplasms impinging on either motor or language areas were subjected to both task-fMRI and resting state fMRI in the same session prior to tumor resection. Functional mapping was performed for the task-fMRI data using standard clinical methods and the rs-fMRI data analysis was performed using an MLP-based RSN mapping method similar to the method described in Ex. 1. The functional mapping results obtained by both techniques were displayed and mutually co-registered in Talairach atlas space as un-thresholded continuous values superimposed on T1-weighted structural images also obtained to assess the location of the tumor. All functional mapping images were scored by 3 experienced clinicians on a 4-point scale representing localizing utility: 4: Excellent depiction of the functional anatomy in relation to the lesion; 3: Adequate identification of the functional components of interest; 2: Borderline results, with limited clinical utility; 1: No clinically useful results.

Figures 28A, 28B:
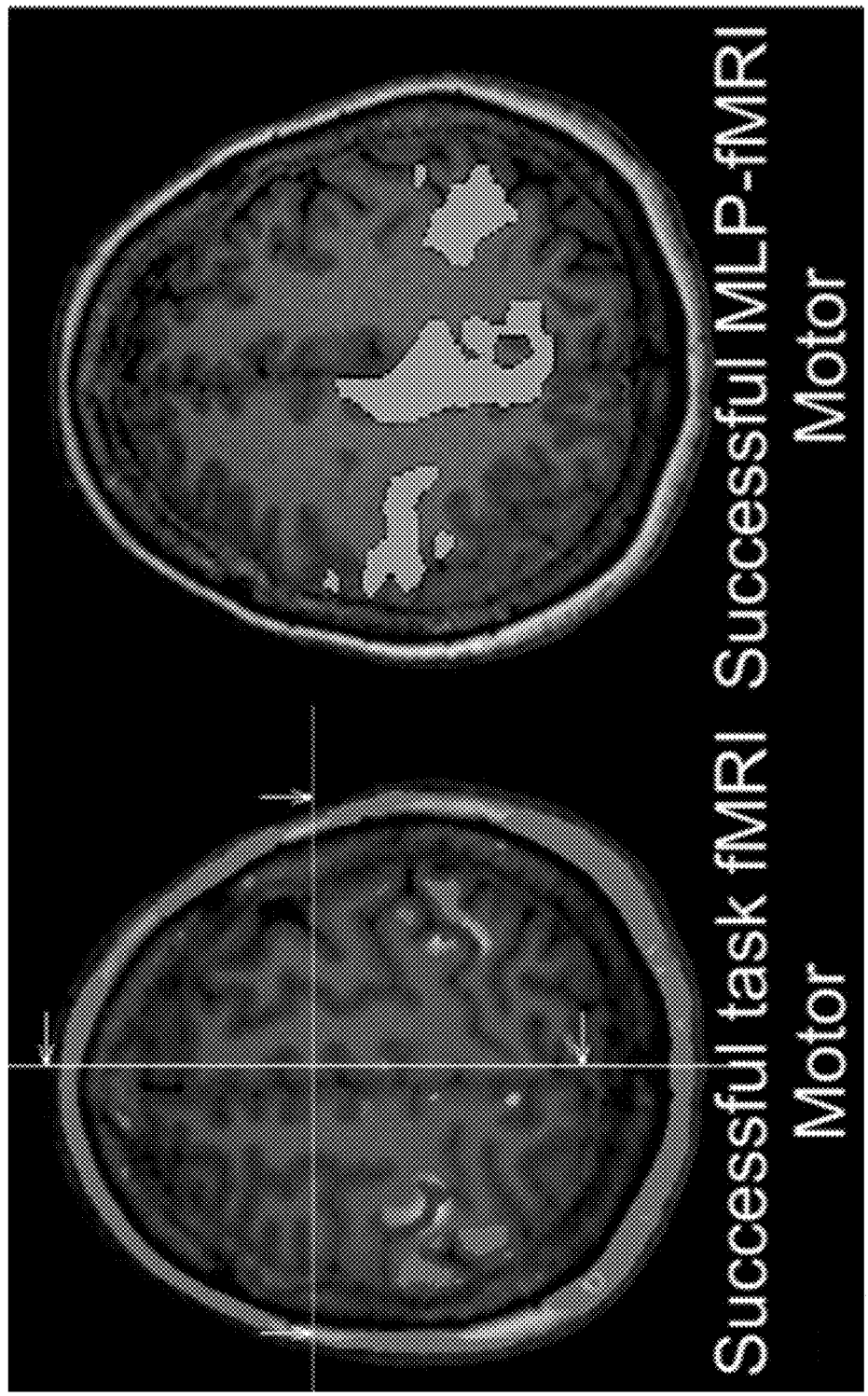
FIG. 28A is a map of a motor-related functional network obtained using task-based fMRI methods.
FIG. 28B is a map of a motor-related functional network obtained using an MLP-based RSN mapping methods according to an aspect of the disclosure.
Figures 28C, 28D:
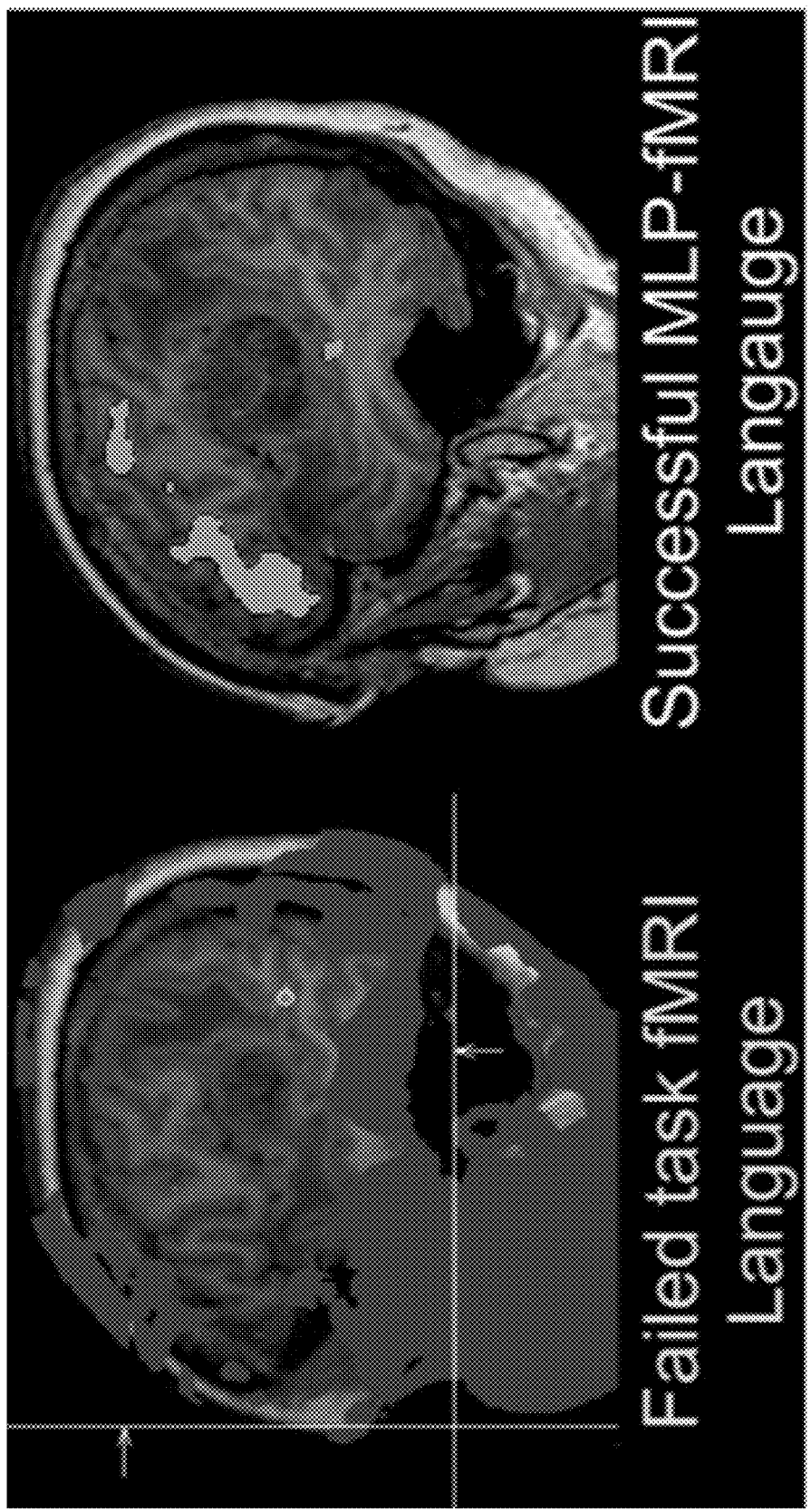
FIG. 28C is a map of a language-related functional network obtained using task-based fMRI methods.
FIG. 28D is a map of a language-related functional network obtained using an MLP-based RSN mapping methods according to an aspect of the disclosure.

FIG. 28A is an image showing an example of a task-based fMRI-derived map of the motor-related network that was scored as a 4 according to the process described above. FIG. 28B is an image showing an example of an MLP-based RSN map of the motor-related network that was scored as a 4 according to the process described above. In the same patient, FIG. 28C is an image showing an example of a task-based fMRI-derived map of the language-related network that was scored as a 2, and FIG. 28D is an image showing an example of MLP-based RSN map of the language-related network that was scored as a 4.

Figures 29, 30:
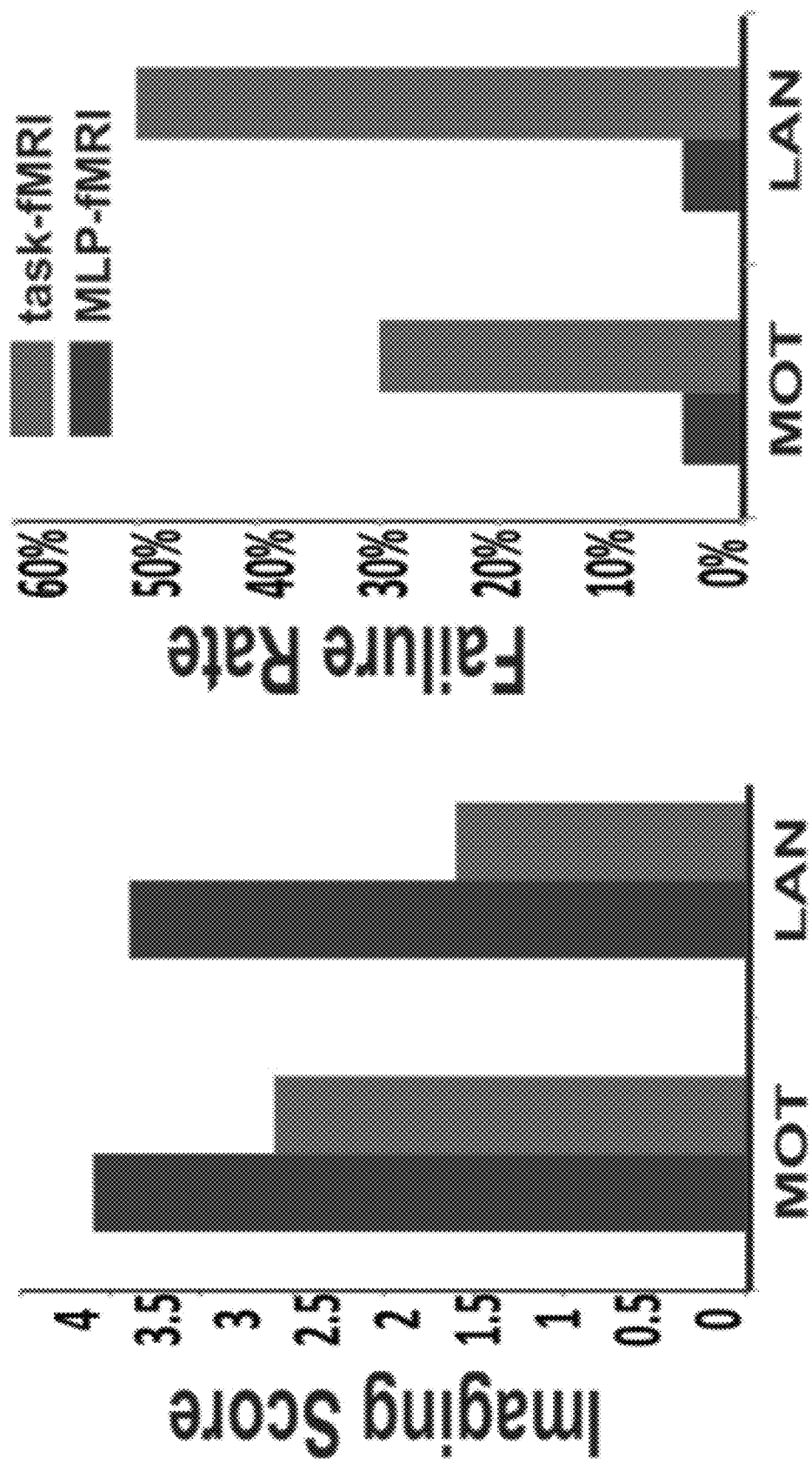
FIG. 29 is a bar graph summarizing an imaging score for motor-related and language-related functional networks mapped using task-based fMRI methods and MLP-based RSN mapping methods.
FIG. 30 is a bar graph summarizing a failure rate (percentage of total maps scored as having no clinically useful results) for motor-related and language-related functional networks mapped using task-based fMRI methods and MLP-based RSN mapping methods.

FIG. 29 is a bar graph summarizing the cumulative scores of all 20 subjects for task-based fMRI-derived mapping and MLP-based RSN mapping of the motor and language networks. Cumulatively over the 20 subjects, the motor system MLP-based score was 3.6 as compared to 2.6 for task-based fMRI score. For the language system, the contrast was more striking, with 3.4 for MLP-based score MLP and 1.6 for the task-based fMRI.

FIG. 30 is a bar graph summarizing the cumulative failure rates of all 20 subjects for task-based fMRI-derived mapping and MLP-based RSN mapping of the motor and language networks. The cumulative failure rate, as expressed in FIG. 30, refers to the percent of non-diagnostic scans (score of 1) for each category. The failure rate for the MLP-based RSN maps was 5% in both the motor and language systems. For the task-based fMRI maps, the failure rate was about 40% overall.

The results of this experiment demonstrated that MLP-based RSN mapping enhanced brain function localization in comparison to task-based fMRI mapping, especially with respect to language function localization. In addition, the results of this experiment further demonstrated that the MLP-based RSN mapping method accommodated focal anatomic distortions and rearrangements of RSN topography, as is typical in patients with brain tumors.

Example 8: Comparison of MLP-Based RSN Mapping with Task-Based Network Mapping for Presurgical Planning To evaluate the systematic integration of rs-fMRI and MLP-based functional mapping into the routine pre-surgical work-up systems and methods, the following experiments were conducted.

191 consecutive patients underwent a 3T rs-fMRI, 83 of whom also underwent both motor and language task-based fMRI. Data were processed using an automated, multi-layer perceptron algorithm similar to the method described in Ex. 1 and integrated into stereotactic navigation using a streamlined IT imaging pipeline as described below. The patient demographics and underlying disease that were evaluated with rs-fMRI are summarized in Table 7 below.

TABLE 7

| Patient Demographics | |
| --- | --- |
| Total patients | N = 191 |
| Male | N = 118 (62%) |
| Female | N = 73 (38%) |
| Age | 46 y/o (3-84 y/o) |
| Adult | N = 173 (91%) |
| Children | N = 18 (9%) |
| Tumor | Low grade glioma N = 41 (21%) |
| | High grade glioma N = 80 (42%) |
| | Other tumors (DNET, Meningioma, Pilocytic Astrocytoma, Ganglioglioma) |
| | N = 32 (17%) |
| Vascular Malformations | N = 10 (5%) |
| Epilepsy | N = 6 (3%) |
| Non-neoplastic (Encephalitis, OCD Neurocysticercosis, Amyloid angiopathy, CJD) | N = 12 (6%) |
| Negative pathology | N = 6 (3%) |
| Pathology N/A (4/191) | N = 4 (2%) |

The topography of resting state networks (RSNs) in individual patients was evaluated using a multilayer perceptron (MLP) trained to estimate RSN membership of brain loci from resting state fMRI (rs-fMRI) correlation maps. The MLP was previously trained to associate correlation maps generated from canonical regions of interest (ROIs) with a priori class labels corresponding to seven predefined resting state networks. ROIs representing distinct RSNs were isolated by meta-analysis of task-fMRI responses. The seven RSN were as follows: default mode network (DMN), sensorimotor network (SMN), visual network (VIS), language network (LAN), dorsal and ventral attention network (DAN, VAN), and the fronto-parietal control network (FPC). The definition of RSNs with the MLP made use of data obtained from young adults screened to exclude neurological impairment and psychotropic medications. Training, optimization, and validation used previously acquired datasets.

The MLP consisted of an input, hidden, and output node layer, fully connected in a feed-forward manner, as illustrated schematically in FIG. 7. Each training input was a correlation map generated from one of 169 canonical seed ROIs across N=21 normal control subjects. Each node in a particular layer was connected to each node in the subsequent layer, and the strength, or weight, of these connections characterized the MLP's classification of the input data. As illustrated in FIG. 5, the input image was propagated through the layers of the MLP; and the output was then compared to a seven dimensional binary output label vector. The difference of the output and the training label generated an error signal; and the back propagation algorithm was used to minimize the squared error across all RSNs for all correlation map training inputs. This training process allowed the MLP to learn a mapping between the rs-fMRI correlation maps (from seeds across the brain) and RSN identity. After training, the MLP was applied comprehensively to the entire brain by generating a correlation map for each voxel (treating each voxel as a seed) and then computing RSN estimates by propagating this map through the MLP. Thus, the MLP was used to generate a seven-dimensional RSN estimate for every voxel within the rs-fMRI data set. For each RSN, a whole-brain image was produced with an estimate of the likelihood of membership at each voxel within the whole-brain image.

All patients were scanned using a 3-T TRIO scanner (Siemens, Erlangen, Germany). rs-fMRI data were acquired using a T2*EPI sequence (1×1×1-mm voxels; 128 volumes/run; TE=27 ms; TR=2 s; field of view=256 mm; flip angle=90°), while the patients were instructed to remain still and fixate on a visual cross-hair without falling asleep (total time 12 minutes). Tumor protocol anatomic imaging included T1-weighted magnetization-prepared rapid acquisition gradient echo (MP-PAGE), T2-weighted fast spin echo, susceptibility-weighted imaging (SWI), diffusion-weighted imaging (DWI) and pre and post gadolinium T1-weighted fast spin echo in multiple projections. All anatomic and functional magnetic resonance data were acquired in approximately 60 minutes for each patient.

Patients were identified who had concurrent task-based fMRI (tb-MRI) and resting state fMRI. All studies were evaluated as successful or failed with regard to demonstrating clinically relevant topographies. Specifically, the subset of eighty-three patients that received both resting state fMRI and task-based fMRI was compared to assess the failure rate in which no functional localization was accomplished using resting state fMRI and/or task-based fMRI.

A total of 191 consecutive patients (173 adults and 18 children) underwent a total of 232 rs-fMRI sessions, as summarized in Table 7 above. One hundred fifty-five patients had a single rs-fMRI session, 31 patients had 2 rs-fMRI sessions and 5 patients had 3 rs-fMRI sessions. One hundred eighty-five studies were performed in the setting of intracranial neoplasm, either primary or metastatic, 14 studies were performed in patients with epilepsy and 33 studies were performed in the setting of other neurologic disorders (including vascular malformations, inflammatory or infectious disorders, as well as neurological disorders). For the neurosurgical patients, 76% were used in the context of a craniotomy, 15% with laser interstitial therapy, and 9% with biopsy.

Of the 191 unique patients undergoing rs-fMRI, 83 patient also underwent both motor and language task-based fMRI. Table 8 summarizes the results of the comparison of failure rates of the two fMRI methods. Thirty-two task-based fMRI studies failed to achieve functional localization (38.5%, 32/83) while 28 rs-fMRI sessions failed to achieve functional localization (13%, 28/232). These differences between the failure rates of resting state and task-based fMRI were statistically significant (p<0.0001, Fischer's exact test) with rs-fMRI having a significantly reduced rate of imaging failure. Causes of failure for both study types included lack of cortical activation despite appropriate thresholding, motion or susceptibility artifact, lack of cooperation, lack of MPRAGE image acquisition for registration, registration errors and technical errors such as incorrect TE/TR parameters, as summarized in Table 8 below.

TABLE 8

Comparison of rs-fMRI and Task-Based fMRI

| Cause Of Failure | rs-fMRI (n = 232) | task-based fMRI (n = 83) |
|---|---|---|
| Patient Motion | 14 (6.0%) | 0 (0%) |
| Susceptibility artifact | 6 (2.6%) | 0 (0%) |
| Unable to follow commands | 0 (0%) | 10 (12%) |
| No activation | 2 (.9%) | 20 (24%) |
| Technical failure NOS/did not pass QA | 3 (1.2%) | 2 (2.5%) |
| Anatomic misregistration to atlas | 3 (1.2%) | 0 (0%) |
| Total | 28 (13%) | 32 (38.5%) |

Most resting state failures were due to motion that occurred during the resting state acquisition when the patients fell asleep, had involuntary movements, or forgot instructions to hold still. This typically did not occur with the successful task-fMRI because the patient can remain still and awake while concentrating on a task to perform. The anatomic distortion was due to extreme cases of mass effect or large territories of prior resection. The resting state processing algorithm generally handled moderately large tumors or regions of resected brain quite well. The signal loss due to susceptibility occurred in one pediatric patient with braces and in a few patients who recently had resections or had recent hemorrhage causing signal loss next to large collections of blood or postoperative gas.

A number of individual cases further illustrate the utility of rs-fMRI imaging with perceptron-based functional mapping methods, as described below.

Comparable Localization Between Task and Resting-State fMRI.

Figure 33:
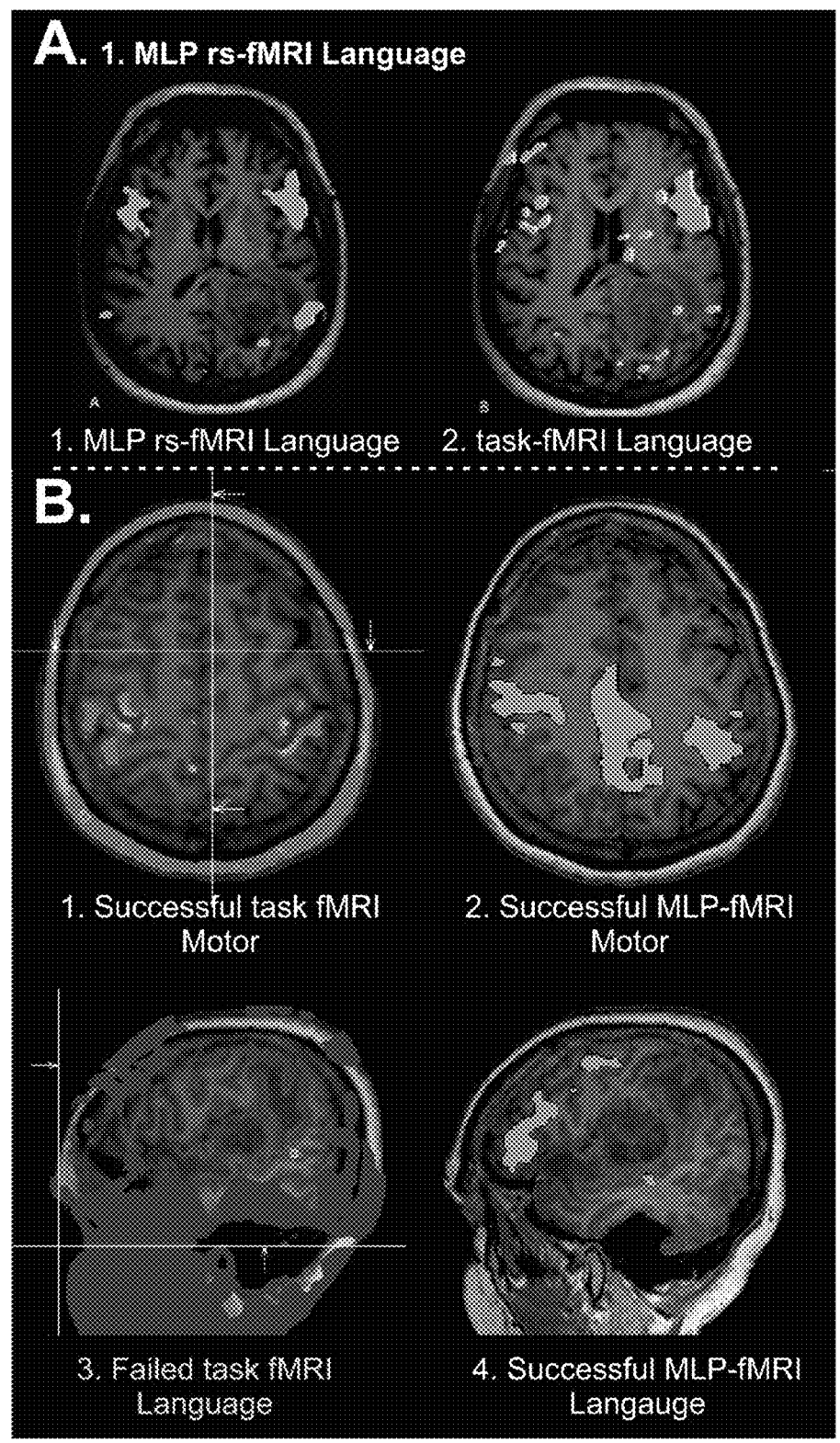
FIG. 33 shows a series of comparisons of perceptron-based RSN mapping and task-based MRI functional mapping results.

Patient was a sixty-two year-old with left parietal biopsy-proven glioblastoma multiforme. Resting state fMRI is shown in FIG. 33A.1 and task-based fMRI is shown in FIG. 33A.2. Broca's area activation bilaterally and Wernicke area activation on the left were similar for both techniques.

Successful rs-fMRI Mapping in the Setting of Failed Task-Based fMRI.

Patient was a fifty-year-old male with new onset of headache. Preoperative functional imaging demonstrated a large mass in the posterior inferior frontal lobe. FIG. 33B.1 shows motor system results with MLP-rs-fMRI and FIG. 33B.2 shows motor system results for task-based fMRI. Both methods show reasonable functional localization around the central sulcus. In the same patient, FIG. 33B.3 shows language system results for MLP-rs-fMRI and FIG. 33B.4 shows language system results for task-based fMRI. While there was no evidence of cortical activation within the frontal lobe with task-based fMRI for language (FIG. 33B.3), there was a strong functionally localized region with MLP-defined resting-state MRI (FIG. 4B.4). Taken together, these findings demonstrated that MLP-resting state fMRI has the capability of identifying functional cortex in tenuous regions where task-based fMRI fails.

Mapping Speech Sites in an Aphasic Patient.

Figure 34:
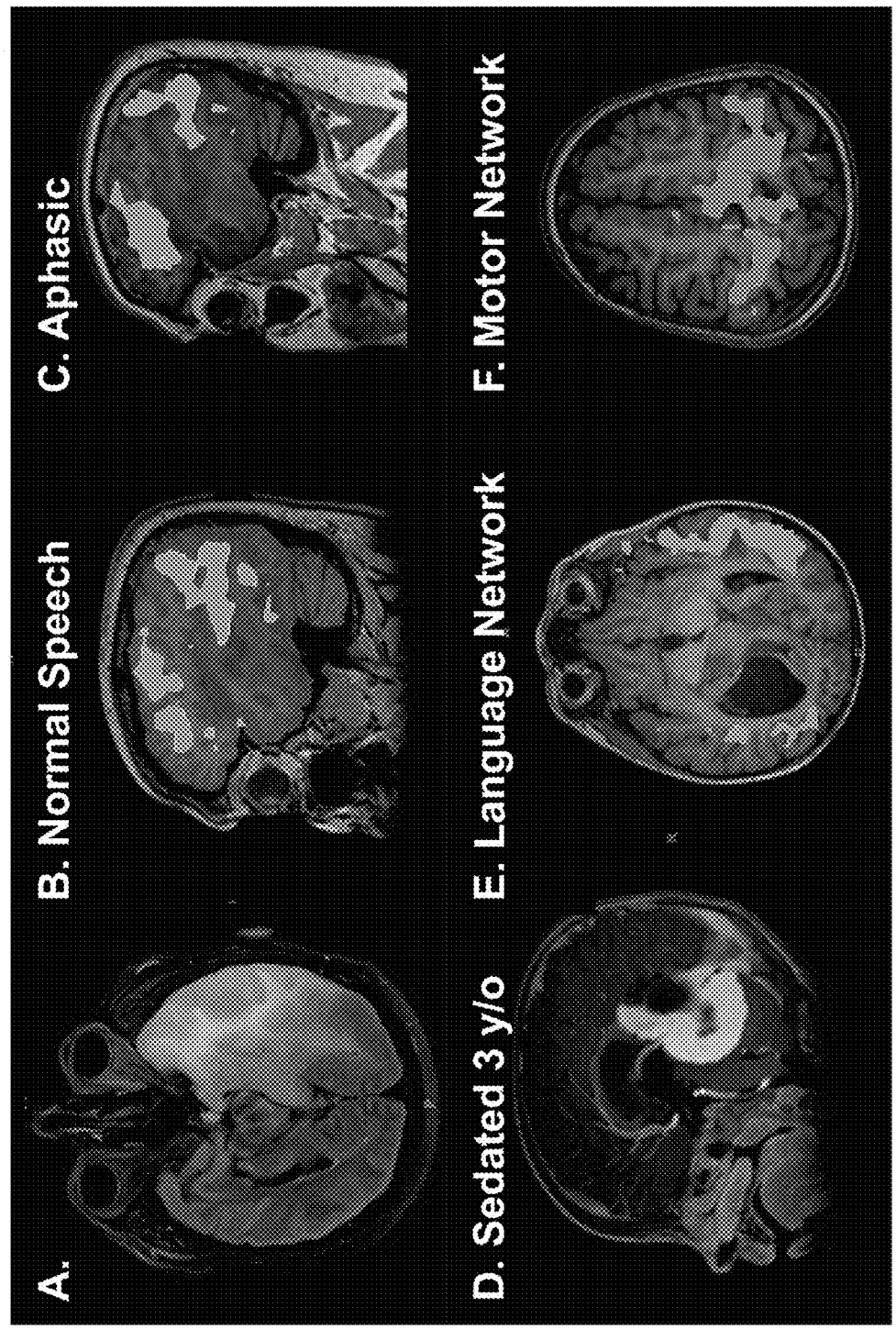
FIG. 34 shows a series of comparisons of perceptron-based RSN maps for various patients.

Patient was a forty-year-old male who presented with headaches and speech difficulty. Further evaluation with MRI demonstrated an expansile left temporal tumor (FIG. 34A). The patient was given steroids and his speech returned to normal. During this time a resting state MRI was obtained and speech networks were identified (FIG. 34B). Prior to his scheduled surgery he had a prolonged seizure and was post-ictally globally aphasic for several days. During this time a repeat resting state MRI was obtained and speech networks were again identified despite his inability to speak (FIG. 34C). These findings were significant because they provided an extreme example of being able to map function despite compromised cognitive function (i.e. mapping speech in the setting of an aphasia). Notably, the resting state network topographies were similar between imaging when speech was intact and when it was compromised.

Mapping Eloquent Cortex in a Sedated Pediatric Patient.

Patient was a three old boy with a prior history of pineal region fibroblastic spindle cell tumor that was previously resected who presented with behavioral changes and vomiting. For MR imaging he was sedated with propofol and sevoflurane. Imaging demonstrated a large tumor in the brain stem (FIG. 34D), and motor network (FIG. 34E) and speech network (FIG. 34F) were clearly defined. Consistent with prior studies in animals and humans, resting state networks were present despite alteration of consciousness with anesthetics. It was noted that the patient was quite young and any form of task-based fMRI would not have been possible.

One hundred eighty-five studies were performed for intracranial neoplasm, 14 for refractory epilepsy and 33 for vascular malformations or other neurological disorders. Failure rate of rs-fMRI of 13% was significantly better than that for task-based fMRI (38.5%, p<0.001).

Example 9: Positioning of Implant Devices Using MLP-Based RSN Mapping

To demonstrate the use of rs-fMRI and MLP-based functional mapping for choosing an appropriate location for an implanted device such as a cortical stimulator, the following experiments may be conducted.

MLP-based functional mapping as described herein will be used to position a chronically implanted ECoG-based BCI system or focal cortical stimulator that would consist of either a subdural or epidural array that includes amplification/digitization/wireless electronics and is powered by a battery either at the site or at a remote site (e.g., in the chest). The device will be permanently implanted through a small (e.g., 19-mm) burr hole in the skull. It is envisioned that ECoG-based systems or cortical stimulators would be implemented in a series of four steps that proceed from functional localization to coregistration, to implantation, and to integration.

Figure 35:
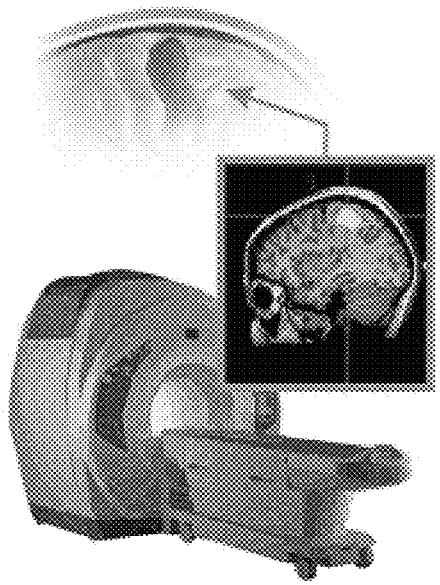
FIG. 35 is a schematic diagram showing a method of positioning an implant device using perceptron-based RSN maps.
Figure 35:
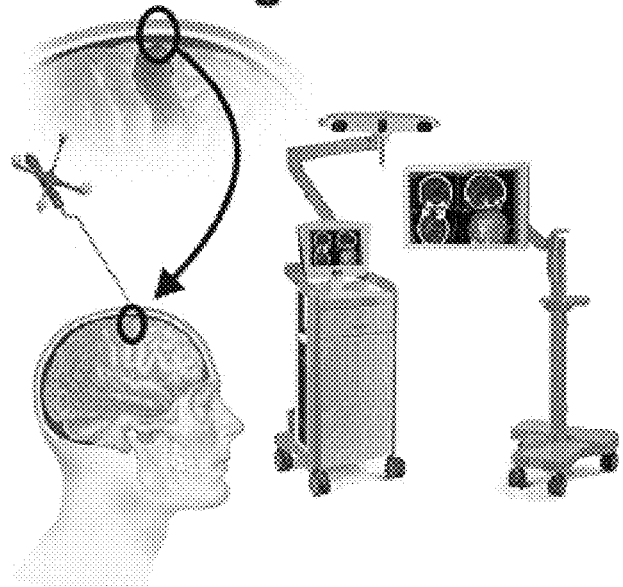
Figure 35:
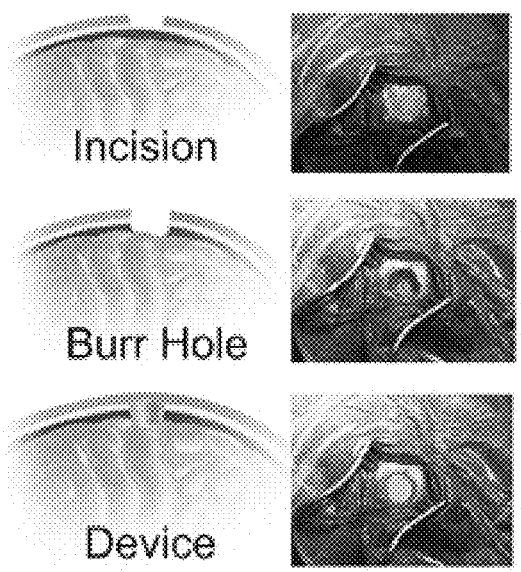
Figure 35:
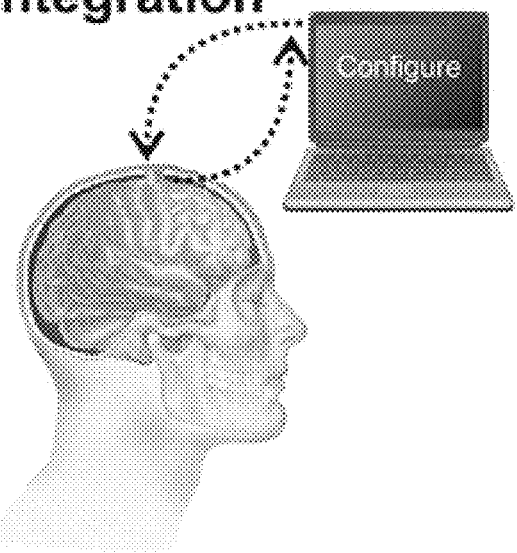

FIG. 35 is a schematic illustration showing a clinical implementation of cortical stimulation and recording technology. As illustrated in FIG. 35, multiple stages will likely be required for the evaluation and application of an ECoG BCI in a human subject. The first step will involve a preoperative localization of the functional region in question using the perceptron-based cortical mapping methods described herein. The second step will include an anatomic coregistration of this functional region with the actual physical anatomy of the patient. The third step will involve the implantation of the device. This envisioned technology will be small and minimally invasive requiring only a small burr hole in the skull. FIG. 35 includes schematic diagrams on the left and actual surgical photographs on the right. Finally, after implantation, the device will be configured to integrate with the user's specific needs.

The purpose of the first step, functional localization, will be the identification of those cortical areas that represent the best substrate for either BCI control and/or cortical stimulation and thus will identify the target location for subsequent device implantation. The procedure for this localization will be realized using resting state functional magnetic resonance imaging (fMRI) and subsequent processing using the perceptron.

The purpose of the second step, coregistration, will be to relate the target location t identified by the first step [which will be defined in some coordinate system relevant to the imaging system used (e.g., Talairach coordinates)] to the physical position on the person's brain. This step will be achieved using conventional stereotactic navigation systems.

The purpose of the third step, implantation, will be to place the ECoG sensing/transmission/stimulating device over the identified location and to secure it to the skull. This procedure will also entail placement of a battery at a remote site and installation of related cabling.

The purpose of the fourth step, integration, will be to configure the BCI system such that it properly identifies and detects relevant brain signals and relates them to the output function desired by the user.

Example 10: Diagnosis of Depression Using MLP-Based RSN Connectivity Analysis

To demonstrate the use of rs-fMRI and MLP-based functional mapping and associated connectivity analysis to diagnose a neurological disorder in a patient, the following experiments were conducted.

Antidepressant efficacy of rTMS has been associated with anticorrelation between treatment targets and subgenual anterior cingulate cortex (sgACC). Treatment also modulates sgACC-mediated interactions between executive networks and default mode network (DMN) as defined by group-mean maps. While inter-individual variability is better predicted by novel individualized resting-state network mapping (RSNM) techniques, this has not been evaluated for rTMS targeting.

Individualized DAN/DMN maps were constructed using a machine learning-based RSNM algorithm based on iterative correlation mapping of individual resting-state fMRI regions against a training dataset. Subjects included 10 healthy controls (HCs) and 10 subjects with traumatic brain injury-associated depression (TBI-D), which may exhibit exaggerated inter-individual network variability. RSNM-based targets were identified as left/right superficial dorsolateral prefrontal clusters with maximal DAN-DMN difference. Comparators included standard structural targets and anti-sgACC clusters identified via previously-described targeting methods. Targets were compared in terms of spatial distance and Fisher-transformed correlation with group-based DAN and DMN maps.

Five TBI-D subjects underwent 20 sessions of RSNM-targeted high-frequency left-sided and low-frequency right-sided rTMS as part of an ongoing randomized blinded clinical trial. Baseline FC (bFC) was compared with change in FC (ΔFC) between/within seven individualized cortical network parcels in both hemispheres via linear regression.

RSNM targets showed stronger DAN correlation and DMN anti-correlation than anti-sgACC or structural targets (0.001<p<0.04, Table 9). Targets were spatially distinct from one another with distances comparable to expected stimulation radius.

TABLE 9

Evaluation of TBI-D Patients

| Target | TBI-D | | | Healthy control | | |
|---|---|---|---|---|---|---|
| | RSNM | Anti-sgACC | Structural | RSNM | Anti-sgACC | Structural |
| DAN correlation | 0.31 | 0.17 (p = 0.04) | 0.16 (p = 0.001) | 0.34 | 0.20 (p = 0.04) | 0.26 (p = 0.02) |
| DMN correlation | −0.42 | −0.27 (p = 0.005) | −0.34 (p = 0.02) | −0.46 | −0.25 (p = 0.002) | −0.33 (p = 0.00006) |

TABLE 9-continued

Evaluation of TBI-D Patients

| Target | TBI-D | | | Healthy control | | |
|---|---|---|---|---|---|---|
| | RSNM | Anti-sgACC | Structural | RSNM | Anti-sgACC | Structural |
| Distance from RSNM target (mm, 95% CI) | | 13.5 (10.9-16.2) | 9.4 (7.5-11.4) | | 16.9 (15.6-19.2) | 6.6 (4.9-8.2) | bFC was directly related to ΔFC for left/right DAN-DMN correlations (mean Fisher z=0.59, 95% CI 0.31-0.87) despite a strong inverse relationship for other network-network correlations (mean z=−0.90, 95% CI −1.12 to −0.68). Unpaired t-test revealed Bonferroni-corrected p=0.017 for the difference between left/right DAN-DMN correlations and all other correlations. DAN correlations changed in the opposite direction to the pre-treatment mean for all subjects, while all other network correlations regressed towards the mean.

The bFC vs. ΔFC analyses were repeated using established group-based resting-state network maps. The resulting correlations were weaker and were not statistically significant after multiple corrections comparison. This result suggested that perceptron-generated seeds are more effective for monitoring of treatment progress.

Compared with previously-described methods, individual-level RSNM identified spatially distinct rTMS targets with stronger DAN correlations and DMN anti-correlations. Functional connectivity changed in a manner that may be predicted by baseline FC in the targeted network and in other networks.

Although specific features of various embodiments of the invention may be shown in some drawings and not in others, this is for convenience only. In accordance with the principles of the invention, any feature of a drawing may be referenced and/or claimed in combination with any feature of any other drawing.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

In operation, a computer executes computer-executable instructions embodied in one or more computer-executable components stored on one or more computer-readable media to implement aspects of the invention described and/or illustrated herein.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method for determining a target location for a therapeutic stimulation intervention in a subject with a depression disorder, the computer-implemented method implemented by a computing device including at least one processor in communication with a memory device, the computer-implemented method comprising:
   receiving brain resting state fMRI (rs-fMRI) data for the subject acquired over a course of time with the subject in a state of rest;
   using an established set of predefined canonical resting state networks (RSNs) comprising at least one of a dorsal attention network (DAN) and a default mode network (DMN), analyzing the resting-state fMRI data for the subject to determine index values for a plurality of volume elements (voxels) of the subject's brain, each of the determined index values representing a likelihood of a particular voxel being a member of a particular predefined canonical RSN, there being a separate determined index value for a particular voxel for each predefined canonical RSN;

applying a predetermined criterion to the determined index values for at least one of the DAN and the DMN to identify voxels having a canonical RSN membership likelihood consistent with a desired target location for the therapeutic stimulation intervention; and selecting, from the voxels identified as meeting the predetermined criterion, a set of contiguous voxels to serve as the target location for the therapeutic stimulation intervention in the subject; and generating an output comprising information indicating the target location configured for use in the therapeutic stimulation intervention on the subject with the depression disorder.

2. The method of claim 1, further comprising registering the target location to a structural map of the brain of the subject.

3. The method of claim 1, further comprising providing the target location to a treatment system configured to perform the therapeutic stimulation intervention.

4. The method of claim 3, further comprising operating the treatment system to provide the therapeutic intervention to the target location.

5. The method of claim 1, wherein analyzing the resting-state fMRI data for the subject to determine index values uses a supervised classifier method trained to determine index values for voxels representing likelihood of membership in each predefined canonical RSN.

6. The method of claim 5, wherein the supervised classifier method includes use of a multilayer perceptron-based machine learning classifier.

7. The method of claim 1, wherein the predetermined criterion applied to the index values comprises applying, for each voxel, a mathematical combination for each voxel applied to the determined index values of at least two predefined canonical RSNs, the mathematical combination selected from the group comprising a sum, a difference, a product, a ratio, or any combination thereof, or a transformation of the index values of the at least two predefined canonical RSN, the mathematical combination applied to the predetermined index values of the at least two predefined canonical RSNs, or any combination thereof, the transformation selected from the group comprising of a trigonometric transformation, a logarithmic transformation, a normalization, or any combination thereof.

8. The method of claim 7, wherein the at least two predefined canonical RSNs comprises the dorsal attention network (DAN) and the default mode network (DMN).

9. The method of claim 8, wherein the predefined criterion is selected to identify voxels with maximum anticorrelation in resting state brain activity between the DAN and the DMN.

10. The method of claim 9, wherein the mathematical combination of the predetermined criterion is a difference, for each voxel, in the index value for the DAN and the index value for the DMN.

11. The method of claim 10, wherein the predetermined criterion identifies voxels having a difference in the index value for the DAN and the index value for the DMN that representing locations with the maximum anticorrelation in resting state brain activity between the DAN and the DMN.

12. The method of claim 1, wherein the predetermined criterion applied to the index values comprises applying, for each voxel, a comparison operation selected from the group comprising:

whether the index value is equal to a statistic selected from the group consisting of a maximum index value and a minimum index value;

whether the index value is greater than a minimum threshold value;

whether the index value is less than a maximum threshold value; or whether the index value is between a first threshold value and a second threshold value.

13. The method of claim 12, further comprising determining a path to the target location for the therapeutic intervention, the path comprising a group of adjoining voxels extending from a cortical surface of the brain to the target location, wherein determining the path to the target location further comprises:

identifying a group of candidate voxels selected to minimize injury to functional brain tissue based upon the determined index values representing likelihood of membership in at least one RSN map being below a functional threshold to minimize injury to functional brain tissue; and selecting the group of adjoining voxels forming the path from the group of candidate voxels, wherein the group of adjoining voxels differs from the set of contiguous voxels, and the functional threshold is a separate threshold from the minimum threshold value, the maximum threshold value, the first threshold value, and the second threshold value.

14. The method of claim 1, wherein the therapeutic stimulation intervention provides stimulation energy from a location external of the surface of the subject's brain.

15. The method of claim 14, wherein the therapeutic stimulation intervention is transcranial magnetic stimulation (TMS) therapy.

16. The method of claim 14, wherein selecting the set of contiguous voxels to serve as the target location comprises selecting only voxels within a defined distance from the dural surface.

17. The method of claim 16, wherein the defined distance is 6 mm.

18. The method of claim 14, wherein selecting the set of contiguous voxels to serve as the target location comprises selecting only voxels within a predefined distance from previously-reported coordinates for Brodmann areas 9 and 46.

19. The method of claim 18, wherein the predefined distance is 20 mm.

20. The method of claim 1, wherein the selection of voxels that are contiguous includes use of a cluster algorithm to select centers of gravity of peak clusters.

* * * * *